United States Patent
Ohki et al.

(10) Patent No.: US 7,129,232 B2
(45) Date of Patent: Oct. 31, 2006

(54) CEPHEM COMPOUNDS

(75) Inventors: Hidenori Ohki, Osaka (JP); Shinya Okuda, Osaka (JP); Toshio Yamanaka, Osaka (JP); Masaru Ohgaki, Osaka (JP); Ayako Toda, Osaka (JP); Kohji Kawabata, Osaka (JP); Satoshi Inoue, Takata-gun (JP); Keiji Misumi, Takata-gun (JP); Kenji Itoh, Takata-gun (JP); Kenji Satoh, Takata-gun (JP)

(73) Assignees: Astellas Pharma Inc., Tokyo (JP); Wakunaga Pharmaceutical Co., Ltd, Osaka (JP)

( * ) Notice: Subject to any disclaimer, the term of this patent is extended or adjusted under 35 U.S.C. 154(b) by 357 days.

(21) Appl. No.: 10/695,895

(22) Filed: Oct. 30, 2003

(65) Prior Publication Data

US 2004/0132994 A1    Jul. 8, 2004

(30) Foreign Application Priority Data

Oct. 30, 2002    (AU) ............................. 2002952355
Sep. 4, 2003    (AU) ............................. 2003904813

(51) Int. Cl.
C07D 501/46    (2006.01)
C07D 501/38    (2006.01)
A61K 31/546    (2006.01)
A61P 31/04    (2006.01)

(52) U.S. Cl. ...................... 514/202; 540/222
(58) Field of Classification Search ................ None
See application file for complete search history.

(56) References Cited

U.S. PATENT DOCUMENTS

| | | | | |
|---|---|---|---|---|
| 4,927,818 | A * | 5/1990 | Takaya et al. | 514/202 |
| 4,952,578 | A * | 8/1990 | Sakane et al. | 514/202 |
| 5,109,130 | A * | 4/1992 | Sakane et al. | 540/222 |
| 5,173,485 | A * | 12/1992 | Sakane et al. | 514/202 |
| 5,187,160 | A * | 2/1993 | Sakane et al. | 514/202 |
| 5,194,432 | A | 3/1993 | Takaya et al. | |
| 5,210,080 | A * | 5/1993 | Takaya et al. | 514/202 |
| 5,215,982 | A * | 6/1993 | Sakane et al. | 514/202 |
| 5,663,163 | A * | 9/1997 | Takaya et al. | 514/202 |
| 2004/0248875 | A1* | 12/2004 | Ohki et al. | 514/202 |
| 2005/0004094 | A1* | 1/2005 | Yamanaka et al. | 514/202 |
| 2005/0096306 | A1* | 5/2005 | Yamanaka et al. | 514/202 |

FOREIGN PATENT DOCUMENTS

| | | |
|---|---|---|
| EP | 0 047 977 | 3/1982 |
| EP | 0 771 803 | 5/1997 |
| EP | 1 134 222 | 9/2001 |
| WO | WO 97/41128 | 11/1997 |
| WO | WO 02/090364 | 11/2002 |

OTHER PUBLICATIONS

Derwent Publications, AN 1992-387716, JP 04-288086, Oct. 13, 1992.

R. F. Brown, et al., Journal of Medicinal Chemistry, vol. 33, No. 8, pp. 2114-2121, XP-001084083, "Synthesis and Biological Evaluation of a Series of Parenteral 3'-Quaternary Ammonium Cephalosporins[1]", 1990.

K. Sakagami, et al., Chem. Pharm. Bull, vol. 38, No. 8, pp. 2271-2273, XP-001083825, "Synthetic Cephalosporins. VI.[1)] Synthesis and Antibacterial Activity of 7-[(Z)-2-(2-Aminothiazol-4-YL)-2-(1-Carboxy-1-Methyl)Ethoxyiminoacetamido]-3-(3-Hydroxy-4-Pyridon-1-YL)Methyl-3-Cephem-4-Carboxylic Acid and Related Compounds", 1990.

* cited by examiner

Primary Examiner—Mark L. Berch
(74) Attorney, Agent, or Firm—Oblon, Spivak, McClelland, Maier & Neustadt, P.C.

(57) ABSTRACT

The present invention relates to a compound of the formula [I]:

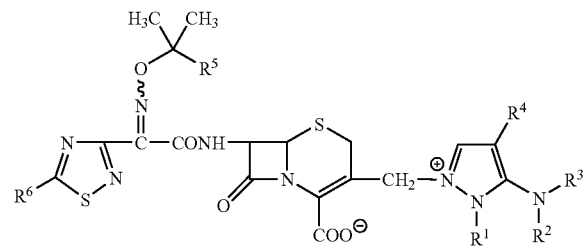

wherein
$R^1$ is lower alkyl, hydroxy(lower)alkyl or halo(lower)alkyl, and
$R^2$ is hydrogen or amino protecting group, or
$R^1$ and $R^2$ are bonded together and form lower alkylene or lower alkenylene;
$R^3$ is hydrogen or lower alkyl;
$R^4$ is

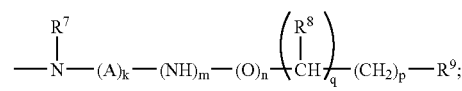

$R^5$ is carboxy or protected carboxy; and
$R^6$ is amino or protected amino,
or a pharmaceutically acceptable salt thereof, a process for preparing a compound of the formula [I], and a pharmaceutical composition comprising a compound of the formula [I] in admixture with a pharmaceutically acceptable carrier.

19 Claims, No Drawings

CEPHEM COMPOUNDS

TECHNICAL FIELD

The present invention relates to new cephem compounds and pharmaceutically acceptable salts thereof. More particularly, the present invention relates to new cephem compounds and pharmaceutically acceptable salts thereof, which have antimicrobial activities, to processes for preparation thereof, to pharmaceutical composition comprising the same, and to a method for treating infectious diseases in human being and animals.

DISCLOSURE OF INVENTION

One object of the present invention is to provide novel cephem compounds and pharmaceutically acceptable salts thereof, which are highly active against a number of pathogenic microorganisms.

Another object of the present invention is to provide processes for the preparation of said cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula [I]:

wherein
$R^1$ is lower alkyl, hydroxy(lower)alkyl or halo(lower)alkyl, and
$R^2$ is hydrogen or amino protecting group, or
$R^1$ and $R^2$ are bonded together and form lower alkylene or lower alkenylene;
$R^3$ is hydrogen or lower alkyl;
$R^4$ is wherein
A is or wherein X is O or NH,
$R^7$ is hydrogen, lower alkyl or amino protecting group,
$R^8$ is hydrogen or hydroxy,
$R^9$ is amino, mono or di(lower)alkylamino, protected amino, guanidino, protected guanidino or saturated 3- to 8-membered heterocyclic group containing 1 to 4 nitrogen atoms optionally substituted by amino or protected amino,
k, m, n and q are independently 0 or 1, and
p is 0, 1, 2 or 3;
$R^5$ is carboxy or protected carboxy; and
$R^6$ is amino or protected amino.

As to the object compound [I], the following points are to be noted.

That is, the object compound [I] includes syn isomer (Z form), anti isomer (E form) and a mixture thereof. Syn isomer (Z form) means one geometrical isomer having the partial structure represented by the following formula:

wherein $R^5$ and $R^6$ are each as defined above, and anti isomer (E form) means the other geometrical isomer having the partial structure represented by the following formula:

wherein $R^5$ and $R^6$ are each as defined above, and all of such geometrical isomers and mixture thereof are included within the scope of this invention.

In the present specification and claims, the partial structure of these geometrical isomers and mixture thereof are represented for convenience' sake by the following formula:

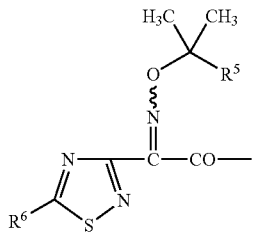

wherein $R^5$ and $R^6$ are each as defined above.

Another point to be noted is that the pyrazolio moiety of the compound [I] can also exist in the tautomeric form, and such tautomeric equilibrium can be represented by the following formula.

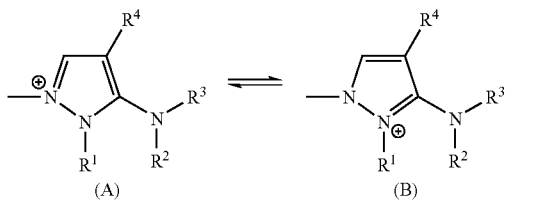

wherein $R^1$, $R^2$, $R^3$ and $R^4$ are each as defined above.

Both of the above tautomeric isomers are included within the scope of the present invention, and in the present specification and claims, however, the object compound [I] is represented for convenience' sake by one expression of the pyrazolio group of the formula (A).

The cephem compound [I] of the present invention can be prepared by the following processes as illustrated in the following.

Process 1

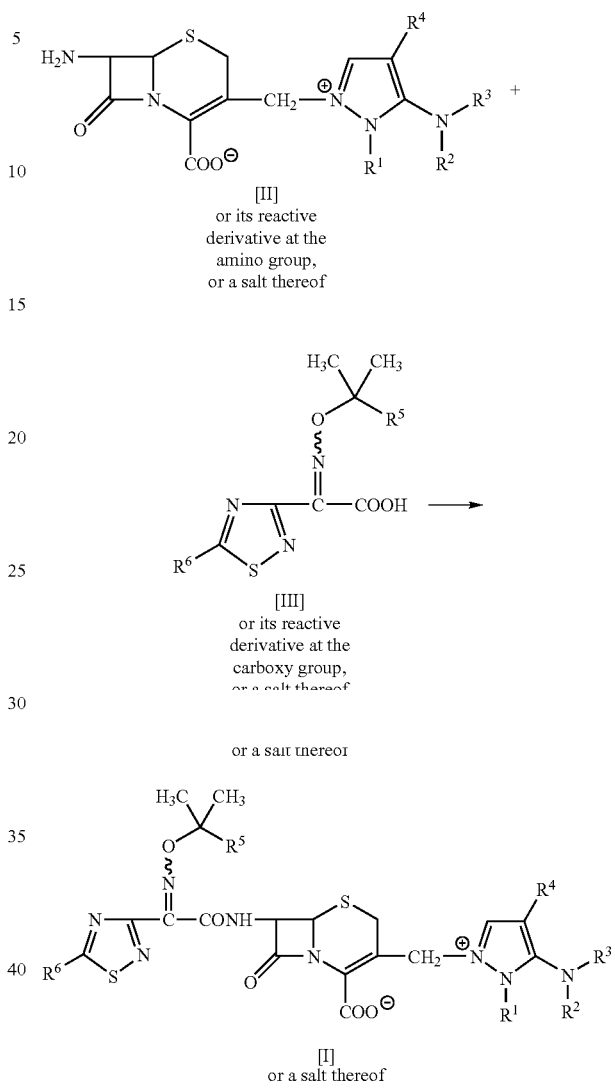

Process 2

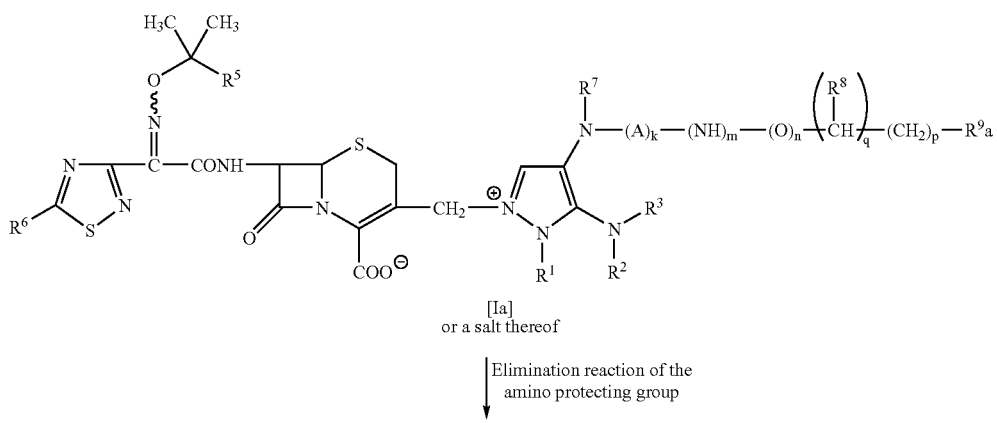

-continued
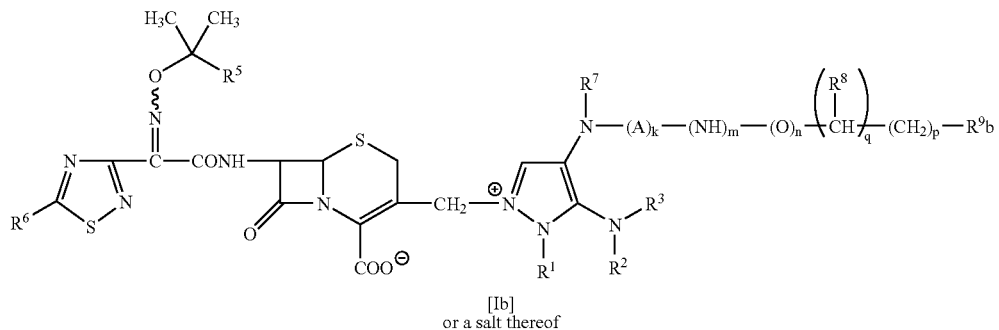
[Ib]
or a salt thereof
Process 3
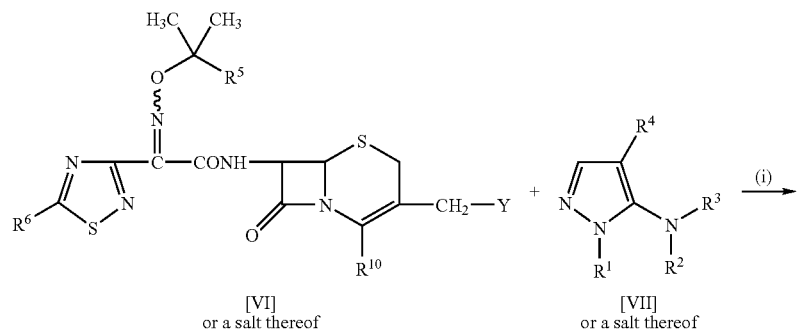
[VI]
or a salt thereof
[VII]
or a salt thereof
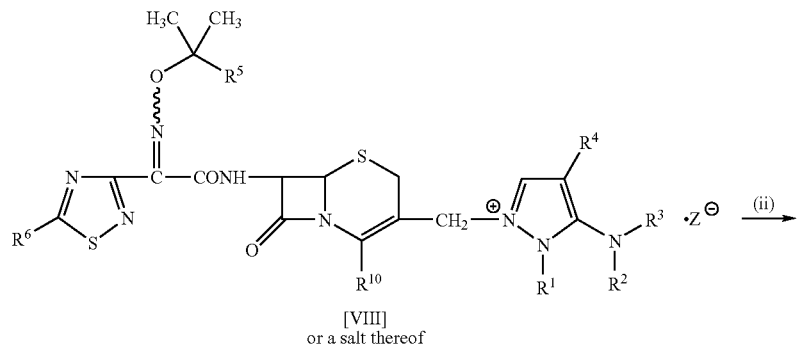
[VIII]
or a salt thereof
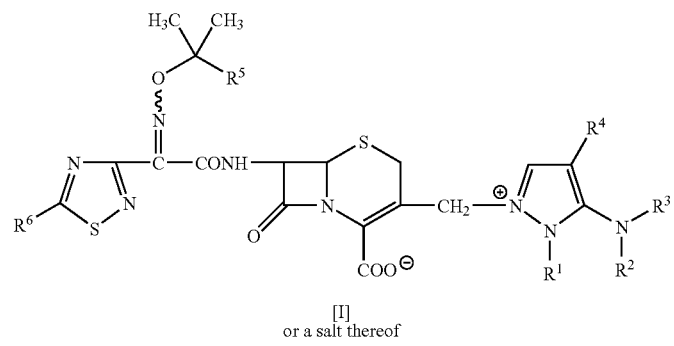
[I]
or a salt thereof Process 4

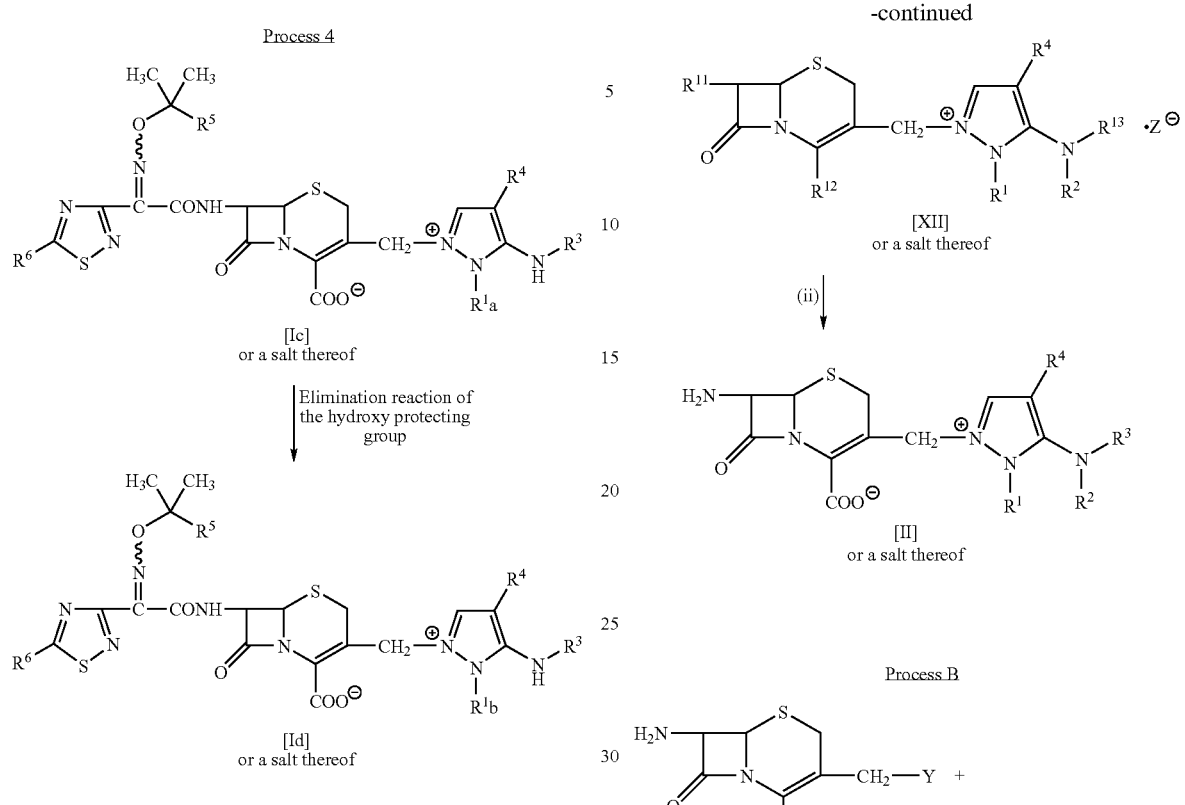

wherein $R^1$, $R^2$, $R^3$, $R^4$, $R^5$, $R^6$, $R^7$, $R^8$, A, k, m, n, p and q are each as defined above,
$R^{10}$ is protected carboxy,
Y is a leaving group,
Z is an anion,
$R^1a$ is protected hydroxy(lower)alkyl,
$R^1b$ is hydroxy(lower)alkyl,
$R^9a$ is protected amino, protected guanidino or saturated 3- to 8-membered heterocyclic group containing 1 to 4 nitrogen atoms substituted by protected amino, and
$R^9b$ is amino, guanidino or saturated 3- to 8-membered heterocyclic group containing 1 to 4 nitrogen atoms substituted by amino.

The starting compounds [II] and [VI] can be prepared by the following processes.

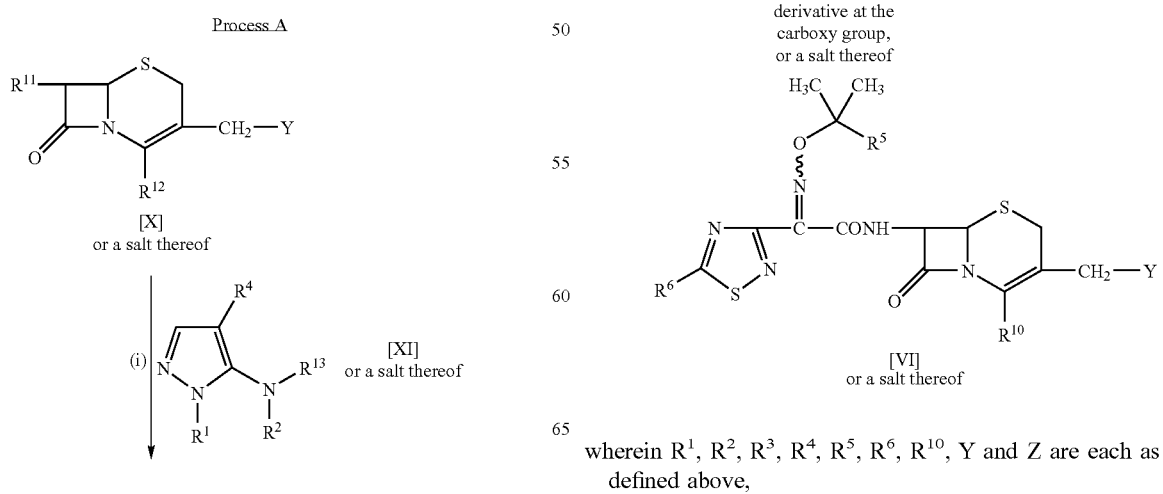

wherein $R^1$, $R^2$, $R^3$, $R^4$, $R^5$, $R^6$, $R^{10}$, Y and Z are each as defined above, $R^{11}$ is protected amino, $R^{12}$ is protected carboxy, and $R^{13}$ is amino protecting group or lower alkyl.

The starting compounds [VII] and [XI] or salts thereof can be prepared by the methods disclosed in the Preparations 3–6, 8–47 and 49–102 described later or similar manners thereto.

In the above and subsequent descriptions of this specification, suitable examples of the various definitions are explained in detail as follows.

The term "lower" is used to mean a group having 1 to 6, preferably 1 to 4, carbon atoms, unless otherwise indicated.

Suitable "lower alkyl" and "lower alkyl" moiety in "hydroxy(lower)alkyl", "protected hydroxy(lower)alkyl", "aryl(lower)alkyl", "halo(lower)alkyl" and "mono or di(lower)alkylamino", include straight or branched alkyl having 1 to 6 carbon atoms, such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "hydroxy(lower)alkyl" includes hydroxy($C_1$–$C_6$) alkyl such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and 6-hydroxyhexyl, in which more preferred one is hydroxy($C_1$–$C_4$)alkyl.

Suitable "halo(lower)alkyl" includes straight or branched alkyl having 1 to 6 carbon atoms substituted by 1 to 5 halogen atoms such as chlorine, bromine, iodine and fluorine. Preferred examples of "halo(lower)alkyl" include fluoromethyl, difluoromethyl, trifluoromethyl, chloromethyl, bromomethyl, 2-fluoroethyl, 2,2-difluoroethyl, 2,2,2-trifluoroethyl, 2-chloroethyl, 2,2-dichloroethyl, 2,2,2-trichloroethyl, 3-fluoropropyl and 2,2,3,3,3-pentafluoropropyl, in which more preferred one is halo($C_1$–$C_4$) alkyl.

Suitable "mono or di(lower)alkylamino" includes mono or di($C_1$–$C_6$)alkylamino such as methylamino, dimethylamino, ethylamino, diethylamino, N-ethyl-N-methylamino, propylamino, butylamino and N-ethyl-N-propylamino, in which more preferred one is mono or di($C_1$–$C_4$)alkylamino.

Suitable "lower alkylene" formed by $R^1$ and $R^2$ includes straight alkylene having 1 to 6, preferably 2 to 4 carbon atoms, such as methylene, ethylene, trimethylene and tetramethylene, in which more preferred one is straight alkylene having 2 or 3 carbon atoms.

Suitable "lower alkenylene" formed by $R^1$ and $R^2$ includes straight alkenylene having 2 to 6, preferably 2 to 4 carbon atoms, such as vinylene and propenylene, in which more preferred one is straight alkenylene having 2 or 3 carbon atoms.

Suitable "saturated 3- to 8-membered heterocyclic group containing 1 to 4 nitrogen atoms" includes azetidinyl (e.g., 1-azetidinyl and 3-azetidinyl), pyrrolidinyl (e.g., 1-pyrrolidinyl and 3-pyrrolidinyl), imidazolidinyl (e.g., 1-imidazolidinyl and 4-imidazolidinyl), piperidinyl (e.g., 1-piperidinyl and 4-piperidinyl) and piperazinyl (e.g., 1-piperazinyl), in which more preferred one is saturated 4- to 6-membered heterocyclic group containing 1 to 4 nitrogen atoms.

The saturated 3- to 8-membered heterocyclic group containing 1 to 4 nitrogen atoms is optionally substituted by amino or protected amino. Suitable examples of "saturated 3- to 8-membered heterocyclic group containing 1 to 4 nitrogen atoms optionally substituted by amino or protected amino" include 1-azetidinyl, 3-amino-1-azetidinyl, 3-tert-butoxycarbonylamino-1-azetidinyl, 3-azetidinyl, 1-pyrrolidinyl, 3-amino-1-pyrrolidinyl, 3-tert-butoxycarbonylamino-1-pyrrolidinyl, 3-pyrrolidinyl, 1-piperidinyl, 4-piperidinyl and 1-piperazinyl.

Suitable "aryl" moiety in "aryl(lower)alkyl" includes $C_6$–$C_{12}$ aryl such as phenyl and naphthyl, in which more preferred one is phenyl.

Suitable "aryl(lower)alkyl" includes mono-, di- or triphenyl(lower)alkyl such as benzyl, phenethyl, benzhydryl and trityl.

Suitable "lower alkanoyl" and "lower alkanoyl" moiety in "lower alkanoylamino" include straight or branched alkanoyl having 1 to 6 carbon atoms, such as formyl, acetyl, propionyl, butyryl, isobutyryl, valeryl, isovaleryl, pivaloyl and hexanoyl, in which more preferred one is $C_1$–$C_4$ alkanoyl.

Suitable "lower alkoxy" moiety in "lower alkoxycarbonyl" and "lower alkoxycarbonylamino" includes straight or branched alkoxy having 1 to 6 carbon atoms, such as methoxy, ethoxy, propoxy, isopropoxy, butoxy, isobutoxy, sec-butoxy, tert-butoxy, pentyloxy, tert-pentyloxy and hexyloxy, in which more preferred one is $C_1$–$C_4$ alkoxy.

Suitable "amino protecting group" in "protected amino" includes an acyl group as mentioned below, substituted or unsubstituted aryl(lower)alkylidene [e.g., benzylidene, hydroxybenzylidene, etc.], aryl(lower)alkyl such as mono-, di- or triphenyl(lower)alkyl [e.g., benzyl, phenethyl, benzhydryl, trityl, etc.], and the like.

Suitable "acyl" includes lower alkanoyl [e.g., formyl, acetyl, propionyl, hexanoyl, pivaloyl, etc.], mono(or di or tri)halo(lower)alkanoyl [e.g., chloroacetyl, trifluoroacetyl, etc.], lower alkoxycarbonyl [e.g., methoxycarbonyl, ethoxycarbonyl, tert-butoxycarbonyl, tert-pentyloxycarbonyl, hexyloxycarbonyl, etc.], carbamoy, aroyl [e.g., benzoyl, toluoyl, naphthoyl, etc.], aryl(lower)alkanoyl [e.g., phenylacetyl, phenylpropionyl, etc.], aryloxycarbonyl [e.g., phenoxycarbonyl, naphthyloxycarbonyl, etc.], aryloxy(lower)alkanoyl [e.g., phenoxyacetyl, phenoxypropionyl, etc.], arylglyoxyloyl [e.g., phenylglyoxyloyl, naphthylglyoxyloyl, etc.], aryl(lower)alkoxycarbonyl which optionally substituted by suitable substituent(s) [e.g., benzyloxycarbonyl, phenethyloxycarbonyl, p-nitrobenzyloxycarbonyl, etc.], and the like.

Preferable examples of "amino protecting group" include aryl(lower)alkyl and acyl, in which more preferred ones are aryl(lower)alkyl, lower alkanoyl and lower alkoxycarbonyl, and particularly preferred ones are mono-, di- or triphenyl ($C_1$–$C_6$)alkyl, $C_1$–$C_6$ alkanoyl and ($C_1$–$C_6$)alkoxycarbonyl.

Preferable examples of "protected amino" include aryl (lower)alkylamino and acylamino, in which more preferred ones are aryl(lower)alkylamino, lower alkanoylamino and lower alkoxycarbonylamino, and particularly preferred ones are mono-, di- or triphenyl($C_1$–$C_6$)alkylamino, $C_1$–$C_6$ alkanoylamino and ($C_1$–$C_6$)alkoxycarbonylamino.

Preferable examples of "protected guanidino" include acylguanidino (monoacylguanidino and diacylguanidino) such as 2,3-bis[(lower)alkoxycarbonyl]guanidino [e.g., 2,3-bis(tert-butoxycarbonyl)guanidino], in which more preferred one is 2,3-bis[($C_1$–$C_6$)alkoxycarbonyl]guanidino.

Suitable "protected hydroxy" in the "protected hydroxy (lower)alkyl" includes acyloxy group, aryl(lower)alkyloxy group, and the like. Suitable "acyl" moiety in the "acyloxy" includes lower alkanoyl [e.g., formyl, acetyl, propionyl, hexanoyl, pivaloyl, etc.], mono(or di or tri)halo(lower)alkanoyl, [e.g. chloroacetyl, trifluoroacetyl, etc.], lower alkoxycarbonyl, [e.g., methoxycarbonyl, ethoxycarbonyl, tert-butoxycarbonyl, tert-pentyloxycarbonyl, hexyloxycarbonyl, etc.], carbamoyl, and the like. Suitable "aryl(lower) alkyl" moiety in the "aryl(lower)alkyloxy" includes mono-, di- or triphenyl(lower)alkyl [e.g., benzyl, phenethyl, benzhydryl, trityl, etc.], and the like.

Suitable "protected carboxy" includes esterified carboxy and the like, and concrete examples of esterified carboxy include lower alkoxycarbonyl [e.g., methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, 1-cyclopropylethoxycarbonyl, etc.] which may have suitable substituent(s), for example, lower alkanoyloxy(lower)alkoxycarbonyl [e.g., acetoxymethoxycarbonyl, propionyloxymethoxycarbonyl, butyryloxymethoxycarbonyl, valeryloxymethoxycarbonyl, pivaloyloxymethoxycarbonyl, 1-acetoxyethoxycarbonyl, 1-propionyloxyethoxycarbonyl, 2-propionyloxyethoxycarbonyl, hexanoyloxymethoxycarbonyl, etc.], lower alkanesulfonyl(lower)alkoxycarbonyl, [e.g., 2-mesylethoxycarbonyl, etc.] or mono(or di or tri)halo (lower)alkoxycarbonyl [e.g., 2-iodoethoxycarbonyl, 2,2,2-trichloroethoxycarbonyl, etc.]; lower alkenyloxycarbonyl [e.g., vinyloxycarbonyl, allyloxycarbonyl, etc.]; lower alkynyloxycarbonyl [e.g., ethynyloxycarbonyl, propynyloxycarbonyl, etc.]; aryl(lower)alkoxycarbonyl which may have suitable substituent(s) [e.g., benzyloxycarbonyl, 4-methoxybenzyloxycarbonyl, 4-nitrobezyloxycarbonyl, phenethyloxycarbonyl, trityloxycarbonyl, benzhydryloxycarbonyl, bis(methoxyphenyl)methoxycarbonyl, 3,4-dimethoxybenzyloxycarbonyl, 4-hydroxy-3,5-di-tert-butylbenzyloxycarbonyl, etc.]; aryloxycarbonyl which may have suitable substituent(s) [e.g., phenoxycarbonyl, 4-chlorophenoxycarbonyl, tolyloxycarbonyl, 4-tert-butylphenoxycarbonyl, xylyloxycarbonyl, mesityloxycarbonyl, cumenyloxycarbonyl, etc.]; and the like.

Preferable examples of "protected carboxy" include lower alkoxycarbonyl and aryl(lower)alkoxycarbonyl which may have suitable substituent(s), in which more preferred one is $(C_1-C_6)$alkoxycarbonyl.

Suitable "leaving group" includes halogen [e.g., chlorine, bromine, iodine, etc.] or acyloxy such as arylsulfonyloxy [e.g., benzenesulfonyloxy, tosyloxy, etc.], lower alkylsulfonyloxy [e.g., mesyloxy, etc.], lower alkanoyloxy [e.g., acetyloxy, propionyloxy, etc.], and the like.

Suitable "anion" includes formate, acetate, trifluoroacetate, maleate, tartrate, methanesulfonate, benzenesulfonate, toluenesulfonate, chloride, bromide, iodide, sulfate, hydrogen sulfate, phosphate, and the like.

Suitable pharmaceutically acceptable salts of the object compound [I] are conventional non-toxic salts and include, for example, a salt with a base or an acid addition salt such as a salt with an inorganic base, for example, an alkali metal salt [e.g., sodium salt, potassium salt, etc.], an alkaline earth metal salt [e.g., calcium salt, magnesium salt, etc.], an ammonium salt; a salt with an organic base, for example, an organic amine salt [e.g., trimethylamine salt, triethylamine salt, pyridine salt, picoline salt, ethanolamine salt, triethanolamine salt, dicyclohexylamine salt, N,N'-dibenzylethylenediamine salt, etc.]; an inorganic acid addition salt [e.g., hydrochloride, hydrobromide, sulfate, hydrogen sulfate, phosphate, etc.]; an organic carboxylic or sulfonic acid addition salt [e.g., formate, acetate, trifluoroacetate, maleate, tartrate, citrate, fumarate, methanesulfonate, benzenesulfonate, toluenesulfonate, etc.]; and a salt with a basic or acidic amino acid [e.g., arginine, aspartic acid, glutamic acid, etc.].

The preferred embodiments of the cephem compound of the present invention represented by the general formula [I] are as follows.

(1) The compound of the formula [I] wherein
$R^1$ is lower alkyl or hydroxy(lower)alkyl, and
$R^2$ is hydrogen or amino protecting group, or
$R^1$ and $R^2$ are bonded together and form lower alkylene;
$R^3$ is hydrogen;
A is

wherein X is O or NH;
$R^7$ is hydrogen or amino protecting group;
$R^9$ is amino or protected amino; and
p is 0, 1 or 2,
or a pharmaceutically acceptable salt thereof.
(2) The compound of (1) above wherein $R^8$ is hydrogen, or a pharmaceutically acceptable salt thereof.
(3) The compound of the formula [I] wherein
$R^1$ is lower alkyl, hydroxy(lower)alkyl or halo(lower)alkyl, and
$R^2$ is hydrogen, aryl(lower)alkyl or acyl, or
$R^1$ and $R^2$ are bonded together and form lower alkylene or lower alkenylene;
$R^5$ is carboxy or esterified carboxy;
$R^6$ is amino or acylamino;
$R^7$ is hydrogen, lower alkyl or acyl; and
$R^9$ is amino, mono or di(lower)alkylamino, acylamino, guanidino, acylguanidino or saturated 3- to 8-membered heterocyclic group containing 1 to 4 nitrogen atoms optionally substituted by amino or acylamino,
or a pharmaceutically acceptable salt thereof.
(4) The compound of (3) above wherein
$R^1$ is lower alkyl or hydroxy(lower)alkyl, and
$R^2$ is hydrogen, aryl(lower)alkyl or acyl, or
$R^1$ and $R^2$ are bonded together and form lower alkylene;
$R^5$ is carboxy or esterified carboxy;
$R^6$ is amino or acylamino;
$R^7$ is hydrogen or acyl; and
$R^9$ is amino or acylamino,
or a pharmaceutically acceptable salt thereof.
(5) The compound of (4) above wherein
$R^1$ is lower alkyl or hydroxy(lower)alkyl, and
$R^2$ is hydrogen, aryl(lower)alkyl, lower alkanoyl or lower alkoxycarbonyl, or
$R^1$ and $R^2$ are bonded together and form lower alkylene;
$R^5$ is carboxy or lower alkoxycarbonyl;
$R^6$ is amino, lower alkanoylamino or lower alkoxycarbonylamino;
$R^7$ is hydrogen, lower alkanoyl or lower alkoxycarbonyl; and
$R^9$ is amino, lower alkanoylamino or lower alkoxycarbonylamino,
or a pharmaceutically acceptable salt thereof.
(6) The compound of (5) above wherein
$R^1$ is $C_1-C_6$ alkyl or hydroxy$(C_1-C_6)$alkyl, and
$R^2$ is hydrogen, mono-, di- or triphenyl$(C_1-C_6)$alkyl, $C_1-C_6$ alkanoyl or $(C_1-C_6)$alkoxycarbonyl, or
$R^1$ and $R^2$ are bonded together and form $C_1-C_6$ alkylene;
$R^5$ is carboxy or $(C_1-C_6)$alkoxycarbonyl;
$R^6$ is amino, $C_1-C_6$ alkanoylamino or $(C_1-C_6)$alkoxycarbonylamino;
$R^7$ is hydrogen, $C_1-C_6$ alkanoyl or $(C_1-C_6)$alkoxycarbonyl; and
$R^9$ is amino, $C_1-C_6$ alkanoylamino or $(C_1-C_6)$alkoxycarbonylamino,
or a pharmaceutically acceptable salt thereof.

(7) The compound of (5) above wherein
 $R^1$ is lower alkyl or hydroxy(lower)alkyl, and
 $R^2$ is hydrogen, or
 $R^1$ and $R^2$ are bonded together and form lower alkylene;
 $R^5$ is carboxy;
 $R^6$ is amino;
 $R^7$ is hydrogen or lower alkanoyl; and
 $R^9$ is amino,
or a pharmaceutically acceptable salt thereof.
(8) The compound of (7) above wherein
 $R^1$ is $C_1$–$C_6$ alkyl or hydroxy($C_1$–$C_6$)alkyl, and
 $R^2$ is hydrogen, or
 $R^1$ and $R^2$ are bonded together and form $C_1$–$C_6$ alkylene;
 $R^5$ is carboxy;
 $R^6$ is amino;
 $R^7$ is hydrogen or $C_1$–$C_6$ alkanoyl; and
 $R^9$ is amino,
or a pharmaceutically acceptable salt thereof.
(9) The compound of the formula [I] wherein
 $R^4$ is selected from the group consisting of

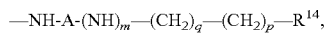

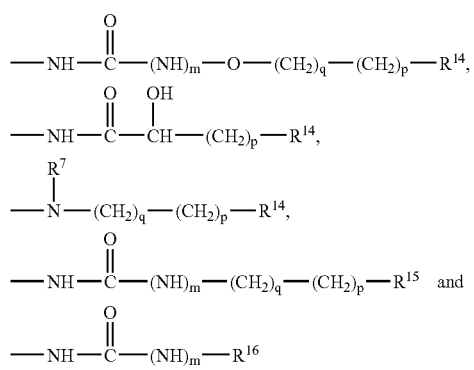

wherein $R^7$, A, m, p and q are each as defined above in the formula [I],
 $R^{14}$ is amino, mono or di(lower)alkylamino or protected amino,
 $R^{15}$ is guanidino or protected guanidino, and
 $R^{16}$ is saturated 3- to 8-membered heterocyclic group containing 1 to 4 nitrogen atoms optionally substituted by amino or protected amino,
or a pharmaceutically acceptable salt thereof.
(10) The compound of the formula [I] wherein
 $R^4$ is selected from the group consisting of

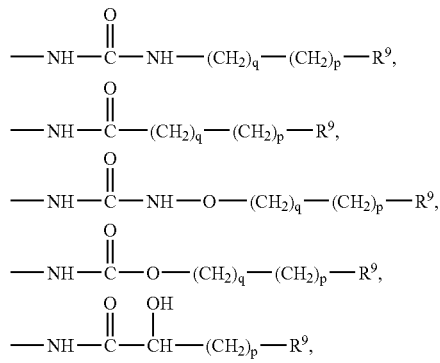

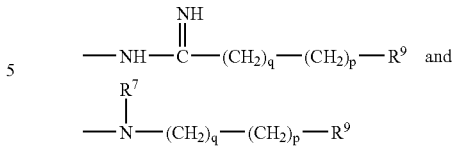

wherein
p is 0, 1 or 2,
q is 0 or 1,
 $R^7$ is hydrogen or amino protecting group, and
 $R^9$ is amino or protected amino,
or a pharmaceutically acceptable salt thereof.
(11) The compound of (10) above wherein
 $R^7$ is hydrogen, lower alkanoyl or lower alkoxycarbonyl; and
 $R^9$ is amino, lower alkanoylamino or lower alkoxy carbonylamino,
or a pharmaceutically acceptable salt thereof.
(12) The compound of (11) above wherein
 $R^7$ is hydrogen, $C_1$–$C_6$ alkanoyl or ($C_1$–$C_6$ alkoxycarbonyl; and
 $R^9$ is amino, $C_1$–$C_6$ alkanoylamino or ($C_1$–$C_6$)alkoxycarbonylamino,
or a pharmaceutically acceptable salt thereof.
(13) The compound of (11) above wherein
 $R^7$ is hydrogen or lower alkanoyl; and
 $R^9$ is amino,
or a pharmaceutically acceptable salt thereof.
(14) The compound of (13) above wherein
 $R^7$ is hydrogen or $C_1$–$C_6$ alkanoyl; and
 $R^9$ is amino,
or a pharmaceutically acceptable salt thereof.

The processes for preparing the object compound of the present invention are explained in detail in the following.

Process 1

The compound [I] or a salt thereof can be prepared by reacting the compound [II] or its reactive derivative at the amino group, or a salt thereof with the compound [III] or its reactive derivative at the carboxy group, or a salt thereof.

Suitable reactive derivative at the amino group of the compound [II] includes Schiff's base type imino or its tautomeric enamine type isomer formed by the reaction of the compound [II] with a carbonyl compound such as aldehyde, ketone and the like; a silyl derivative formed by the reaction of the compound [II] with a silyl compound such as bis(trimethylsilyl)acetamide, mono(trimethylsilyl)acetamide [e.g., N-(trimethylsilyl)acetamide], bis(trimethylsilyl)urea and the like; a derivative formed by the reaction of the compound [II] with phosphorus trichloride or phosgene.

Suitable salts of the compound [II] and its reactive derivative can be referred to the ones as exemplified for the compound [I].

Suitable reactive derivative at the carboxy group of the compound [III] includes an acid halide, an acid anhydride, an activated amide, and an activated ester. A suitable example of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, alkanesulfonic acid [e.g., methanesulfonic acid, etc.], aliphatic carboxylic acid [e.g., acetic acid, propionic acid, butyric acid, isobutyric acid, pivalic acid, pentanoic acid, isopentanoic acid, 2-ethylbutyric acid, trichloroacetic acid, etc.] and aromatic carboxylic acid [e.g., benzoic acid, etc.]; a symmetrical acid anhydride; an activated amide with imidazole, 4-substituted imidazole, dimethylpyrazole, triazole or tetrazole; an activated ester [e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.]; or an ester with an N-hydroxy compound [e.g., N,N-dimethylhydroxylamine, 1-hydroxy-2-(1H)-pyridone, N-hydroxysuccinimide, N-hydroxyphthalimide, N-hydroxy-1H-benzotriazole, etc.]. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely affect the reaction. These conventional solvents may also be used in a mixture with water.

In this reaction, when the compound [III] is used in free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.], triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; and the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, and the like.

The reaction temperature is not critical, and the reaction is usually carried out under cooling to warming.

Process 2

The compound [Ib] or a salt thereof can be prepared by subjecting the compound [Ia] or a salt thereof to elimination reaction of the amino protecting group.

Elimination reaction is carried out in accordance with a conventional method such as hydrolysis and the like.

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

Process 3-(i)

The compound [VIII] or a salt thereof can be prepared by reacting the compound [VI] or a salt thereof with the compound [VII] or a salt thereof.

Suitable salt of the compounds [VI], [VII] and [VIII] can be referred to the ones as exemplified for the compound [I].

The present reaction may be carried out in a solvent such as water, phosphate buffer, acetone, chloroform, acetonitrile nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [VII] is liquid, it can also be used as a solvent.

The reaction is preferably conducted in the presence of a base, for example, an inorganic base such as alkali metal hydroxide, alkali metal carbonate, alkali metal hydrogencarbonate, an organic base such as trialkylamine, and the like.

The reaction temperature is not critical, and the reaction is usually carried out at ambient temperature, under warming or under heating. The present reaction is preferably carried out in the presence of alkali metal halide [e.g., sodium iodide, potassium iodide, etc.], alkali metal thiocyanate [e.g., sodium thiocyanate, potassium thiocyanate, etc.], and the like.

Anion Z may be one derived from a leaving group Y, and it may be converted to other anion by a conventional method.

Process 3-(ii)

The compound [I] or a salt thereof can be prepared by subjecting the compound [VIII] or a salt thereof to elimination reaction of the carboxy protecting group.

Elimination reaction is carried out in similar manner to the reaction in the aforementioned Process 2, and therefore the reagents to be used and reaction conditions (e.g., solvent, reaction temperature, etc.) can be referred to those of Process 2.

Process 4

The compound [Id] or a salt thereof can be prepared by subjecting the compound [Ic] or a salt thereof to elimination reaction of the hydroxy protecting group.

Suitable method of this elimination reaction includes conventional one such as hydrolysis, reduction and the like.

(i) For Hydrolysis

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.] and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

(ii) For Reduction

Reduction is carried out in a conventional manner, including chemical reduction and catalytic reduction.

Suitable reducing reagents to be used in chemical reduction are a combination of a metal [e.g., tin, zinc, iron, etc.] or metallic compound [e.g., chromium chloride, chromium acetate, etc.] and an organic acid or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g., platinum plate, spongy platinum, platinum black, colloidal platinum, platinum oxide, platinum wire, etc.], palladium catalysts [e.g., spongy palladium, palladium black, palladium oxide, palladium on carbon, colloidal palladium, palladium on barium sulfate, palladium on barium carbonate, etc.], nickel catalysts [e.g., reduced nickel, nickel oxide, Raney nickel, etc.], cobalt catalysts [e.g., reduced cobalt, Raney cobalt, etc.], iron catalysts [e.g., reduced iron, Raney iron, etc.], copper catalysts [e.g., reduced copper, Raney copper, Ullman copper, etc.] and the like.

The reduction is usually carried out in a conventional solvent which does not adversely influence the reaction such as water, methanol, ethanol, propanol, N,N-dimethylformamide or a mixture thereof.

Additionally, in case that the above-mentioned acids to be used in chemical reduction are liquid, they can also be used as a solvent.

Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried but under cooling to warming.

When $R^6$ is protected amino, the amino protecting group in $R^6$ can be eliminated by a conventional method such as hydrolysis.

Processes A and B for the preparation of the starting compounds are explained in detail in the following.

Process A-(i)

The compound [XII] or a salt thereof can be prepared by reacting the compound [X] or a salt thereof with the compound [XI] or a salt thereof.

This reaction can be carried out in a similar manner to the reaction in the aforementioned Process 3-(i), and therefore the reagents to be used and reaction conditions (e.g., solvent, reaction temperature, etc.) can be referred to those of Process 3-(i).

Process A-(ii)

The compound [II] or a salt thereof can be prepared by subjecting the compound [XII] or a salt thereof to elimination reaction of the amino protecting groups in $R^{11}$ and $R^{13}$ and the carboxy protecting group in $R^{12}$.

This reaction can be carried out in a similar manner to the reaction in the aforementioned Process 2, and therefore the reagents to be used and reaction conditions (e.g., solvent, reaction temperature, etc.) can be referred to those of Process 2.

Process B

The compound [VI] or a salt thereof can be prepared by reacting the compound [XIII] or its reactive derivative at the amino group, or a salt thereof with the compound [XIV] or its reactive derivative at the carboxy group, or a salt thereof.

This reaction can be carried out in a similar manner to the reaction in the aforementioned Process 1, and therefore the reagents to be used and reaction conditions (e.g., solvent, reaction temperature, etc.) can be referred to those of Process 1.

The compounds obtained by the above processes can be isolated and purified by a conventional method such as pulverization, recrystallization, column chromatography, reprecipitatipon, and the like.

It is to be noted that the compound [I] and other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds [I] and pharmaceutically acceptable salts thereof include solvates [e.g., enclosure compounds (e.g., hydrate, etc.)].

The object compound [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound [I], the test data on MIC (minimal inhibitory concentration) of a representative compound of this invention are shown in the following.

Test Method

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in μg/ml after incubation at 37° C. for 20 hours.

Test Compound

Compound (a): 7β-[(Z)-2-(5-amino-1,2,4-thiadiazol-3-yl)-2-(1-carboxy-1-methylethoxyimino)acetamido]-3-[7-(3-aminopropionamido)-2,3-dihydro-5-(1H-imidazo[1,2-b]pyrazolio)]methyl-3-cephem-4-carboxylate (Example 3)

Compound (b): 7β-[(Z)-2-(5-amino-1,2,4-thiadiazol-3-yl)-2-(1-carboxy-1-methylethoxyimino)acetamido]-3-[3-amino-4-(3-aminopropionamido)-2-methyl-1-pyrazolio]methyl-3-cephem-4-carboxylate (Example 4)

Compound (c): 7β-[(Z)-2-(5-amino-1,2,4-thiadiazol-3-yl)-2-(1-carboxy-1-methylethoxyimino)acetamido]-3-[3-amino-4-(aminoacetyl)amino-2-methyl-1-pyrazolio]methyl-3-cephem-4-carboxylic acid hydrogen sulfate (Example 6)

Compound (d): 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate (Example 7)

Compound (e): 7β-[(Z)-2-(5-amino-1,2,4-thiadiazol-3-yl)-2-(1-carboxy-1-methylethoxyimino)acetamido]-3-(3-amino-4-guanidino-2-methyl-1-pyrazolio)methyl-3-cephem-4-carboxylic acid hydrogen sulfate (Example 11)

Ceftazidime

Test Results

TABLE 1

| Test strain | Test compound | MIC (μg/ml) |
| --- | --- | --- |
| Pseudomonas aeruginosa FP 1380 | (a) | 2 |
| | (b) | 1 |
| | (c) | 2 |
| | (d) | 2 |
| | (e) | 1 |
| | Ceftazidime | 128 |

For therapeutic administration, the object compound [I] and pharmaceutically acceptable salts thereof of the present invention are used in the form of a conventional pharmaceutical preparation which contains said compound as an active ingredient, in admixture with pharmaceutically acceptable carriers such as an organic or inorganic solid or liquid excipient which is suitable for oral, parenteral or external administration. The pharmaceutical preparations may be in a solid form such as tablet, granule, powder, capsule, or in a liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general amounts between 1 mg and 4,000 mg or even more per day may be administered to a patient. An average single dose of about 50 mg, 100 mg, 250 mg, 500 mg, 1000 mg or 2000 mg of the object compounds [I] of the present invention may be used in treating diseases infected by pathogenic microorganisms.

The following Preparations and Examples are given for the purpose of illustrating the present invention in more detail.

Preparation 1

To a solution of (Z)-2-(5-amino-1,2,4-thiadiazol-3-yl)[(2-tert-butoxy-1,1-dimethyl-2-oxoethoxy)imino]ethanoic acid (5 g) in a mixture of tetrahydrofuran (80 ml) and N,N-dimethylformamide (20 ml) was added a solution of sodium bis(trimethylsilyl)amide (8.33 g) in tetrahydrofuran (12 ml), and the mixture was stirred for 15 minutes. To the reaction mixture was added a solution of di-tert-butyl dicarbonate (3.3 g) in tetrahydrofuran (20 ml) under ice-cooling, and the mixture was stirred under ice-cooling for 3 hours. To the reaction mixture was added ethyl acetate, and the mixture was washed with 10% aqueous potassium hydrogen sulfate solution, and then washed with a phosphate buffer (pH 6.86). The organic layer was separated, dried over anhydrous magnesium sulfate, filtered and concentrated in vacuo. The residue was triturated with diisopropyl ether and dried in vacuo to give (Z)-2-{5-[(tert-butoxycarbonyl)amino]-1,2,4-thiadiazol-3-yl}[(2-tert-butoxy-1,1-dimethyl-2-oxoethoxy)imino]ethanoic acid (3.10 g).

IR(KBr) 3191.6, 2981.4, 1714.4, 1550.5, 1153.2, 1000.9 cm$^{-1}$ $^1$H-NMR(DMSO-d$_6$) δ 1.37 (9H, s), 1.45 (6H, s), 1.50 (9H, s), 12.7 (1H, s)

ESI-MS: m/z=429(M–H)

Preparation 2

A mixture of N,N-dimethylformamide (0.648 ml) and phosphoryl chloride (0.781 ml) was stirred at room temperature for 30 minutes. To the mixture were added tetrahydrofuran (4 ml) and (Z)-2-{5-[(tert-butoxycarbonyl)amino]-1,2,4-thiadiazol-3-yl}[(2-tert-butoxy-1,1-dimethyl-2-oxoethoxy)imino]ethanoic acid (3 g) at 4° C., and the reaction mixture was stirred at room temperature for 1 hour. Meanwhile, a mixture of benzhydryl 7β-amino-3-chloromethyl-3-cephem-4-carboxylate hydrochloride (3 g) and N-(trimethylsilyl)acetamide (8.72 g) in tetrahydrofuran (15 ml) was warmed to make a clear solution. The solution was then cooled to −20° C. and added to the activated acid solution obtained above. The reaction mixture was stirred at a temperature of −10° C. to 0° C. for 1 hour and poured into a mixture of ethyl acetate and water. The aqueous layer was separated, and the organic layer was washed with brine, dried over anhydrous magnesium sulfate and filtered. The filtrate was concentrated in vacuo and purified by column chromatography on silica gel eluting with hexane/ethyl acetate (3:2) to give benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (4.79 g).

IR(KBr) 2981.4, 1793.5, 1720.2, 1524.8, 1371.1, 1247.7, 1151.3 cm$^{-1}$ $^1$H-NMR(DMSO-d$_6$) δ 1.39 (6H, s), 1.48 (3H, s), 1.50 (6H, s), 3.58 (1H, d, J=18.3 Hz), 3.76 (1H, d, J=18.3 Hz), 4.44 (2H, s), 5.29 (1H, d, J=5.0 Hz), 6.01 (1H, dd, J=8.6, 5.0 Hz), 6.97 (1H, s), 7.2–7.6 (10H, m), 9.65 (1H, d, J=5.0 Hz), 12.7 (1H, s)

ESI-MS: m/z=849(M+Na)

Preparation 3

To a solution of 5-amino-1-methylpyrazole (5 g) in ethanol (50 ml) was added isoamyl nitrite (6.92 ml), and then 20% hydrochloric acid (5 drops) was added at 4° C. The reaction mixture was refluxed for 2 hours and cooled to room temperature. To the reaction mixture was added diisopropyl ether (50 ml), and the mixture was stirred for 0.5 hour. The resulting precipitate was collected by filtration and dried in vacuo to give 5-amino-1-methyl-4-nitrosopyrazole (3.53 g).

$^1$H-NMR(DMSO-$d_6$) δ 3.51 (3H, s), 8.07 (2H, brs), 8.51 (1H, s)
APCI-MS: m/z=127(M+H)

Preparation 4

To a solution of 5-amino-1-methyl-4-nitrosopyrazole (1 g) in water (40 ml) were added concentrated sulfuric acid (0.423 ml) and palladium on carbon (0.3 g) under a hydrogen atmosphere. The mixture was stirred overnight. The reaction mixture was filtered, and the filtrate was evaporated in vacuo. To the residue was added isopropyl alcohol, and the resulting precipitate was collected by filtration to give 4,5-diamino-1-methylpyrazole sulfuric acid salt (1.71 g).

$^1$H-NMR(DMSO-$d_6$) δ 3.54 (3H, s), 7.19 (1H, s)
ESI-MS: m/z=113(M+H)

Preparation 5

To a suspension of 1,1'-carbonyldiimidazole (9.73 g) in dehydrated chloroform (72 ml) was added tert-butyl N-(2-aminethyl)carbamate (9.61 g) under ice-cooling, and the mixture was stirred at room temperature for 1 hour. To the reaction mixture were added N-ethyldiisopropylamine (14.22 g) and 4,5-diamino-1-methylpyrazole sulfuric acid salt (10.51 g), and the mixture was stirred at 50° C. for 15 hours. The insoluble materials were removed by filtration. To the filtrate were added chloroform (200 ml) and 5% aqueous sodium hydrogen carbonate solution (100 ml). The organic layer was separated, and the aqueous layer was extracted with a mixed solvent of chloroform and methanol (4:1). The organic layers were combined, dried over anhydrous magnesium sulfate, filtered and concentrated in vacuo. The residue was triturated with ethyl acetate and dried in vacuo to give 5-amino-4-(3-{2-[(tert-butoxycarbonyl)amino]ethyl}ureido)-1-methylpyrazole (14.0 g) as a solid.

$^1$H-NMR(DMSO-$d_6$) δ 1.38 (9H, s), 2.96–2.98 (2H, m), 3.03–3.07 (2H, m), 3.50 (3H, s), 4.81 (2H, br), 5.92 (1H, br), 6.80 (1H, br), 6.96 (1H, s), 7.18 (1H, br)

EXAMPLE 1

To a solution of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (500 mg) in N,N-dimethylformamide (1.0 ml) was added sodium iodide (100 mg), and the mixture was stirred at room temperature for 30 minutes. To the reaction mixture was added a solution of 5-amino-4-(3-{2-[(tert-butoxycarbonyl)amino]ethyl}ureido)-1-methylpyrazole (216 mg) in N,N-dimethylformamide (1.0 ml). The whole mixture was stirred at 32° C. for 4 hours. To the resulting reaction mixture were added ethyl acetate (50 ml) and water (50 ml). The aqueous layer was separated, and the organic layer was washed with 10% aqueous sodium trifluoroacetate solution and brine, dried over anhydrous sodium sulfate and filtered. The filtrate was concentrated to about 5 ml in vacuo. The concentrate was poured into diisopropyl ether (75 ml), and the resulting precipitate was collected by filtration and dried in vacuo. To a solution of the resulting solid in methylene chloride (1.8 ml) were added anisole (0.6 ml) and trifluoroacetic acid (1.2 ml). The resulting solution was stirred at room temperature for 4 hours and poured into diisopropyl ether (80 ml). The resulting precipitate was collected by filtration and dried in vacuo to give a crude product (380 mg), which was purified by preparative high-performance liquid chromatography (HPLC) utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate (21 mg) as an amorphous solid.

$^1$H-NMR($D_2O$) δ 1.52 (3H, s), 1.53 (3H, s), 3.12 (2H, t, J=5.7 Hz), 3.22 (1H, d, J=17.9 Hz), 3.49 (1H, d, J=17.9 Hz), 3.46 (2H, t, J=5.7 Hz), 3.71 (3H, s), 4.95 (1H, d, J=15.6 Hz), 5.15 (1H, d, J=15.6 Hz), 5.25 (1H, d, J=4.6 Hz), 5.84 (1H, d, J=4.6 Hz), 7.89 (1H, s)

Preparation 6

To a solution of 5-amino-4-(3-{2-[(tert-butoxycarbonyl)amino]ethyl}ureido)-1-methylpyrazole (597 mg) and triethylamine (243 mg) in methylene chloride (10 ml) was added triphenylmethyl chloride (669 mg), and the mixture was stirred at room temperature for 19 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was triturated with ethyl acetate to give 4-(3-{2-[(tert-butoxycarbonyl)amino]ethyl}ureido)-1-methyl-5-triphenylmethylaminopyrazole (640 mg) as a solid.

$^1$H-NMR(DMSO-$d_6$) δ 1.38 (9H, s), 2.70 (3H, s), 2.94–2.96 (2H, m), 2.99–3.01 (2H, m), 5.68 (1H, brs), 5.96 (1H, br), 6.78 (1H, br), 6.85 (1H, br), 7.00 (1H, s), 7.13–7.15 (6H, m), 7.24–7.28 (9H, m)

Preparation 7

To a solution of benzhydryl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (60 g) in toluene (600 ml) were added a solution of sodiumiodide (61.8 g) in 0.05 mol phosphate buffer (pH 7, 500 ml) and tricaprylylmethylammonium chloride (6.67 g). The mixture was stirred at room temperature for 15 hours. The reaction mixture was added to a mixture of ethyl acetate and water. The organic layer was washed with water and brine, and then dried over magnesium sulfate. The magnesium sulfate was filtered off, and the filtrate was evaporated to 255 g under reduced pressure. The concentrate was poured into diisopropyl ether (2 L). The resulting precipitate was collected by filtration and dried to give benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (59.4 g).

¹H-NMR(DMSO-d₆) δ 1.39 (9H, s), 1.46 (6H, s), 3.57 and 3.87 (2H, ABq, J=18.0 Hz), 3.76 (3H, s), 4.30 (2H, bs), 5.25 (1H, d, J=4.9 Hz), 5.94 (1H, dd, J =4.9, 8.7 Hz), 6.95 (1H, bs), 7.15–7.60 (10H, m), 8.17 (2H, bs), 9.53 (1H, d, J=8.7 Hz)

EXAMPLE 2

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (810 mg) in N,N-dimethylformamide (2.4 ml) was added N-(trimethylsilyl)acetamide (656 mg), and the mixture was stirred at room temperature for 30 minutes. To the reaction mixture was added a solution of 4-(3-{2-[(tert-butoxycarbonyl)amino]ethyl}ureido)-1-methyl-5-triphenylmethylaminopyrazole (640 mg) in methylene chloride (10 ml). The whole mixture was stirred at room temperature for 26 hours. To the resulting reaction mixture were added ethyl acetate (50 ml) and water (50 ml). The aqueous layer was separated, and the organic layer was washed with 10% aqueous sodium trifluoroacetate solution and brine, dried over anhydrous sodium sulfate and filtered. The filtrate was concentrated to about 5 ml in vacuo. The concentrate was poured into diisopropyl ether (80 ml), and the resulting precipitate was collected by filtration and dried in vacuo. To a solution of the resulting solid in methylene chloride (2.38 ml) were added anisole (0.79 ml) and trifluoroacetic acid (1.58 ml). The resulting solution was stirred at room temperature for 4 hours and poured into diisopropyl ether (80 ml). The resulting precipitate was collected by filtration and dried in vacuo to give a crude product (635 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate (54 mg) as an amorphous solid.

¹H-NMR(D₂O) δ 1.52 (3H, s), 1.53 (3H, s), 3.12 (2H, t, J=5.7 Hz), 3.22 (1H, d, J=17.9 Hz), 3.49 (1H, d, J=17.9 Hz), 3.46 (2H, t, J=5.7 Hz), 3.71 (3H, s), 4.95 (1H, d, J=15.6 Hz), 5.15 (1H, d, J=15.6 Hz), 5.25 (1H, d, J=4.6 Hz), 5.84 (1H, d, J=4.6 Hz), 7.89 (1H, s)

Preparation 8

To a solution of 2,3-dihydro-1H-imidazo[1,2-b]pyrazole (120 g) in sulfuric acid (500 ml) was added potassium nitrate (111 g) under ice-cooling. The mixture was stirred at room temperature for 48 hours. The reaction mixture was added to ice (2.0 kg). The crystalline residue was collected by filtration and dried in vacuo to give 7-nitro-2,3-dihydro-1H-imidazo[1,2-b]pyrazole (132 g) as a solid.

¹H-NMR(DMSO-d₆) δ 4.05–4.09 (2H, m), 4.17–4.20 (2H, m), 7.82 (1H, s), 7.97 (1H, br)

Preparation 9

A suspension of 7-nitro-2,3-dihydro-1H-imidazo[1,2-b]pyrazole (97 g) in a mixed solvent of sulfuric acid (34 ml) and water (2000 ml) was treated with 10% palladium on carbon (10 g) under a hydrogen atmosphere at room temperature for 4 days. After the catalyst was filtered off, the filtrate was concentrated in vacuo. The residue was triturated with methanol and dried in vacuo to give 7-amino-2,3-dihydro-1H-imidazo[1,2-b]pyrazole sulfuric acid salt (90.2 g) as a solid.

¹H-NMR(DMSO-d₆) δ 3.87–3.90 (2H, m), 4.07–4.10 (2H, m), 7.28 (1H, s)

Preparation 10

To a solution of 7-amino-2,3-dihydro-1H-imidazo[1,2-b]pyrazole sulfuric acid salt (2.22 g) and N-ethyldiisopropylamine (2.84 g) in methylene chloride (70 ml) was added N-[3-(tert-butoxycarbonylamino)propionyloxy]succinimide (3.15 g). The mixture was stirred at room temperature for 4 hours. The reaction mixture was washed with saturated aqueous sodium hydrogen carbonate solution, and the organic layer was dried over anhydrous magnesium sulfate, filtered and concentrated in vacuo. The oily residue was purified by column chromatography on silica gel eluting with 5% methanol/chloroform to give 7-[3-(tert-butoxycarbonylamino)propionyl]amino-2,3-dihydro-1H-imidazo[1,2-b]pyrazole (2.2 g) as a solid.

¹H-NMR(CDCl₃) δ 1.44 (9H, s), 2.52 (2H, t, J=6.0 Hz), 3.36–3.47 (2H, m), 3.96 (2H, t, J=8.2 Hz), 4.18 (2H, t, J=8.2 Hz), 5.16 (1H, br), 7.16 (1H, s), 7.90 (1H, br)

EXAMPLE 3

7β-[(Z)-2-(5-Amino-1,2,4-thiadiazol-3-yl)-2-(1-carboxy-1-methylethoxyimino)acetamido]-3-[7-(3-aminopropionamido)-2,3-dihydro-5-(1H-imidazo[1,2-b]pyrazolio)]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 7-[3-(tert-butoxycarbonylamino)propionyl]amino-2,3-dihydro-1H-imidazo[1,2-b]pyrazole in the same manner as in Example 1 as an amorphous solid.

¹H-NMR(D₂O) δ 1.51 (3H, s), 1.52 (3H, s), 2.83 (2H, t, J=6.4 Hz), 3.26 (1H, d, J=17.9 Hz), 3.53 (1H, d, J=17.9 Hz), 3.31 (2H, t, J=6.4 Hz), 4.15 (2H, t, J=8.7 Hz), 4.33 (1H, q, J=8.7 Hz), 4.42 (1H, q, J=8.7 Hz), 4.95 (1H, d, J=15.1 Hz), 5.03 (1H, d, J=15.1 Hz), 5.25 (1H, d, J=5.0 Hz), 5.84 (1H, d, J=5.0 Hz), 8.06 (1H, s)

Preparation 11 tert-Butyl [2-(5-amino-1-methyl-1H-pyrazol-4-ylcarbamoyl)ethyl]carbamate

The title compound was obtained from 4,5-diamino-1-methylpyrazole sulfuric acid salt and N-[3-(tert-butoxycarbonylamino)propionyloxy]succinimide in the same manner as in Preparation 10.

¹H-NMR(DMSO-d₆) δ 1.38 (9H, s), 2.35 (2H, t, J=7.1 Hz), 3.18 (2H, q, J=7.1 Hz), 3.50 (3H, s), 4.90 (2H, s), 6.83 (1H, t, J=7.1 Hz), 7.14 (1H, s), 9.06 (1H, s)

AP-MS: m/z=283

Preparation 12 tert-Butyl {2-[1-methyl-5-(tritylamino)-1H-pyrazol-4-ylcarbamoyl]ethyl}carbamate The title compound was obtained from tert-butyl [2-(5-amino-1-methyl-1H-pyrazol-4-ylcarbamoyl)ethyl]carbamate in the same manner as in Preparation 6.

$^1$H-NMR(DMSO-$d_6$) δ 1.39 (9H, s), 2.08 (2H, t, J=7.1 Hz), 2.71 (3H, s), 3.04 (2H, q, J=7.1 Hz), 5.57 (1H, s), 6.72 (1H, t, J=7.1 Hz), 7.1–7.4 (16H, m), 8.25 (1H, s)

EXAMPLE 4

7β-[(Z)-2-(5-Amino-1,2,4-thiadiazol-3-yl)-2-(1-carboxy-1-methylethoxyimino)acetamido]-3-[3-amino-4-(3-aminopropionamido)-2-methyl-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and tert-butyl {2-([1-methyl-5-(tritylamino)-1H-pyrazol-4-ylcarbamoyl]ethyl}carbamate in the same manner as in Example 1.

$^1$H-NMR(D$_2$O) δ 1.53 (6H, s), 2.89 (2H, t, J=6.5 Hz), 3.20 and 3.47 (2H, ABq, J=18 Hz), 3.34 (2H, t, J=6.5 Hz), 3.75 (3H, s), 4.99 and 5.21 (2H, ABq, J=16 Hz), 5.25 (1H, d, J=4.8 Hz), 5.85 (1H, d, J=4.8 Hz), 8.02 (1H, s)

ESI-MS: m/z=674(M+Na)

Preparation 13

To a solution of 1,3-bis(tert-butoxycarbonyl)-2-(trifluoromethylsulfonyl)guanidine (22.3 g) in dichloromethane (100 ml) were added 4,5-diamino-1-methylpyrazole sulfuric acid salt (10 g) and triethylamine (33.2 ml) at 4° C., and the mixture was stirred at room temperature overnight. The reaction mixture was poured into a mixture of ethyl acetate and water. The aqueous layer was separated, and the organic layer was washed with brine, dried over anhydrous magnesium sulfate and filtered. The filtrate was concentrated in vacuo. The concentrate was poured into acetonitrile, and the resulting precipitate was collected by filtration and dried in vacuo to give 5-amino-4-[2',3'-bis(tert-butoxycarbonyl)guanidino]-1-methylpyrazole (11.62 g).

$^1$H-NMR(DMSO-$d_6$) δ 1.37 (9H, s), 1.50 (9H, s), 3.52 (3H, s), 5.14 (2H, s), 7.11 (1H, s), 9.14 (1H, s), 11.5 (1H, s)

ESI-MS: m/z=353(M−H)

Preparation 14

4-[2',3'-Bis(tert-butoxycarbonyl)guanidino]-1-methyl-5-(tritylamino)pyrazole The title compound was obtained from 5-amino-4-[2',3'-bis(tert-butoxycarbonyl)guanidino]-1-methylpyrazole in the same manner as in Preparation 6.

$^1$H-NMR(DMSO-$d_6$) δ 1.37 (9H, s), 1.50 (9H, s), 2.85 (3H, s), 5.88 (1H, s), 7.17 (1H, s), 7.21 (15H, m), 8.85 (1H, s), 11.2 (1H, s)

ESI-MS: m/z=597(M+H)

EXAMPLE 5

7β-[(Z)-2-(5-Amino-1,2,4-thiadiazol-3-yl)-2-(1-carboxy-1-methylethoxyimino)acetamido]-3-(3-amino-4-guanidino-2-methyl-1-pyrazolio)methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and 4-[2',3'-bis(tert-butoxycarbonyl)guanidino]-1-methyl-5-(tritylamino)pyrazole in the same manner as in Example 1.

$^1$H-NMR(DMSO-$d_6$) δ 1.53 (6H, s), 3.25 and 3.57 (2H, ABq, J=18 Hz), 3.75 (3H, s), 5.00 and 5.18 (2H, ABq, J=15 Hz), 5.27 (1H, d, J=4.9 Hz), 5.85 (1H, d, J=4.9 Hz), 8.05 (1H, s)

Preparation 15

To a suspension of 4,5-diamino-1-methylpyrazole sulfuric acid salt (305 g) in tetrahydrofuran (3.05 L) was added tert-butyl 2-[(2,5-dioxo-1-pyrrolidinyl)oxyl]-2-oxoethylcarbamate (415 g) under ice-cooling. To the mixture was added diisopropylethylamine (556 ml) dropwise at a temperature below 10° C. The mixture was stirred at room temperature overnight. To the resulting solution were added brine and saturated aqueous sodium hydrogen carbonate solution, and the mixture was extracted with ethyl acetate (3.0 L). The aqueous layer was extracted with tetrahydrofuran/ethyl acetate=1/1 (3.0 L) twice. The organic layer was dried over anhydrous magnesium sulfate, filtered and concentrated in vacuo. The residue was triturated with diisopropyl ether (1.0 L) and dried in vacuo to give tert-butyl 2-[(5-amino-1-methyl-1H-pyrazol-4-yl)amino]-2-oxoethylcarbamate (307 g).

IR(KBr) 3440, 3349, 1670, 1631, 1525, 1276, 1163, 1074, 1014, 860, 791 cm$^{-1}$ $^1$H-NMR(DMSO-$d_6$) δ 1.39 (9H, s), 3.44 (3H, s), 3.64 (2H, d, J=5.9 Hz), 4.91 (2H, brs), 6.97 (1H, t, J=5.9 Hz), 7.15 (1H, s), 9.09 (1H, brs)

Preparation 16

To a solution of tert-butyl 2-[(5-amino-1-methyl-1H-pyrazol-4-yl)amino]-2-oxoethylcarbamate (307 g) in N,N-dimethylformamide (1.5 L) was added triphenylmethyl chloride (334 g). To the mixture was added triethylamine (318 ml) dropwise. The mixture was stirred at room temperature for 1 hour. The reaction mixture was dissolved in ethyl acetate. The solution was washed successively with water, 10% aqueous citric acid solution, water and brine. The extract was dried over anhydrous magnesium sulfate, filtered and concentrated in vacuo. The residue was triturated with acetonitrile (1.5 L) and dried in vacuo to give tert-butyl 2-{[1-methyl-5-(tritylamino)-1H-pyrazol-4-yl]amino}-2-oxoethylcarbamate (468 g).

IR(KBr) 3336, 3280, 1724, 1683, 1599, 1234, 939, 704 cm$^{-1}$ $^1$H-NMR(DMSO-$d_6$) δ 1.38 (9H, s), 2.73 (3H, s), 3.38 (2H, d, J=5.8 Hz), 5.58 (1H, s), 6.94 (1H, t, J=5.8 Hz), 7.11–7.35 (15H, m), 7.21 (1H, s), 8.31 (1H, s)

ESI-MS: m/z=512.3(M+H$^+$)

EXAMPLE 6

To a solution of benzhydryl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (489 g) in N,N-dimethylformamide (1.4 L) was added sodium iodide (102 g). After stirring at room temperature for 1 hour, tert-butyl 2-{[1-methyl-5-(tritylamino)-1H-pyrazol-4-yl]amino}-2-oxoethylcarbamate (383 g) was added to the mixture. Stirring was continued at 37° C. for 24 hours. The resulting mixture was poured into water and extracted with ethyl acetate. The organic layer was washed successively with water, 10% aqueous sodium thiosulfate solution, brine and 10% aqueous sodium trifluoroacetate solution, dried over magnesium sulfate, filtered and evaporated in vacuo. The residue was dissolved in ethyl acetate (3.5 L), and the solution was dropwise added to diisopropyl ether (36 L). The precipitate was collected by filtration. The filter cake was washed with diisopropyl ether and dried in vacuo.

The obtained solid (700 g) was dissolved in dichloromethane (1.4 L), and to the solution were added anisole (700 ml) and trifluoroacetic acid (2.1 L) successively. After stirring at room temperature for 4 hours, the reaction mixture was poured into diisopropyl ether (30 L). The precipitate was collected by filtration. The obtained solid was washed with diisopropyl ether and dried in vacuo. The crude product was dissolved in water (3.5 L), and the pH of the solution was adjusted to 7.0 with 28% aqueous ammonia solution. The insoluble material was filtered off, and the pH of the filtrate was adjusted to 1 with concentrated hydrochloric acid. The insoluble material was filtered off again. The filtrate was chromatographed on Diaion® HP-20 eluting with 20% aqueous 2-propanol. The eluate was concentrated to about 3.0 L in vacuo, and 2.0M sulfuric acid (102 ml) was added to the concentrate. The mixture was lyophilized to give the crude product.

The crude product was purified by preparative HPLC (pH 7.0 phosphate buffer and acetonitrile), and the eluate containing a desired product was concentrated to about 6 L in vacuo. The concentrate was adjusted to about pH 1 with concentrated hydrochloric acid and chromatographed on Diaion® HP-20 eluting with 20% aqueous 2-propanol. The eluate was concentrated to about 550 ml in vacuo, and 2.0M sulfuric acid (54.5 ml) was added to the concentrate. To the mixture was added dropwise acetonitrile (880 ml), and the mixture was stirred at room temperature overnight. To the mixture was added acetonitrile (200 ml), and the mixture was stirred at room temperature for 2 hours. The resulting white crystals were collected by filtration, washed with 25% aqueous acetonitrile and dried under reduced pressure to give 7β-[(Z)-2-(5-amino-1,2,4-thiadiazol-3-yl)-2-(1-carboxy-1-methylethoxyimino)acetamido]-3-[3-amino-4-(aminoacetyl)amino-2-methyl-1-pyrazolio]methyl-3-cephem-4-carboxylic acid hydrogen sulfate (72.5 g).

IR(KBr) 1778, 1700, 1653, 1525, 1149, 1111, 617 cm$^{-1}$ $^1$H-NMR(D$_2$O) δ 1.61 (6H, s), 3.22 and 3.45 (2H, ABq, J=17.8 Hz), 3.73 (3H, s), 4.03 (2H, s), 5.05 and 5.27 (2H, ABq, J=15.8 Hz), 5.25 (1H, d, J=4.8 Hz), 5.87 (1H, d, J=4.8 Hz), 8.09 (1H, s)

ESI-MS: m/z=638.2(M+H$^+$)

EXAMPLE 7

A solution of 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate (36 g) in water was purified by preparative HPLC utilizing ODS column. The eluate containing a desired product was concentrated to about 1.5 L in vacuo. The concentrate was adjusted to about pH 1 with concentrated hydrochloric acid and chromatographed on Diaion® HP-20 (6 L) eluting with 20% aqueous 2-propanol. The eluate was concentrated to about 800 ml in vacuo, and 2M sulfuric acid (17 ml) was added. The resulting solution was lyophilized to give a sulfuric acid salt as an amorphous powder (23.6 g).

The powder was dissolved in water (71 ml) and ethanol (57 ml). After addition of seed crystals (310 mg), which resulted in the precipitation of white solid, the mixture was stirred for 1 hour. A mixture of ethanol (47 ml) and water (37 ml) was added over 30 minutes, and ethanol (33 ml) was added over 20 minutes. Then the slurry was stirred for an additional 1.5 hour. The precipitate was collected by filtration, washed with ethanol/water (60 ml/20 ml) and ethanol (60 ml) and dried to give 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate as crystals (17.3 g)

IR(KBr) 3353, 3183, 1778, 1652, 1558, 1403, 1321, 1143, 1118, 997, 619 cm$^{-1}$ $^1$H-NMR(D$_2$O) δ 1.61 (6H, s), 3.10–3.55 (6H, m), 3.71 (3H, s), 5.02 and 5.23 (2H, ABq, J=16.7 Hz), 5.25 (1H, d, J=4.9 Hz), 5.87 (1H, d, J=4.9 Hz), 7.91 (1H, s)

ESI-MS: m/z=667(M+H$^+$)

X-ray powder diffraction analysis (by Rigaku X-ray Diffraction system MultiFlex)

| 2θ | intensity |
|---|---|
| 8.0 | 1286 |
| 12.7 | 586 |
| 13.8 | 423 |
| 16.1 | 618 |
| 18.9 | 520 |
| 20.4 | 748 |
| 21.5 | 667 |
| 22.4 | 1058 |
| 23.3 | 944 |
| 24.0 | 618 |
| 25.5 | 813 |
| 26.7 | 472 |
| 27.9 | 537 |
| 28.5 | 455 |
| 31.3 | 390 |

X-ray: Cu/40 kV/30 mA

Preparation 17

5-Amino-1-ethyl-4-nitrosopyrazole

The title compound was obtained from 5-amino-1-ethylpyrazole in the same manner as in Preparation 3.

$^1$H-NMR(DMSO-d$_6$) δ 1.21 (3H, t, J=7.1 Hz), 3.93 (2H, q, J=7.1 Hz), 7.04 and 8.53 (1H, s), 8.10 and 8.15 (1H, brs)

APCI-MS: m/z=141(M+H)$^+$

Preparation 18

4,5-Diamino-1-ethylpyrazole sulfuric acid salt

The title compound was obtained from 5-amino-1-ethyl-4-nitrosopyrazole in the same manner as in Preparation 4.

$^1$H-NMR(D$_2$O) δ 1.36 (3H, t, J=7.3 Hz), 4.10 (2H, q, J=7.3 Hz), 7.77 (1H, s)

ESI-MS: m/z=127(M+H)$^+$

Preparation 19

5-Amino-4-[3-(tert-butoxycarbonylamino)propionylamino]-1-ethylpyrazole

The title compound was obtained from 4,5-diamino-1-ethylpyrazole sulfuric acid salt in the same manner as in Preparation 15.

$^1$H-NMR (DMSO-d$_6$) δ 1.24 (3H, t, J=7.2 Hz), 1.37 (9H, s), 2.35 (2H, t, J=7.1 Hz), 3.18 (2H, dt, J=7.1, 7.1 Hz), 3.85 (q, J=7.2 Hz), 4.88 (2H, brs), 6.75–6.90 (1H, m), 7.17 (1H, s), 9.05 (1H, brs)

APCI-MS: m/z=298(M+H)$^+$

Preparation 20

4-[3-(tert-Butoxycarbonylamino)propionylamino]-1-ethyl-5-triphenylmethylaminopyrazole The title compound was obtained from 5-amino-4-[3-(tert-butoxycarbonylamino)propionylamino]-1-ethylpyrazole in the same manner as in Preparation 16.

$^1$H-NMR(DMSO-d$_6$) δ 0.88 (3H, t, J=7.2 Hz), 1.39 (9H, s), 2.02 (2H, t, J=7.1 Hz), 2.95–3.20 (4H, m), 5.59 (1H, brs), 6.60–6.75 (1H, m), 7.10–7.35 (16H, m), 8.04 (1H, brs)

ESI-MS: m/z=540(M+H)$^+$, 562(M+Na)$^+$

EXAMPLE 8

7β-[(Z)-2-(5-Amino-1,2,4-thiadiazol-3-yl)-2-(1-carboxy-1-methylethoxyimino)acetamido]-3-[3-amino-4-(3-aminopropionylamino)-2-ethyl-1-pyrazolio]methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and 4-[3-(tert-butoxycarbonylamino)propionylamino]-1-ethyl-5-triphenylmethylaminopyrazole in the same manner as in Example 1.

IR(KBr) 3415, 1763, 1658, 1598, 1529, 1402, 1361 cm$^{-1}$ $^1$H-NMR(D$_2$O) δ 1.33 (3H, t, J=7.2 Hz), 1.53 (6H, s), 2.89 (2H, t, J=6.5 Hz), 3.17 and 3.49 (2H, ABq, J=17.7 Hz), 3.34 (2H, t, J=6.5 Hz), 4.28 (2H, q, J=7.2 Hz), 5.05 and 5.16 (2H, ABq, J=15.4 Hz), 5.26 (1H, d, J=4.8 Hz), 5.85 (1H, d, J=4.8 Hz) 8.03 (1H, s)

Preparation 21 tert-Butyl 2-[(5-amino-1-ethyl-1H-pyrazol-4-yl)amino]-2-oxoethylcarbamate

The title compound was obtained from 4,5-diamino-1-ethylpyrazole sulfuric acid salt in the same manner as in Preparation 15.

$^1$H-NMR(DMSO-d$_6$) δ 1.21 (3H, t, J=7.2 Hz), 1.39 (9H, s), 3.64 (2H, d, J=6.0 Hz), 3.86 (2H, d, J=7.2 Hz), 4.88 (2H, brs), 6.90–7.00 (1H, m), 7.17 (1H, s), 9.06 (1H, brs)

ESI-MS: m/z=284(M+H)$^+$, 306(M+Na)$^+$

Preparation 22 tert-Butyl 2-{[1-ethyl-5-(tritylamino)-1H-pyrazol-4-yl]amino}-2-oxoethylcarbamate The title compound was obtained from tert-butyl 2-[(5-amino-1-ethyl-1H-pyrazol-4-yl)amino]-2-oxoethylcarbamate in the same manner as in Preparation 16.

$^1$H-NMR(DMSO-d6) δ 0.88 (3H, t, J=7.2 Hz), 1.38 (9H, s), 3.16 (2H, q, J=7.2 Hz), 3.31 (2H, d), 5.59 (1H, brs), 6.80–6.95 (1H, m), 7.10–7.40 (16H, m), 8.03 (1H, brs)

ESI-MS: m/z=526(M+H)$^+$, 548(M+Na)$^+$

EXAMPLE 9

7β-[(Z)-2-(5-Amino-1,2,4-thiadiazol-3-yl)-2-(1-carboxy-1-methylethoxyimino)acetamido]-3-[3-amino-4-(aminoacetyl)amino-2-ethyl-1-pyrazolio]methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and tert-butyl 2-{[1-ethyl-5-(tritylamino)-1H-pyrazol-4-yl]amino}-2-oxoethylcarbamate in the same manner as in Example 1.

IR(KBr) 3444, 1761, 1635, 1626, 1446, 1406 cm$^{-1}$ $^1$H-NMR(D$_2$O) δ 1.33 (3H, t, J=7.2 Hz), 1.53 (6H, s), 2.89 (2H, t, J=6.5 Hz), 3.17 and 3.49 (2H, ABq, J=17.7 Hz), 4.00 (2H, s), 4.28 (2H, q, J=7.2 Hz), 5.06 and 5.17 (2H, ABq, J=15.4 Hz), 5.27 (1H, d, J=4.8 Hz), 5.85 (1H, d, J=4.8 Hz), 8.07 (1H, s)

Preparation 23

5-Amino-4-[2',3'-bis(tert-butoxycarbonyl)guanidino]-1-ethylpyrazole

The title compound was obtained from 1,3-bis(tert-butoxycarbonyl)-2-(trifluoromethylsulfonyl)guanidine and 4,5-diamino-1-ethylpyrazole sulfuric acid salt in the same manner as in Preparation 13.

$^1$H-NMR(DMSO-d$_6$) δ 1.22 (3H, t, J=7.1 Hz), 1.37 (9H, s), 1.50 (9H, s), 3.88 (2H, d, J=7.1 Hz), 5.12 (2H, brs), 7.14 (1H, s), 9.16 (1H, brs), 11.51 (1H, brs)

ESI-MS: m/z=369(M+H)$^+$

Preparation 24

4-[2',3'-Bis(tert-butoxycarbonyl)guanidino]-1-ethyl-5-triphenylmethylaminopyrazole The title compound was obtained from 5-amino-4-[2',3'-bis(tert-butoxycarbonyl)guanidino]-1-ethylpyrazole in the same manner as in Preparation 16.

$^1$H-NMR(DMSO-d$_6$) δ 0.86 (3H, t, J=7.1 Hz), 1.38 (9H, s), 1.49 (9H, s), 5.85 (1H, brs), 7.10–7.30 (16H, m), 8.80 (1H, brs), 11.14 (1H, brs)

ESI-MS: m/z=611(M+H)$^+$, 633(M+Na)$^+$

EXAMPLE 10

7β-[(Z)-2-(5-Amino-1,2,4-thiadiazol-3-yl)-2-(1-carboxy-1-methylethoxyimino)acetamido]-3-[3-amino-2-ethyl-4-guanidino-1-pyrazolio]methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and 4-[2',3'-bis(tert-butoxycarbonyl)guanidino]-1-ethyl-5-triphenylmethylaminopyrazole in the same manner as in Example 1.

IR(KBr) 3437, 1760, 1658, 1625, 1406, 1065 cm$^{-1}$
$^1$H-NMR(D$_2$O) δ 1.35 (3H, t, J=7.3 Hz), 1.53 (6H, s), 3.26 and 3.61 (2H, ABq, J=17.8 Hz), 4.29 (2H, q, J=7.3 Hz), 5.06 and 5.17 (2H, ABq, J=15.7 Hz), 5.29 (1H, d, J=4.8 Hz), 5.85 (1H, d, J=4.8 Hz), 8.06 (1H, s)

EXAMPLE 11

To a suspension of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (500 g) in N,N-dimethylformamide (2.5 L) was added 4-[2',3'-bis(tert-butoxycarbonyl)guanidino]-1-methyl-5-triphenylmethylaminopyrazole (419 g) and the mixture was stirred at room temperature for 16 hours. The reaction mixture was added to a mixture of ethyl acetate and water. The organic layer was washed with water, brine and 10% aqueous sodium trifluoroacetate solution and then dried over magnesium sulfate. The magnesium sulfate was filtered off, and the filtrate was evaporated to 3.3 kg under reduced pressure. The concentrate was poured into diisopropyl ether (33 L), and the resulting precipitate was collected by filtration and dried in vacuo.

To a solution of the resulting solid in methylene chloride (1500 ml) were added anisole (500 ml) and trifluoroacetic acid (1500 ml) The resulting solution was stirred at room temperature for 4 hours and poured into diisopropyl ether. The resulting precipitate was collected by filtration and dried in vacuo. The crude product was dissolved in water (3.5 L), and the pH of the solution was adjusted to 7.0 with 28% aqueous ammonia solution. The insoluble material was filtered off, and the pH of the filtrate was adjusted to 1 with concentrated hydrochloric acid. The insoluble material was filtered off, again. The filtrate was chromatographed on Diaion® HP-20 eluting with 20% aqueous 2-propanol. The eluate was concentrated to about 3.0 L in vacuo. To the concentrate was added 2.0M sulfuric acid (150 ml), and the mixture was lyophilized to give the crude product. The crude product was purified with preparative HPLC utilizing ODS column (pH 7.0 phosphate buffer and acetonitrile). The eluate containing a desired product was concentrated to about 6 L in vacuo. The concentrate was adjusted to about pH 1 with concentrated hydrochloric acid and chromatographed on Diaion® HP-20 eluting with 20% aqueous 2-propanol. The eluate was concentrated to about 1.5 L in vacuo. To the concentrate was added 2.0M sulfuric acid (60 ml), and the mixture was lyophilized to give 7β-[(Z)-2-(5-amino-1,2,4-thiadiazol-3-yl)-2-(1-carboxy-1-methylethoxyimino)acetamido]-3-(3-amino-4-guanidino-2-methyl-1-pyrazolio)methyl-3-cephem-4-carboxylic acid hydrogen sulfate (48.5 g).

IR(KBr) 1776, 1714, 1677, 1651, 1402, 1112 cm$^{-1}$
$^1$H-NMR(D$_2$O) δ 1.61 (6H, s), 3.28 and 3.58 (2H, ABq, J=17.8 Hz), 3.74 (3H, s), 5.15 and 5.23 (2H, ABq, J=15.7 Hz), 5.27 (1H, d, J=4.8 Hz), 5.88 (1H, d, J=4.8 Hz), 8.07 (1H, s)
ESI-MS: m/z=623.2(M+H$^+$)

Preparation 25

To a suspension of 4,5-diamino-1-(2-hydroxyethyl)pyrazole sulfuric acid salt (2.4 g) in methylene chloride (40 ml) were added N-ethyldiisopropylamine (2.1ml) and N-[3-(tert-butoxycarbonylamino)propionyloxy]succinimide (2.3 g) under ice-cooling, and the mixture was stirred at room temperature for 6 hours. To the reaction mixture were added brine (40 ml) and saturated aqueous sodium hydrogen carbonate solution (20 ml), and the mixture was extracted with a mixture of ethyl acetate and 2-propanol, (3:1, 60 ml). The organic layer was dried over anhydrous sodium sulfate, filtered and concentrated in vacuo. The residue was triturated with diethyl ether to give 5-amino-4-[3-(tert-butoxycarbonylamino)propionyl]amino-1-(2-hydroxyethyl)pyrazole (1.65 g) as a solid.

$^1$H-NMR(DMSO-d$_6$) δ 1.38 (9H, s), 2.35 (2H, t, J=7.3 Hz), 3.16–3.20 (2H, m), 3.62–3.65 (2H, m), 3.90 (2H, t, J=6.0 Hz), 4.85 (2H, brs), 4.92 (1H, t, J=5.0 Hz), 6.84 (1H, t, J=5.5 Hz), 7.20 (1H, s), 9.09 (1H, brs)

EXAMPLE 12

7β-[(Z)-2-(5-Amino-1,2,4-thiadiazol-3-yl)-2-(1-carboxy-1-methylethoxyimino)acetamido]-3-[3-amino-4(3-aminopropionamido)-2-(2-hydroxyethyl)-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 5-amino-4-[3-(tert-butoxycarbonylamino)propionyl]amino-1-(2-hydroxyethyl)pyrazole in the same manner as in Example 1 as an amorphous solid.

$^1$H-NMR(D$_2$O) δ 1.51 (6H, s), 2.88 (2H, t, J=6.4 Hz), 3.15 (1H, d, J=17.9 Hz), 3.48 (1H, d, J=17.9 Hz), 3.32 (2H, t, J=6.4 Hz), 3.88 (2H, t, J=4.8 Hz), 4.39 (1H, dt, J=16.5 Hz, 4.8 Hz), 4.42 (1H, dt, J=16.5, 4.8 Hz), 5.06 (1H, d, J=15.1 Hz), 5.11 (1H, d, J=15.1 Hz), 5.25 (1H, d, J=5.0 Hz), 5.83 (1H, d, J=5.0 Hz), 8.05 (1H, s)

Preparation 26

To a solution of 4-formyl-4,5,6,7-tetrahydropyrazolo[1,5-a]pyrimidine (1.51 g) in sulfuric acid (7.5 ml) was added potassium nitrate (111 g) under ice-cooling. The mixture was stirred at room temperature for 17 hours. The reaction mixture was added to ice (100 g). The crystalline residue was collected by filtration and dried in vacuo to give 3-nitro-4,5,6,7-tetrahydropyrazolo[1,5-a]pyrimidine (0.63 g) as a solid.

$^1$H-NMR(DMSO-d$_6$) δ 2.00–2.05 (2H, m), 3.30–3.36 (2H, m), 3.99 (2H, t, J=6.0 Hz), 7.85 (1H, s), 7.89 (1H, s)

Preparation 27

A solution of 3-nitro-4,5,6,7-tetrahydropyrazolo[1,5-a]pyrimidine (1.68 g) in a mixture of sulfuric acid (0.6 ml), acetic acid (100 ml) and water (10 ml) was treated with 10% palladium on carbon (0.5 g) under a hydrogen atmosphere at room temperature for 6 days. After the catalyst was filtered off, the filtrate was concentrated in vacuo. The residue was triturated with ethanol and dried in vacuo to give 3-amino-4,5,6,7-tetrahydropyrazolo[1,5-a]pyrimidine sulfuric acid salt (2.3 g) as a solid.

$^1$H-NMR(DMSO-d$_6$) δ 1.97–2.01 (2H, m), 3.22 (2H, t, J=5.0 Hz), 3.98 (2H, t, J=6.0 Hz), 7.22 (1H, s)

Preparation 28

To a solution of 3-amino-4,5,6,7-tetrahydropyrazolo[1,5-a]pyrimidine sulfuric acid salt (2.96 g) and N-ethyldiisopropylamine (3.88 g) in methylene chloride (70 ml) was added 1,3-bis(tert-butoxycarbonyl)-2-(trifluoromethanesulfonyl) guanidine (3.91 g). The mixture was stirred at room temperature for 150 minutes. There action mixture was washed with saturated aqueous sodium hydrogen carbonate solution. The organic layer was dried over anhydrous magnesium sulfate, filtered and concentrated in vacuo. The residue was purified by column chromatography on silica gel eluting with 2% methanol/chloroform to give 3-[2,3-bis(tert-butoxycarbonyl)guanidino]-4,5,6,7-tetrahydropyrazolo[1,5-a]pyrimidine (3.4 g) as a solid.

$^1$H-NMR(CDCl$_3$) δ 1.48 (9H, s), 1.52 (9H, s), 2.12–2.14 (2H, m), 3.33–3.37 (2H, m), 4.08 (2H, t, J=6.0 Hz), 6.17 (1H, brs), 7.16 (1H, s), 9.87 (1H, brs), 11.39 (1H, brs)

EXAMPLE 13

To a solution of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1.0 g) in N,N-dimethylformamide (2.0 ml) was added sodium iodide (181 mg), and the mixture was stirred at room temperature for 30 minutes. To the reaction mixture were added 3-[2,3-bis(tert-butoxycarbonyl) guanidino]-4,5,6,7-tetrahydropyrazolo[1,5-a]pyrimidine (571 mg) and methylene chloride (2.0 ml). The whole mixture was stirred at room temperature for 7 hours. To the reaction mixture were added ethyl acetate (100 ml) and water (50 ml). The aqueous layer was separated, and the organic layer was washed with 10% aqueous sodium trifluoroacetate solution and brine, dried over sodium sulfate and filtered. The filtrate was concentrated to about 5 ml in vacuo. The concentrate was poured into diisopropyl ether (150 ml), and the resulting precipitate was collected by filtration and dried in vacuo.

To a solution of the resulting solid in methylene chloride (3.0 ml) were added anisole (1.0 ml) and trifluoroacetic acid (2.0 ml), and the mixture was stirred at room temperature for 4 hours. The reaction mixture was pouted into diisopropyl ether (150 ml), and the resulting precipitate was collected by filtration and dried in vacuo to give a crude product (570 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-[3-guanidino-4,5,6,7-tetrahydro-1-pyrazolo[1,5-a]pyrimidinio]methyl-3-cephem-4-carboxylate (51 mg) as an amorphous solid.

$^1$H-NMR(D$_2$O) δ 1.52 (3H, s), 1.53 (3H, s), 2.05–2.25 (2H, m), 3.26 (1H, d, J=17.4 Hz), 3.56 (1H, d, J=17.4 Hz), 3.30–3.45 (2H, m), 4.15 (2H, t, J=6.0 Hz), 4.93 (1H, d, J=15.6 Hz), 5.15 (1H, d, J=15.6 Hz), 5.25 (1H, d, J=4.8 Hz), 5.84 (1H, d, J=4.8 Hz), 7.99 (1H, s)

Preparation 29

To a solution of 7-amino-2,3-dihydro-1H-imidazo[1,2-b] pyrazole sulfuric acid salt (4.4 g), 4-(dimethylamino)pyridine (244 mg) and triethylamine (8.10 g) in chloroform (45 ml) was added 1,3-bis(tert-butoxycarbonyl)-2-(trifluoromethanesulfonyl)guanidine (10.18 g). The mixture was stirred at room temperature for 2 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was triturated with diisopropyl ether to give 7-[2,3-bis(tert-butoxycarbonyl)guanidino]-2,3-dihydro-1H-imidazo[1,2-b]pyrazole (4.6 g) as a solid.

$^1$H-NMR(CDCl$_3$) δ 1.49 (9H, s), 1.52 (9H, s), 3.97–4.01 (2H, m), 4.21 (2H, t, J=7.8 Hz), 5.30 (1H, brs), 7.19 (1H, s), 9.86 (1H, brs), 11.32 (1H, brs)

EXAMPLE 14

7β-[(Z)-2-(5-Amino-1,2,4-thiadiazol-3-yl)-2-(1-carboxy-1-methylethoxyimino)acetamido]-3-[7-guanidino-2,3-dihydro-5-(1H-imidazo[1,2-b]pyrazolio)] methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 7-[2,3-bis(tert-butoxycarbonyl)guanidino]-2,3-dihydro-1H-imidazo[1,2-b]pyrazole in the same manner as in Example 13 as an amorphous solid.

$^1$H-NMR(D$_2$O) δ 1.51 (3H, s), 1.52 (3H, s), 3.35 (1H, d, J=17.9 Hz), 3.61 (1H, d, J=17.9 Hz), 4.19 (2H, t, J=8.7 Hz), 4.37 (1H, q, J=8.7 Hz), 4.47 (1H, q, J=8.7 Hz), 5.00 (1H, d, J=15.1 Hz), 5.04 (1H, d, J=15.1 Hz), 5.26 (1H, d, J=4.8 Hz), 5.84 (1H, d, J=4.8 Hz), 8.13 (1H, s)

Preparation 30

To a solution of 5-amino-1-(2-hydroxyethyl)pyrazole (6.35 g) in a mixed solvent of ethanol (25 ml) and concentrated hydrochloric acid (0.035 ml) was added dropwise isoamyl nitrite (7.03 g). The mixture was stirred at room temperature for 17 hours. The crystalline residue was collected by filtration and dried in vacuo to give 5-amino-1-(2-hydroxyethyl)-4-nitrosopyrazole (4.0 g) as a solid.

$^1$H-NMR(DMSO-d$_6$) δ 3.68 (2H, t, J=5.5 Hz), 3.94 (2H, t, J=5.5 Hz), 4.89 (1H, br), 8.06 (2H, br), 8.53 (1H, s)

Preparation 31

A solution of 5-amino-1-(2-hydroxyethyl)-4-nitrosopyrazole (97 g) in a mixed solvent of sulfuric acid (34 ml) and water (2000 ml) was treated with 10% palladium on carbon (10 g) under a hydrogen atmosphere at room temperature for 4 days. After the catalyst was filtered off, the filtrate was concentrated in vacuo. The residue was triturated with methanol and dried in vacuo to give 4,5-diamino-1-(2-hydroxyethyl)pyrazole sulfuric acid salt (90.2 g) as a solid.

¹H-NMR(DMSO-d₆) δ 3.66 (2H, t, J=5.5 Hz), 3.95 (2H, t, J=5.5 Hz), 7.25 (1H, s)

Preparation 32

To a suspension of 4,5-diamino-1-(2-hydroxyethyl)pyrazole sulfuric acid salt (50.0 g) in chloroform (500 ml) were added 4-(dimethylamino)pyridine (2.54 g), triethylamine (116 ml) and 1,3-bis(tert-butoxycarbonyl)-2-(trifluoromethanesulfonyl)guanidine (106 g). The mixture was stirred under reflux for 2 hours. After cooling on an ice bath, the reaction mixture was washed successively with water, 4% aqueous citric acid solution, water and aqueous sodium hydrogen carbonate solution. The organic layer was dried over sodium sulfate, filtered and concentrated in vacuo. The residue was triturated with a mixed solvent of ethyl acetate (50 ml) and diethyl ether (200 ml) to give 5-amino-4-[2,3-bis(tert-butoxycarbonyl)guanidino]-1-(2-hydroxyethyl)pyrazole (50 g) as a solid.

¹H-NMR(CDCl₃) δ 1.47 (9H, s), 1.53 (9H, s), 3.28 (1H, br), 4.02–4.05 (4H, m), 4.65 (2H, br), 7.22 (1H, s), 9.85 (1H, br), 11.55 (1H, br)

EXAMPLE 15

7β-[(Z)-2-(5-Amino-1,2,4-thiadiazol-3-yl)-2-(1-carboxy-1-methylethoxyimino)acetamido]-3-[3-amino-4-guanidino-2-(2-hydroxyethyl)-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 5-amino-4-[2,3-bis(tert-butoxycarbonyl)guanidino]-1-(2-hydroxyethyl)pyrazole in the same manner as in Example 13 as an amorphous solid.

¹H-NMR(D₂O) δ 1.52 (3H, s), 3.21 (1H, d, J=17.9 Hz), 3.59 (1H, d, J=17.9 Hz), 3.90 (2H, t, J=4.8 Hz), 4.35–4.50 (2H, m), 5.07 (1H, d, J=14.9 Hz), 5.11 (1H, d, J=14.9 Hz), 5.28 (1H, d, J=5.0 Hz), 5.84 (1H, d, J=5.0 Hz), 8.09 (1H, s)

Preparation 33

To a solution of 7-[2,3-bis(tert-butoxycarbonyl)guanidino]-2,3-dihydro-1H-imidazo[1,2-b]pyrazole (1.83 g) in pyridine (10 ml) was added triphenylmethyl chloride (1.67 g). The mixture was stirred at 50° C. for 5 hours. After cooling, chloroform (50 ml) was added to the reaction mixture, and the mixture was washed successively with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 2% methanol/chloroform to give 7-[-2,3-bis(tert-butoxycarbonyl)guanidino]-1-triphenylmethyl-2,3-dihydro-1H-imidazo[1,2-b]pyrazole (1.57 g) as a solid.

¹H-NMR(CDCl₃) δ 1.47 (9H, s), 1.48 (9H, s), 3.50 (2H, t, J=7.8 Hz), 3.92 (2H, t, J=7.8 Hz), 7.07–7.26 (10H, m), 7.53–7.54 (6H, m), 8.34 (1H, brs), 11.12 (1H, brs)

EXAMPLE 16

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (819 mg) in N,N-dimethylformamide (2.4 ml) was added N-(trimethylsilyl)acetamide (656 mg), and the mixture was stirred at room temperature for 30 minutes. To the reaction mixture was added 7-[2,3-bis(tert-butoxycatbonyl)guanidino]-1-triphenylmethyl-2,3-dihydro-1H-imidazo[1,2-b]pyrazole (730 mg). The whole mixture was stirred at room temperature for 6 hours. To the resulting reaction mixture were added ethyl acetate (100 ml) and water (50 ml). The aqueous layer was separated, and the organic layer was washed with 10% aqueous sodium trifluoroacetate solution, 10% aqueous sodium thiosulfate solution and brine, dried over sodium sulfate and filtered. The filtrate was concentrated to about 5 ml in vacuo. The concentrate was poured into diisopropyl ether (120 ml), and the resulting precipitate was collected by filtration and dried in vacuo.

To a solution of the resulting solid in methylene chloride (2.0 ml) were added anisole (0.67 ml) and trifluoroacetic acid (1.34 ml), and the mixture was stirred at room temperature for 4 hours. The reaction mixture was poured into diisopropyl ether (120 ml). The resulting precipitate was collected by filtration and dried in vacuo to give a crude product (430 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-[7-guanidino-2,3-dihydro-5-(1H-imidazo[1,2-b]pyrazolio)]methyl-3-cephem-4-carboxylate (20.4 mg) as an amorphous solid.

¹H-NMR (D₂O) δ 1.51 (3H, s), 1.52 (3H, s), 3.35 (1H, d, J=17.9 Hz), 3.61 (1H, d, J=17.9 Hz), 4.19 (2H, t, J=8.7 Hz), 4.37 (1H, q, J=8.7 Hz), 4.47 (1H, q, J=8.7 Hz), 5.00 (1H, d, J=15.1 Hz), 5.04 (1H, d, J=15.1 Hz), 5.26 (1H, d, J=4.8 Hz), 5.84 (1H, d, J=4.8 Hz), 8.13 (1H, s)

Preparation 34

To a suspension of 1,1'-carbonyldiimidazole (1.94 g) in methylene chloride (20 ml) was added tert-butyl N-(3-aminopropyl)carbamate (2.30 g), and the mixture was stirred at room temperature for 1 hour. To the reaction mixture were added N-ethyldiisopropylamine (2.56 g) and 4,5-diamino-1-methylpyrazole sulfuric acid salt, (2.10 g), and the mixture was stirred at 30° C. for 3 days. The reaction mixture was concentrated in vacuo. The residue was purified by column chromatography on silica gel eluting with 6% methanol/chloroform to give 5-amino-4-(3-{3-[(tert-butoxycarbonyl)amino]propyl}ureido)-1-methylpyrazole (1.75 g) as a solid.

¹H-NMR(DMSO-d₆) δ 1.37 (9H, s), 1.43–1.49 (2H, m), 2.89–2.93 (2H, m), 2.98–3.01 (2H, m), 3.50 (3H, s), 4.79 (2H, br), 5.85 (1H, br), 6.77 (1H, br), 6.96 (1H, s), 7.12 (1H, br)

EXAMPLE 17

To a solution of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1.0 g) in N,N-dimethylformamide (2.0 ml) was added sodium iodide (199 mg), and the mixture was stirred at room temperature for 30 minutes. To the reaction mixture was added 5-amino-4-(3-{3-[(tert-butoxycarbonyl)amino]propy}ureido)-1-methylpyrazole (415 mg)

and the whole mixture was stirred at 32° C. for 24 hours. To the resulting reaction mixture were added ethyl acetate (50 ml) and water (50 ml). The aqueous layer was separated, and the organic layer was washed with 10% aqueous sodium trifluoroacetate solution and brine, dried over anhydrous sodium sulfate and filtered. The filtrate was concentrated to about 5 ml in vacuo. The concentrate was poured into diisopropyl ether (100 ml), and the resulting precipitate was collected by filtration and dried in vacuo. To a solution of the resulting solid in methylene chloride (3.6 ml) were added anisole (1.2 ml) and trifluoroacetic acid (2.4 ml). The resulting solution was stirred at room temperature for 4 hours and poured into diisopropyl ether (100 ml). The resulting precipitate was collected by filtration and dried in vacuo to give a crude product (939 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-{3-amino-4-[3-(3-aminopropyl)ureido]-2-methyl-1-pyrazolio}methyl-3-cephem-4-carboxylate (53 mg) as an amorphous solid.

$^1$H-NMR(D$_2$O) δ 1.52 (3H, s), 1.53 (3H, s), 1.85–1.88 (2H, m), 3.03 (2H, t, J=8 Hz), 3.22(2H, t, J=18 Hz), 3.26 (2H, t, J=7 Hz), 3.49 (1H, d, J=18 Hz), 3.72 (3H, s), 4.96 (1H, d, J=15 Hz), 5.16 (1H, d, J=15 Hz), 5.25 (1H, d, J=5 Hz), 5.84 (1H, d, J=5 Hz), 7.88 (1H, s)

Preparation 35

To a suspension of 1,1'-carbonyldiimidazole (973 mg) in methylene chloride (10 ml) was added tert-butyl N-(2-aminoethyl)carbamate (1.11 g) under ice-cooling, and the mixture was stirred at room temperature for 2 hours. To the reaction mixture were added N-ethyldiisopropylamine (1.28 g) and 3-amino-4,5,6,7-tetrahydropyrazolo[1,5-a]pyrimidine sulfuric acid salt (1.18 g), and the mixture was stirred at 50° C. for 6 hours. The reaction mixture was washed with brine. The organic layer was dried over anhydrous magnesium sulfate, filtered and concentrated in vacuo. The residue was purified by column chromatography on silica gel eluting with 5% methanol/chloroform to give 3-(3-{2-[(tert-butoxycarbonyl)amino]ethyl}ureido)-4,5,6,7-tetrahydropyrazolo[1,5-a]pyrimidine (150 mg) as a solid.

$^1$H-NMR(CDCl$_3$) δ 1.43 (9H, s), 2.11–2.16 (2H, m), 3.22–3.35 (6H, m), 4.09 (2H, t, J=7 Hz), 4.69 (1H, br), 5.14 (2H, br), 5.69 (1H, br), 7.17 (1H, s)

EXAMPLE 18

7β-[(Z)-2-(5-Amino-1,2,4-thiadiazol-3-yl)-2-(1-carboxy-1-methylethoxyimino)acetamido]-3-{3-[3-(2-aminoethyl)ureido]-4,5,6,7-tetrahydro-1-pyrazolo[1,5-a]pyrimidinio}methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 3-(3-(2-[(tert-butoxycarbonyl)aminoethyl]ureido)-4,5,6,7-tetrahydropyrazolo[1,5-a]pyrimidine in the same manner as in Example 17 as an amorphous solid.

$^1$H-NMR(D$_2$O) δ 1.52 (3H, s), 1.53 (3H, s), 2.09–2.21 (2H, m), 3.13 (2H, t, J=6 Hz), 3.24 (1H, d, J=18 Hz), 3.35–3.52 (5H, m), 4.12–4.15 (2H, m), 4.88 (1H, d, J=16 Hz), 5.13 (1H, d, J=16 Hz), 5.25 (1H, d, J=5 Hz), 5.85 (1H, d, J=5 Hz), 7.83 (1H, s)

Preparation 36

To a suspension of 1,1'-carbonyldiimidazole (973 mg) in methylene chloride (10 ml) was added O-[2-(tert-butoxycarbonylamino)ethyl]hydroxylamine (1.11 g) under ice-cooling, and the mixture was stirred at room temperature for 2 hours. To the reaction mixture were added N-ethyldiisopropylamine (1.28 g) and 4,5-diamino-1-methylpyrazole sulfuric acid salt (1.05 g), and the mixture was stirred under reflux for 4 hours. The reaction mixture was washed with brine. The organic layer was dried over anhydrous magnesium sulfate, filtered and concentrated in vacuo. The residue was purified by column chromatography on silica gel eluting with 10% methanol/chloroform to give 5-amino-4-(3-{2-[(tert-butoxycarbonyl)amino]ethoxy}ureido)-1-methylpyrazole (255 mg) as a solid.

$^1$H-NMR(DMSO-d$_6$) δ 1.38 (9H, s), 3.19–3.20 (2H, m), 3.51 (3H, s), 3.72 (2H, t, J=6 Hz), 4.86 (2H, br), 6.95 (1H, br), 7.06 (1H, s), 8.02 (1H, brs), 9.15 (1H, brs)

EXAMPLE 19

7β-[(Z)-2-(5-Amino-1,2,4-thiadiazol-3-yl)-2-(1-carboxy-1-methylethoxyimino)acetamido]-3-{3-amino-4-[3-(2-aminoethoxy)ureido]-2-methyl-1-pyrazolio}methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 5-amino-4-(3-{2-[(tert-butoxycarbonyl)amino]ethoxy}ureido)-1-methylpyrazole in the same manner as in Example 17 as an amorphous solid.

$^1$H-NMR(D$_2$O) δ 1.52 (3H, s), 1.53 (3H, s), 3.21 (1H, d, J=18 Hz), 3.33 (2H, t, J=5 Hz), 3.47 (1H, d, J=18 Hz), 3.74 (3H, s), 4.17 (2H, t, J=5 Hz), 4.99 (1H, d, J=15 Hz), 5.17 (1H, d, J=15 Hz), 5.26 (1H, d, J=5 Hz), 5.86 (1H, d, J=5 Hz), 7.93 (1H, s)

Preparation 37

To a suspension of 1,1'-carbonyldiimidazole (1.95 g) in methylene chloride (20 ml) was added tert-butyl N-(2-aminoethyl)carbamate (1.92 g) under ice-cooling, and the mixture was stirred at room temperature for 2 hours. To the reaction mixture were added N-ethyldiisopropylamine (2.59 g) and 7-amino-2,3-dihydro-1H-imidazo[1,2-b]pyrazole sulfuric acid salt (2.22 g), and the mixture was stirred at room temperature for 16 hours. To the reaction mixture were added trityl chloride (9.0 g) and triethylamine (3.0 g). The mixture was stirred at room temperature for 24 hours. The reaction mixture was washed with 10% aqueous citric acid solution, brine and saturated aqueous sodium hydrogen carbonate solution. The organic layer was dried over anhydrous magnesiumsulfate, filtered and concentrated in vacuo. The residue was purified by column chromatography on silica gel eluting with 3% methanol/chloroform to give 7-(3-{2-[(tert-butoxycarbonyl)amino]ethyl}ureido)-2,3-dihydro-1-tritylimidazo[1,2-b]pyrazole (800 mg) as a solid.

$^1$H-NMR(CDCl$_3$) δ 1.43 (9H, s), 3.19 (4H, br), 3.69 (1H, brs), 3.78–3.85 (4H, m), 4.51 (1H, br), 5.07 (1H, br), 7.20 (N, s), 7.26–7.34 (9H, m), 7.46–7.47 (6H, m)

EXAMPLE 20

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (820 mg) in N,N-dimethylformamide (2.4 ml) was added N-(trimethylsilyl)acetamide (656 mg), and the mixture was stirred at room temperature for 30 minutes. To the reaction mixture was added 7-(3-{2-[(tert-butoxycarbonyl)amino]ethyl}ureido)-2,3-dihydro-1-tritylimidazo[1,2-b]pyrazole (700 mg), and the whole mixture was stirred at room temperature for 6 hours. To the resulting reaction mixture were added ethyl acetate (50 ml) and water (50 ml). The aqueous layer was separated, and the organic layer was washed with 10% aqueous sodium trifluoroacetate solution and brine, dried over anhydrous sodium sulfate and filtered. The filtrate was concentrated to about 5 ml in vacuo. The concentrate was poured into diisopropyl ether (120 ml), and the resulting precipitate was collected by filtration and dried in vacuo. To a solution of the resulting solid in methylene chloride (3.0 ml) were added anisole (1.0 ml) and trifluoroacetic acid (2.0 ml). The resulting solution was stirred at room temperature for 4 hours and poured into diisopropyl ether (120 ml). The resulting precipitate was collected by filtration and dried in vacuo to give a crude product (830 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-{7-[3-(2-aminoethyl)ureido]-2,3-dihydro-5-(1H-imidazo[1,2-b]pyrazolio)}methyl-3-cephem-4-carboxylate (28.5 mg) as an amorphous solid.

$^1$H-NMR(D$_2$O) δ 1.53 (3H, s), 1.54 (3H, s), 3.14 (2H, t, J=6 Hz), 3.29 (1H, d, J=18 Hz), 3.49 (2H, t, J=6 Hz), 3.57 (1H, d, J=18 Hz), 4.16 (2H, t, J=9 Hz), 4.31–4.45 (2H, m), 4.94 (1H, d, J=15 Hz), 5.02 (1H, d, J=15 Hz), 5.27 (1H, d, J=5 Hz), 5.85 (1H, d, J=5 Hz), 7.95 (1H, s)

Preparation 38

To a suspension of 1,1'-carbonyldiimidazole (2.0 g) in dehydrated chloroform (30 ml) was added a solution of tert-butyl N-(2-hydroxyethyl)carbamate (1.92 g) in dehydrated chloroform (10 ml) under ice-cooling, and the mixture was stirred at room temperature for 1 hour. To the reaction mixture were added N-ethyldiisopropylamine (2.2 ml) and 4,5-diamino-1-methylpyrazole sulfuric acid salt (2.58 g), and the mixture was stirred at room temperature for 17.5 hours. To the reaction mixture were added trityl chloride (3.42 g) and triethylamine (1.25 g). The mixture was stirred at room temperature for 2 hours. The reaction mixture was washed with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 5% methanol/chloroform to give 4-{[2-(tert-butoxycarbonylamino)ethoxycarbonyl]amino}-5-(tritylamino)-1-methylpyrazole (1.91 g) as a solid.

$^1$H-NMR(CDCl$_3$) δ 1.46 (9H, s), 2.89 (3H, s), 3.30–3.36 (2H, m), 4.03–4.07 (2H, m), 4.37 (1H, brs), 4.75 (1H, br), 5.42 (1H, br), 7.17–7.30 (16H, m)

EXAMPLE 21

7β-[(Z)-2-(5-Amino-1,2,4-thiadiazol-3-yl)-2-(1-carboxy-1-methylethoxyimino)acetamido]-3-{3-amino-4-[(2-aminoethoxycarbonyl)amino]-2-methyl-1-pyrazolio}methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and 4-{[2-(tert-butoxycarbonylamino)ethoxycarbonyl]amino}-5-(tritylamino)-1-methylpyrazole in the same manner as in Example 20 as an amorphous solid.

$^1$H-NMR (D$_2$O) δ 1.53 (3H, s), 1.54 (3H, s), 3.18 (1H, d, J=18 Hz), 3.30–3.38 (2H, m), 3.43 (1H, d, J=18 Hz), 3.71 (3H, s), 4.37–4.40 (2H, m), 4.97 (1H, d, J=15 Hz), 5.18 (1H, d, J=15 Hz), 5.24 (1H, d, J=5 Hz), 5.83 (1H, d, J=5 Hz), 7.95 (1H, s)

Preparation 39

To a solution of 7-amino-2,3-dihydro-1H-imidazo[1,2-b]pyrazole sulfuric acid salt (1.42 g) and N-ethyldiisopropylamine (2.73 g) in methylene chloride (50 ml) was added N-[2-(tert-butoxycarbonylamino)acetoxy]succinimide (1.90 g). The mixture was stirred at room temperature for 22 hours. The reaction mixture was washed with saturated aqueous sodium hydrogen carbonate solution, and the organic layer was dried over anhydrous magnesium sulfate, filtered and concentrated in vacuo. The oily residue was purified by column chromatography on silica gel eluting with 5% methanol/chloroform to give 7-[2-(tert-butoxycarbonylamino)acetyl]amino-2,3-dihydro-1H-imidazo[1,2-b]pyrazole (1.07 g) as a solid.

$^1$H-NMR(CDCl$_3$) δ 1.47 (9H, s), 3.89 (2H, d, J=5.5 Hz), 3.97 (2H, dt, J=2.7, 7.3 Hz), 4.18 (2H, t, J=7.3 Hz), 4.55 (1H, br), 5.22 (1H, br), 7.16 (1H, s), 7.95 (1H, br)

EXAMPLE 22

To a solution of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1.0 g) in N,N-dimethylformamide (2.0 ml) was added sodium iodide, (181 mg), and the mixture was stirred at room temperature for 30 minutes. To the reaction mixture was added 7-[2-(tert-butoxycarbonylamino)acetyl]amino-2,3-dihydro-1H-imidazo[1,2-b]pyrazole (421 mg). The whole mixture was stirred at 30° C. for 3 hours. To the resulting reaction mixture were added ethyl acetate (100 ml) and water (50 ml). The aqueous layer was separated, and the organic layer was washed with 10% aqueous sodium trifluoroacetate solution and brine, dried over anhydrous sodium sulfate and filtered. The filtrate was concentrated to about 5 ml in vacuo. The concentrate was poured into diisopropyl ether (150 ml), and the resulting precipitate was collected by filtration and dried in vacuo. To a solution of the resulting solid in methylene chloride (3.0 ml) were added anisole (1.0 ml) and trifluoroacetic acid (2.0 ml). The resulting solution was stirred at room temperature for 4 hours and poured into diisopropyl ether (150 ml). The resulting precipitate was collected by filtration and dried in vacuo to give a crude product (830 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-[7-(2-aminoacetamido)-2,3-dihydro-5-(1H-imidazo[1,2-b]pyrazolio)]methyl-3-cephem-4-carboxylate (20.8 mg) as an amorphous solid.

$^1$H-NMR(D$_2$O) δ 1.51 (3H, s), 1.52 (3H, s), 3.26 (2H, d, J=18 Hz), 3.54 (2H, d, J=18 Hz), 3.97 (2H, s), 4.16 (2H, t, J=9 Hz), 4.35 (1H, q, J=9 Hz), 4.44 (1H, q, J=9 Hz), 4.97 (2H, d, J=15 Hz), 5.04 (2H, d, J=15 Hz), 5.25 (1H, d, J=4 Hz), 5.84 (1H, d, J=4 Hz), 8.10 (1H, s)

Preparation 40

To a suspension of 4,5-diamino-1-(2-hydroxyethyl)pyrazole sulfuric acid salt (1.20 g) and N-[2-(tert-butoxycarbonylamino)acetoxy]succinimide (1.35 g) in methylene chloride (20 ml) was added N-ethyldiisopropylamine (2.1 ml) under ice-cooling, and the mixture was stirred at room temperature for 17 hours. The reaction mixture was washed with water (40 ml), saturated aqueous sodium hydrogen carbonate solution (40 ml) and brine (40 ml). The organic layer was dried over anhydrous sodium sulfate, filtered and concentrated in vacuo. The oily residue was purified by column chromatography on silica gel eluting with 10% methanol/chloroform to give 5-amino-4-[2-(tert-butoxycarbonylamino)acetyl]amino-1-(2-hydroxyethyl)pyrazole (1.20 g) as a solid.

$^1$H-NMR(CDCl$_3$) δ 1.46 (9H, s), 3.89–3.90 (4H, m), 4.00–4.04 (2H, m), 4.26 (2H, br), 5.51 (1H, br), 7.17 (1H, s), 8.06 (1H, br)

EXAMPLE 23

7β-[(Z)-2-(5-Amino-1,2,4-thiadiazol-3-yl)-2-(1-carboxy-1-methylethoxyimino)acetamido]-3-[3-amino-4-(2-aminoacetamido)-2-(2-hydroxyethyl)-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 5-amino-4-[2-(tert-butoxycarbonylamino)acetyl]amino-1-(2-hydroxyethyl)pyrazole in the same manner as in Example 22 as an amorphous solid.

$^1$H-NMR(D$_2$O) δ 1.52 (6H, s), 3.15 (2H, d, J=18 Hz), 3.48 (2H, d, J=18 Hz), 3.88 (1H, dt, J=16 Hz), 4.02 (2H, s), 4.42 (1H, dt, J=16.5 Hz), 5.07 (2H, d, J=15 Hz), 5.13 (2H, d, J=15 Hz), 5.27 (1H, d, J=5 Hz), 5.84 (1H, d, J=5 Hz), 8.09 (1H, s)

Preparation 41

To a solution of 3-amino-4,5,6,7-tetrahydropyrazolo[1,5-a]pyrimidine sulfuric acid salt (2.96 g) and N-ethyldiisopropylamine (2.59 g) in methylene chloride (70 ml) was added N-[2-(tert-butoxycarbonylamino)acetoxy]succinimide (2.72 g). The mixture was stirred at room temperature for 14 hours. The reaction mixture was washed with saturated aqueous sodium hydrogen carbonate solution. The organic layer was dried over anhydrous magnesium sulfate, filtered and concentrated in vacuo. The residue was purified by column chromatography on silica gel eluting with 6% methanol/chloroform to give 3-[2-(tert-butoxycarbonylamino)acetyl]amino-4,5,6,7-tetrahydropyrazolo[1,5-a]pyrimidine (2.4 g) as a solid.

$^1$H-NMR(CDCl$_3$) δ 1.46 (9H, s), 2.08–2.12 (2H, m), 3.29–3.32 (2H, m), 3.90 (2H, br), 4.07 (2H, t, J=6.0 Hz), 5.00 (1H, br), 5.38 (H, br), 7.12 (1H, s), 8.11 (1H, br)

EXAMPLE 24

7β-[(Z)-2-(5-Amino-1,2,4-thiadiazol-3-yl)-2-(1-carboxy-1-methylethoxyimino)acetamido]-3-[3-(2-aminoacetamido)-4,5,6,7-tetrahydro-1-pyrazolo[1,5-a]pyrimidinio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 3-[2-(tert-butoxycarbonylamino)acetyl]amino-4,5,6,7-tetrahydropyrazolo[1,5-a]pyrimidine in the same manner as in Example 22 as an amorphous solid.

$^1$H-NMR (D$_2$O) δ 1.52 (3H, s), 1.53 (3H, s), 2.05–2.25 (2H, m), 3.21 (2H, d, J=18 Hz), 3.45 (2H, d, J=18 Hz), 3.30–3.45 (2H, m), 4.00 (2H, s), 4.10–4.25 (2H, m), 4.92 (2H, d, J=15 Hz), 5.17 (2H, d, J=15 Hz), 5.24 (1H, d, J=5 Hz), 5.84 (1H, d, J=5 Hz), 7.97 (1H, s)

Preparation 42

To a solution of 3-amino-4,5,6,7-tetrahydropyrazolo[1,5-a]pyrimidine sulfuric acid salt (4.44 g) and N-ethyldiisopropylamine (3.88 g) in methylene chloride (100 ml) was added N-[3-(tert-butoxycarbonylamino)propionyloxy]succinimide (4.29 g). The mixture was stirred at room temperature for 6 hours. The reaction mixture was washed with saturated aqueous sodium hydrogen carbonate solution. The organic layer was dried over anhydrous magnesium sulfate, filtered and concentrated in vacuo. The residue was purified by column chromatography on silica gel eluting with 5% methanol/chloroform to give 3-[3-(tert-butoxycarbonylamino)propionyl]amino-4,5,6,7-tetrahydropyrazolo[1,5-a]pyrimidine (3.67 g) as an oil.

$^1$H-NMR(CDCl$_3$) δ 1.43 (9H, s), 2.08–2.13 (2H, m), 2.52 (2H, t, J=6.0 Hz), 3.32 (2H, t, J=5.0 Hz), 3.43–3.46 (2H, m), 4.07 (2H, t, J=6.0 Hz), 5.12 (1H, br), 5.23 (1H, br), 7.13 (1H, s), 7.97 (1H, br)

EXAMPLE 25

7β-[(Z)-2-(5-Amino-1,2,4-thiadiazol-3-yl)-2-(1-carboxy-1-methylethoxyimino)acetamido]-3-[3-(3-aminopropionamido)-4,5,6,7-tetrahydro-1-pyrazolo[1,5-a]pyrimidinio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 3-[3-(tert-butoxycarbonylamino)propionyl]amino-4,5,6,7-tetrahydropyrazolo[1,5-a]pyrimidine in the same manner as in Example 22 as an amorphous solid.

$^1$H-NMR(D$_2$O) δ 1.51 (3H, s), 1.52 (3H, s), 2.05–2.25 (2H, m), 2.85 (2H, t, J=7 Hz), 3.20 (2H, d, J=18 Hz), 3.44 (2H, d, J=18 Hz), 3.30–3.45 (2H, m), 3.31 (2H, t, J=7 Hz), 4.05–4.20 (2H, m), 4.91 (2H, d, J=16 Hz), 5.16 (2H, d, J=16 Hz), 5.23 (1H, d, J=5 Hz), 5.84 (1H, d, J=5 Hz), 7.92 (1H, s)

Preparation 43

To a solution of 5-amino-1-methylpyrazole (100 g) in water (700 ml) were added concentrated hydrochloric acid (86 ml) and sodium nitrite (63.9 g) in water (200 ml) at a temperature below 10° C. The reaction mixture was stirred at 5° C. for 30 minutes. The precipitated solid was collected by filtration and dried to give 5-amino-1-methyl-4-nitrosopyrazole (117 g).
$^1$H-NMR(DMSO-$d_6$) δ 3.52 and 3.59 (3H, s), 7.22 and 8.51 (1H, s), 8.17 and 8.51 (1H, brs)

Preparation 44

To a suspension of 5-amino-1-methyl-4-nitrosopyrazole (117 g) were added sulfuric acid (91 g) and 10% palladium on carbon (58 g) The mixture was hydrogenated under balloon pressure for 10 hours. The reaction mixture was filtered, and the filtrate was concentrated in vacuo. To the concentrate was added isopropyl alcohol (2.3 L), and the mixture was stirred for 1 hour. The precipitated solid was collected by filtration and dried to give 4,5-diamino-1-methylpyrazole sulfuric acid salt (158 g).
$^1$H-NMR($D_2O$) δ 3.74 (3H, s), 7.80 (1H, s)

Preparation 45

A solution of 4,5-diamino-1-methylpyrazole sulfuric acid salt (158 g) in water (1.1 L) was neutralized to pH 6.9 with 4N aqueous sodium hydroxide solution, and dioxane (474 ml) was added to this solution. To the resulting mixture was added dropwise phenyl chloroformate (124 g) maintaining pH of the mixture at 6.9 with 4N aqueous sodium hydroxide solution at a temperature below 10° C. The reaction mixture was stirred for 1 hour. The precipitated solid was collected by filtration and dried to give 5-amino-1-methyl-4-phenoxycarbonylaminopyrazole (155 g).
$^1$H-NMR(DMSO-$d_6$) δ 3.52 (3H, s), 5.00 (2H, brs), 7.10–7.50 (6H, m), 8.93 (1H, brs)

Preparation 46

To a suspension of 5-amino-1-methyl-4-phenoxycarbonylaminopyrazole (153.8 g) in tetrahydrofuran (1 L) were added triethylamine (67 g) and triphenylmethyl chloride (185 g) at room temperature. The mixture was stirred for 6.5 hours. To the reaction mixture was added heptane (2.6 L), and the mixture was stirred for 1 hour. The precipitated solid was collected by filtration and washed with heptane-diisopropyl ether (1:1). The crude solid was suspended in water (3 L), and the suspension was stirred for 1 hour. The solid was collected by filtration and dried to give 1-methyl-4-phenoxycarbonylamino-5-triphenylmethylaminopyrazole (253.6 g).
$^1$H-NMR(DMSO-$d_6$) δ 2.74 (3H, s), 5.57 (1H, brs), 7.00–7.50 (21H, m), 8.12 (1H, brs)

Preparation 47

To a suspension of 1-methyl-4-phenoxycarbonylamino-5-triphenylmethylaminopyrazole (253.6 g) in N,N-dimethylformamide (1.5 L) were added triethylamine (59.5 g) and tert-butyl N-(2-aminoethyl)carbamate (94.2 g) in N,N-dimethylformamide (254 ml). The mixture was stirred for 5 hours and poured into water (10.6 L). The slurry was stirred for 1 hour. The precipitated solid was collected by filtration and dried to give a crude product. The crude product was suspended in N,N-dimethylformamide, and the suspension was heated under reflux for 20 minutes. The suspension was cooled to ambient temperature over 4 hours. The solid was collected by filtration, washed with acetonitrile and dried to give 4-[N-(2-tert-butoxycarbonylaminoethyl)carbamoylamino]-1-methyl-5-triphenylmethylaminopyrazole (261.2 g).
$^1$H-NMR(DMSO-$d_6$) δ2.69 (3H, s), 2.90–3.05 (4H, m), 5.69 (1H, brs), 5.91–6.01 (1H, m), 6.74–6.81 (1H, m), 6.87 (1H, brs), 7.00 (1H, s), 7.10–7.30 (15H, m)

Preparation 48

To a solution of (Z)-2-(5-amino-1,2,4-thiadiazol-3-yl)-2-(1-tert-butoxycarbonyl-1-methylethoxyimino)acetic acid (319 g) in N,N-dimethylacetamide (1.5 L) were added potassium carbonate (113 g) and methanesulfonyl chloride (126 ml) under ice-cooling. The mixture was stirred at 10° C. for 2 hours. The reaction mixture was added to a mixture of ethyl acetate and water. The organic layer was washed with water and brine to give an activated acid solution. On the other hand, a suspension of 4-methoxybenzyl 7β-amino-3-chloromethyl-3-cephem-4-carboxylate hydrochloride (300 g) in a mixture of water (1 L) and ethyl acetate (1 L) was adjusted to pH 6 with triethylamine under ice-cooling. To the resulting mixture was dropwise added the above obtained activated acid solution at 10° C. under stirring. Stirring was continued at 5–10° C. for 1.5 hours keeping pH of the reaction mixture at 6 with triethylamine. The organic layer was separated, washed with water and brine, and evaporated in vacuo. The concentrate was poured into diisopropyl ether (15 L), and the resulting precipitate was collected by filtration and dried to give 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (495.7 g).
$^1$H-NMR(DMSO-$d_6$) δ 1.39 (9H, s), 1.44 (6H, s), 3.45–3.70 (2H, m), 3.76 (3H, s), 4.46 and 4.54 (1H, ABq, J=16 Hz), 5.10–5.28 (2H+1H, m), 5.90 (1H, dd, J=4.9, 8.5 Hz), 6.94 (2H, d, J=8.7 Hz), 7.36 (2H, d, J=8.7 Hz), 8.18 (2H, brs), 9.52 (1H, d, J=8.5 Hz)

EXAMPLE 26

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (150 g) in N,N-dimethylformamide (400 ml) was added 1,3-bis(trimethylsilyl)urea (225 g) and the mixture was stirred for 30 minutes. Potassium iodide (51.2 g) was added to this solution, and the mixture was stirred for 30 minutes.

4-[N-(2-tert-Butoxycarbonylaminoethyl)carbamoylamino]-1-methyl-5-triphenylmethylaminopyrazole (147 g) was dissolved in N,N-dimethylformamide (650 ml) at 78° C. and the solution was cooled to 45° C. The solution was added to the solution of 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate obtained above. The reaction mixture was stirred at 35° C. for 18.5 hours and poured into a mixture of ethyl acetate (2 L), water (1.8 L) and 20% aqueous sodium chloride solution (150 ml). The organic layer was washed with a mixture of 10% aqueous sodium thiosulfate solution (375 ml) and 20% aqueous sodium chloride solution (375 ml) The organic layer was washed successively with 10% aqueous sodium trifluoroacetate solution three times (750 ml×3) and 20% aqueous sodium chloride solution (750 ml). The organic layer was concentrated in vacuo, and the precipitated 4-[N-(2-tert-butoxycarbonylaminoethyl)carbamoylamino]-1-methyl-5-triphenylmethylaminopyrazole was filtered off. The filtrate was further concentrated in vacuo to a volume of approximately 600 ml. This solution was added to diisopropyl ether and the suspension was stirred for 1 hour. The resulting solid was collected by filtration and dried. The solid was dissolved in dichloromethane (669 ml). To the solution were added anisole (223 ml) and trifluoroacetic acid (669 ml). The reaction mixture was stirred for 4 hours and poured into diisopropyl ether. The resulting solid was collected by filtration and dried. This solid was suspended in water, and pH of the suspension was adjusted to 7 with aqueous ammonia solution at a temperature below 10° C. The resulting precipitate was filtered off. The filtrate was acidified to pH 1 with concentrated hydrochloric acid at a temperature below 10° C., and the resulting precipitate was filtered off. The filtrate was chromatographed on Diaion® HP-20 (11 L) eluting with 20% aqueous 2-propanol. The eluate was concentrated to about 3.5 L in vacuo, and 2M sulfuric acid (51 ml) was added. The mixture was lyophilized to give a crude product (72.2 g).

The crude product (3 g) was purified by preparative HPLC utilizing ODS column. The eluate containing a desired product was concentrated in vacuo. The concentrate was adjusted to about pH 1 with concentrated hydrochloric acid and chromatographed on Diaion® HP-20 (400 ml) eluting with 20% aqueous 2-propanol. The eluate was concentrated to about 73 ml in vacuo, and 2M sulfuric acid (1.5 ml) was added. The mixture was further evaporated to a volume of approximately 12.5 ml, and water (6 ml) was added. After addition of seed crystals (10 mg), which resulted in the precipitation of a white solid, the mixture was stirred at room temperature for 1 hour. The mixture was further stirred at 5° C. for 13 hours. 2-Propanol (20 ml) was added at 5° C. over 20 minutes, and the slurry was stirred at room temperature for 4 hours. 2-Propanol (20 ml) was added over 30 minutes, and the slurry was stirred at room temperature for 3 hours. The precipitated crystals were collected by filtration and dried to give 7β-(Z)-2-(5-amino-1,2,4-thiadiazol-3-yl)-2-(1-carboxy-1-methylethoxyimino)acetamido]-3-{3-amino-4-[N-(2-aminoethyl)carbamoylamino]-2-methyl-1-pyrazolio}methyl-3-cephem-4-carboxylic acid hydrogen sulfate (1.51 g) as crystals.

$^1$H-NMR(D$_2$O) δ 1.61 (6H, s), 3.10–3.55 (6H, m), 3.71 (3H, s), 5.02 and 5.23 (2H, ABq, J=16.7 Hz), 5.25 (1H, d, J=4.9 Hz), 5.87 (1H, d, J=4.9 Hz), 7.91 (1H, s)

Preparation 49

A suspension of 4,5-diamino-1-methylpyrazole sulfuric acid salt (20 g) in triethylamine (29.2 ml) was stirred at 0° C. for 10 minutes. A mixture of acetic anhydride (9.87 ml) and formic acid (7.96 ml) was stirred at 40° C. for 30 minutes, cooled to 0° C., and added dropwise to the above solution at 0° C. The whole mixture was stirred at 0° C. for 2 hours. To the mixture was added brine, and the whole mixture was extracted with tetrahydrofuran. The organic layer was dried over magnesium sulfate and evaporated under reduced pressure to give crude N-(5-amino-1-methyl-1H-pyrazol-4-yl)formamide, which was used in the next step without further purification.

Preparation 50

The crude product of N-(5-amino-1-methyl-1H-pyrazol-4-yl)formamide (13.33 g) was dissolved in N,N-dimethylformamide (130 ml). To the solution were added trityl chloride (29.2 g), triethylamine (66.3 ml) and 4-dimethylaminopyridine (465 mg), and the mixture was stirred at 60° C. for 5 hours. To the reaction mixture was added water, and the whole mixture was extracted with ethyl acetate. The organic layer was washed with water and brine, and dried over magnesium sulfate. The solvent was evaporated under reduced pressure to give a white solid. The solid was triturated with ethyl acetate/diisopropyl ether (1:1) to give N-[1-methyl-5-(tritylamino)-1H-pyrazol-4-yl]formamide (19.18 g). The NMR spectrum of this compound indicates the existence of its rotamer.

$^1$H-NMR(DMSO-d$_6$) δ 2.76 and 2.92 (3H, s), 5.56 and 5.84 (1H, s), 7.0–7.4 (16H, m), 7.66 (1H, d, J=1.7 Hz), 8.3–8.4 (1H, m)

ESI-MS: m/z=405.2(M+Na)$^+$

Preparation 51

To a solution of N-[1-methyl-5-(tritylamino)-1H-pyrazol-4-yl]formamide (3.825 g) in N,N-dimethylformamide (66 ml) was added sodium hydride (264 mg, 60% oil suspension) under a nitrogen atmosphere at 0° C. under stirring. The mixture was stirred at 0° C. for 15 minutes. To the mixture were added tert-butyl N-(3-bromopropyl)carbamate (2.62 g) in N,N-dimethylformamide (10 ml) and sodium iodide (1.65 g). The mixture was warmed to room temperature and stirred for 2 hours. 10% Aqueous potassium hydrogen sulfate solution (5 ml) was added, and the mixture was extracted with ethyl acetate. The organic layer was washed with water and brine, and dried over magnesium sulfate. The solvent was evaporated under reduced pressure, and the residue was chromatographed on silica gel eluting with methylene chloride/ethyl acetate (4:1) to give tert-butyl 3-{N-formyl-N-[1-methyl-5-(tritylamino)-1H-pyrazol-4-yl]amino}propylcarbamate (2.714 g). The NMR spectrum of this compound indicates the existence of its rotamer.

$^1$H-NMR(DMSO-d$_6$) δ 1.37 and 1.39 (9H, s), 2.6–2.9 (6H, m), 2.89 (3H, s), 5.34 and 6.01 (1H, s), 6.6–6.9 (1H, m), 7.0–7.4 (15H, m), 7.5–7.6 (1H, m), 7.95 (1H, s)

ESI-MS: m/z=562.3(M+Na)$^+$

EXAMPLE 27

7β-[(Z)-2-(5-Amino-1,2,4-thiadiazol-3-yl)-2-(1-carboxy-1-methylethoxyimino)acetamido]-3-{3-amino-4-[N-(3-aminopropyl)-N-formylamino]-2-methyl-1-pyrazolio}methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate and tert-butyl 3-{N-formyl-N-[1-methyl-5-(tritylamino)-1H-pyrazol-4-yl]amino}propylcarbamate in the same manner as in Example 1. The NMR spectrum of this compound indicates the existence of its rotamer.

$^1$H-NMR(D$_2$O) δ 1.53 (6H, s), 1.7–2.1 (2H, m), 2.9–3.9 (9H, m), 4.97 and 5.20 (2H, ABq, J=15.2 Hz), 5.26 (1H, d, J=4.8 Hz), 5.84 (1H, d, J=4.8 Hz), 8.0–8.3 (2H, m)

EXAMPLE 28

To a suspension of 7β-[(Z)-2-(5-amino-1,2,4-thiadiazol-3-yl)-2-(1-carboxy-1-methylethoxyimino)acetamido]-3-{3-amino-4-[N-(3-aminopropyl)-N-formylamino]-2-methyl-1-pyrazolio}methyl-3-cephem-4-carboxylate (140 mg) in methanol (2.6 ml) was added concentrated hydrochloric acid (0.176 ml) at room temperature, and the mixture was stirred for 6.5 hours. To the reaction mixture was added sodium hydrogen carbonate (177 mg), and the mixture was purified by preparative HPLC (ODS column, acetonitrile/phosphate buffer (pH 7)=5:95). The eluate containing a desired product was evaporated to remove acetonitrile, acidified with diluted hydrochloric acid and chromatographed on Diaion® HP-20 eluting with 20% aqueous 2-propanol. The eluate was concentrated under reduced pressure and lyophilized to give 7β-[(Z)-2-(5-amino-1,2,4-thiadiazol-3-yl)-2-(1-carboxy-1-methylethoxyimino)acetamido]-3-{3-amino-4-[(3-aminopropyl)amino]-2-methyl-1-pyrazolio}methyl-3-cephem-4-carboxylate (39 mg).

$^1$H-NMR(D$_2$O) δ 1.52–1.54 (6H, m), 1.95 (2H, tt, J=7.3 Hz, 7.3 Hz), 3.0–3.2 (4H, m), 3.16 and 3.38 (2H, ABq, J=17.7 Hz), 3.68 (3H, s), 4.89 and 5.11 (2H, ABq, J=15.6 Hz), 5.22 (1H, d, J=4.8 Hz), 5.83 (1H, d, J=4.8 Hz), 7.59 (1H, s)

ESI-MS: m/z=636.3(M−H)$^-$

Preparation 52 tert-Butyl 2-{N-formyl-N-[1-methyl-5-(tritylamino)-1H-pyrazol-4-yl]amino}ethylcarbamate The title compound was obtained from N-[1-methyl-5-(tritylamino)-1H-pyrazol-4-yl]formamide and tert-butyl N-(2-bromoethyl)carbamate in the same manner as in Preparation 51.

IR(KBr) 1709, 1670, 1170, 704 cm$^{-1}$ $^1$H-NMR(DMSO-d$_6$) δ 1.35 and 1.36 (9H, s), 2.65 and 2.75 (3H, s), 2.73–2.90 (4H, m), 5.45 and 6.02 (1H, s), 6.78 and 6.88 (1H, t-like), 7.05–7.30 (15H, m), 7.31 and 7.57 (1H, s)

ESI-MS: m/z=426.3(M+H$^+$), 548.3(M+Na$^+$)

EXAMPLE 29

7β-[(Z)-2-(5-Amino-1,2,4-thiadiazol-3-yl)-2-(1-carboxy-1-methylethoxyimino)acetamido]-3-{3-amino-4-[N-(2-aminoethyl)-N-formylamino]-2-methyl-1-pyrazolio}methyl-3-cephem-4-carboxylate The title compound was obtained from benzhydryl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and tert-butyl 2-{N-formyl-N-[1-methyl-5-(tritylamino)-1H-pyrazol-4-yl]amino}ethylcarbamate in the same manner as in Example 1.

IR(KBr) 1770, 1675, 1653, 1597 cm$^{-1}$ $^1$H-NMR(DMSO-d$_6$) δ 1.53 (6H, s), 3.12–3.78 (4H, m), 3.77 and 3.78 (3H, s), 3.86–3.96 (2H, m), 5.00 and 5.19 (2H, ABq, J=15.2 Hz), 5.28 (1H, d, J=4.8 Hz), 5.86 (1H, d, J=4.8 Hz), 8.15 and 8.18 (1H, s), 8.19 and 8.33 (1H, s)

ESI-MS: m/z=652.2(M+H$^+$)

EXAMPLE 30

7β-[(Z)-2-(5-Amino-1,2,4-thiadiazol-3-yl)-2-(1-carboxy-1-methylethoxyimino)acetamido]-3-{3-amino-4-[(2-aminoethyl)amino]-2-methyl-1-pyrazolio}methyl-3-cephem-4-carboxylate The title compound was obtained from 7β-[(Z)-2-(5-amino-1,2,4-thiadiazol-3-yl)-2-(1-carboxy-1-methylethoxyimino)acetamido]-3-{3-amino-4-[N-(2-aminoethyl)-N-formylamino]-2-methyl-1-pyrazolio}methyl-3-cephem-4-carboxylate in the same manner as in Example 28.

IR(KBr) 1770, 1651, 1593 cm$^{-1}$ $^1$H-NMR(DMSO-d$_6$) δ 1.53 (3H, s), 1.59 (3H, s), 3.13–3.26 (4H, m), 3.26 and 3.39 (2H, ABq, J=17.8 Hz), 3.68 (3H, s), 4.87 and 5.11 (2H, ABq, J=15.7 Hz), 5.25 (1H, d, J=4.8 Hz), 5.84 (1H, d, J=4.8 Hz), 7.63 (1H, s)

ESI-MS: m/z=622.2(M−H$^-$)

Preparation 53

To a suspension of 1-methyl-1H-pyrazole-4,5-diamine sulfate (86 g) in tetrahydrofuran (1.3 L) was added triethylamine (117 ml), and then (2S)-4-[(tert-butoxycarbonyl)amino]-2-hydroxybutanoic acid (82.5 g) was added to the mixture. To the mixture were added 1-hydroxybenzotriazole (58.3 g) and N-(3-dimethylaminopropyl)-N'-ethylcarbodiimide hydrochloride (82.7 g) under ice-cooling. The reaction mixture was stirred at room temperature for 8 hours. To the reaction mixture were added ethyl acetate (1.3 L), saturated aqueous sodium hydrogen carbonate solution and sodium chloride, and the mixture was stirred for 30 minutes. The organic layer was separated, and the aqueous layer was extracted with ethyl acetate (1.0 L) six times. The extract was dried over anhydrous magnesium sulfate, filtered and concentrated in vacuo. The residue was purified by silica gel column chromatography eluting with ethyl acetate/tetrahydrofuran (1/1) to give tert-butyl {(3S)-4-[(5-amino-1-methyl-1H-pyrazol-4-yl)amino]-3-hydroxy-4-oxobutyl}carbamate (69.5 g).

$^1$H-NMR(CDCl$_3$) δ 1.43 (9H, s), 1.6–1.9 (1H, m), 1.9–2.2 (1H, m), 3.1–3.3 (1H, m), 3.3–3.5 (1H, m), 3.65 (3H, s), 4.20 (1H, dd, J=3.6, 6.6 Hz), 4.7–5.3 (4H, m), 7.24 (1H, s), 8.58 (1H, s)

[α]$^{20}_D$(c=1.05, CHCl$_3$)=−27.06°

Preparation 54

To a solution of tert-butyl {(3S)-4-[(5-amino-1-methyl-1H-pyrazol-4-yl)amino]-3-hydroxy-4-oxobutyl}carbamate (68.51 g) in N,N-dimethylformamide (350 ml) was added chlorotriphenylmethane (67 g). To the mixture was dropwise added triethylamine (67 ml). The mixture was stirred at room temperature for 12 hours. The reaction mixture was dissolved in dichloromethane (2 L). The solution was washed successively with water and brine. The extract was dried over anhydrous magnesium sulfate, filtered and concentrated in vacuo. The residue was triturated with acetonitrile and dried in vacuo to give tert-butyl ((3S)-3-hydroxy-4-{[1-methyl-5-(tritylamino)-1H-pyrazol-4-yl]amino}-4-oxobutyl)carbamate (64 g).

$^1$H-NMR(CDCl$_3$) δ 1.46 (9H, s), 1.3–1.6 (1H, m), 1.8–2.1 (1H, m), 2.95 (3H, s), 2.9–3.2 (1H, m), 3.3–3.6 (1H, m), 3.95 (1H, m), 4.53 (1H, d, J=4.5 Hz), 4.74 (1H, s), 4.92 (1H, brs), 7.1–7.3 (15H, m), 7.39 (1H, s), 7.73 (1H, s)

ESI-MS: m/z=638.2(M+H+Na$^+$)

[α]$^{20}_D$(c=1.025, CHCl$_3$)=−36.5°

EXAMPLE 31

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (130 g) in N,N-dimethylformamide (400 ml) was added 1,3-bis(trimethylsilyl)urea (195 g), and the mixture was stirred at room temperature for 30 minutes. To the solution was added potassium iodide (44.4 g), and the mixture was stirred at room temperature for 30 minutes. To the reaction mixture was added tert-butyl ((3S)-3-hydroxy-4-{[1-methyl-5-(tritylamino)-1H-pyrazol-4-yl]amino}-4-oxobutyl)carbamate (106 g), and the whole mixture was stirred at 35° C. for 22 hours. To the reaction mixture was added ethyl acetate (1.7 L), and the mixture was washed successively with water (1.6 L), 10% aqueous sodium trifluoroacetate solution (650 ml×3) and brine (650 ml), dried over magnesium sulfate and filtered. The filtrate was concentrated to about 1 L in vacuo. The concentrate was poured into diisopropyl ether (3 L), and the resulting precipitate was collected by filtration and dried in vacuo. To a solution of the solid in methylene chloride (660 ml) were added anisole (220 ml) and trifluoroacetic acid (660 ml).

The resulting solution was stirred at room temperature for 4 hours and poured into diisopropyl ether (7 L). The resulting precipitate was collected by filtration and dried in vacuo to give a crude product (156.2 g). The crude product was dissolved in water (3.5 L). The solution was adjusted to about pH 3 with concentrated hydrochloric acid and chromatographed on Diaion® HP-20 (Mitsubishi Chemical Corporation) eluting with 20% aqueous 2-propanol. The eluate was concentrated to about 1.5 L in vacuo, and 2M aqueous sulfuric acid solution (33.18 ml) was added. The mixture was lyophilized. The lyophilized product (40 g) was dissolved in phosphate buffer (pH 7) and purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 10% aqueous 2-propanol. The eluate was concentrated to about 1 L in vacuo, and 2M aqueous sulfuric acid solution was added (13.59 ml). The resulting solution was lyophilized to give 7β-[(Z)-2-(5-amino-1,2,4-thiadiazol-3-yl)-2-(1-carboxy-1-methylethoxyimino)acetamido]-3-{3-amino-4-[((2S)-4-amino-2-hydroxybutanoyl)amino]-2-methyl-1-pyrazolio}methyl-3-cephem-4-carboxylic acid hydrogen sulfate (20.82 g) as an amorphous solid.

$^1$H-NMR($D_2O$) δ 1.61 (6H, s), 1.9–2.4 (2H, m), 3.20 (1H, d, J=17.6 Hz), 3.0–3.3 (2H, m), 3.45 (1H, d, J=17.6 Hz), 3.74 (3H, s), 4.47 (1H, dd, J=4, 6.3 Hz), 5.06 (1H, d, J=15.7 Hz), 5.25 (1H, d, J=4.8 Hz), 5.28 (1H, d, J=15.7 Hz), 5.87 (1H, d, J=4.8 Hz), 8.07 (1H, s)

Preparation 55

To a suspension of 1-methyl-$N^5$-trityl-1H-pyrazole-4,5-diamine (1.60 g) in ethanol (50 ml) were added triethylamine (0.627 ml) and diethyl squarate (0.858 ml), and the mixture was stirred at room temperature for 22 hours. To the reaction mixture were added ethyl acetate (200 ml) and hexane (100 ml), and the solution was washed successively with water, 5% aqueous citric acid solution and brine. The organic layer was dried over anhydrous sodium sulfate, filtered and concentrated in vacuo. The crystalline residue was washed with diethyl ether and dried in vacuo to give 3-ethoxy-4-{[1-methyl-5-(tritylamino)-1H-pyrazol-4-yl]amino}-3-cyclobutene-1,2-dione (1.45 g) as a solid.

$^1$H-NMR(CDCl$_3$) δ 1.42 (3H, br), 2.99 (3H, s), 4.41 (1H, brs), 4.69 (2H, q, J=7.2 Hz), 6.40 (1H, br), 7.13–7.35 (16H, m)

Preparation 56

To a suspension of tert-butyl 2-aminoethylcarbamate (288 mg) and 3-ethoxy-4-{[1-methyl-5-(tritylamino)-1H-pyrazol-4-yl]amino}-3-cyclobutene-1,2-dione (718 mg) in ethanol (20 ml) was added triethylamine (0.209 ml), and the mixture was stirred under reflux for 4 hours. To the reaction mixture were added diethyl ether and hexane. The crystalline precipitate was collected by filtration and dried in vacuo to give tert-butyl 2-[(2-{[1-methyl-5-(tritylamino)-1H-pyrazol-4-yl]amino}-3,4-dioxocyclobut-1-en-1-yl)amino]ethylcarbamate (830 mg) as a solid.

$^1$H-NMR(CDCl$_3$) δ 1.40 (9H, s), 3.07–3.28 (5H, m), 3.38–3.67 (2H, m), 4.53–4.84 (1H, br), 4.84 (1H, br), 7.15–7.22 (6H, m), 7.23 (1H, s), 7.22–7.34 (9H, m)

EXAMPLE 32

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (901 mg) in N,N-dimethylformamide (1.8 ml) was added N-(trimethylsilyl)acetamide (720 mg), and the mixture was stirred at room temperature for 1 hour. To the reaction mixture was added a solution of tert-butyl 2-[(2-{[1-methyl-5-(tritylamino)-1H-pyrazol-4-yl]amino}-3,4-dioxocyclobut-1-en-1-yl)amino]ethylcarbamate (682 mg) in N,N-dimethylformamide (6.3 ml), and the whole mixture was stirred at 35–40° C. for 7 hours. To the resulting reaction mixture was added ethyl acetate, and the precipitate was filtered off. The filtrate was washed successively with water and brine, dried over anhydrous sodium sulfate and filtered. The filtrate was concentrated to about 5 ml in vacuo. The concentrate was poured into diisopropyl ether (80 ml), and the resulting precipitate was collected by filtration and dried in vacuo. To a solution of the resulting solid in methylene chloride (2.6 ml) were added anisole (0.88 ml) and trifluoroacetic acid (2.6 ml). The resulting solution was stirred at room temperature for 3 hours and poured into diisopropyl ether (80 ml). The resulting precipitate was collected by filtration and dried in vacuo to give a crude product (580 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 10 ml in vacuo and lyophilized to give 3-{[3-amino-4-({2-[(2-aminoethyl)amino]-3,4-dioxo-1-cyclobuten-1-yl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (22 mg) as an amorphous solid.

$^1$H-NMR($D_2O$) δ 1.53 (3H, s), 1.54 (3H, s), 3.26–3.36 (1H, m), 3.27 (2H, t, J=5.7 Hz), 3.58–3.69 (1H, m), 3.74 (3H, s), 3.86–4.03 (2H, m), 4.93 (1H, d, J=14.5 Hz), 5.10 (1H, d, J=14.5 Hz), 5.29 (1H, d, J=4.3 Hz), 5.83 (1H, d, J=4.3 Hz), 7.99 (1H, s)

Preparation 57

To a suspension of tert-butyl 3-aminopropylcarbamate (366 mg) and 3-ethoxy-4-{[1-methyl-5-(tritylamino)-1H-pyrazol-4-yl]amino}-3-cyclobutene-1,2-dione (67.0 mg) in ethanol (30 ml) was added triethylamine (0.195 ml), and the mixture was stirred under reflux for 3 hours. To the reaction mixture were added diethyl ether (40 ml) and hexane (10 ml). The crystalline precipitate was collected by filtration and dried in vacuo to give tert-butyl {3-[(2-{[1-methyl-5-(tritylamino)-1H-pyrazol-4-yl]amino}-3,4-dioxo-1-cyclobuten-1-yl)amino]propyl}carbamate (788 mg) as a solid.

$^1$H-NMR(CDCl$_3$) δ 1.43 (9H, s), 1.67 (2H, quintet, J=5.5 Hz), 3.15 (2H, q, J=5.5 Hz), 3.17 (3H, s), 3.60 (2H, q, J=5.5 Hz), 4.82 (1H, brs), 4.86 (1H, t, J=5.5 Hz), 5.44 (1H, br), 5.86 (1H, br), 7.13–7.33 (15H, m), 7.17 (1H, s)

EXAMPLE 33

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (819 mg) in N,N-dimethylformamide (1.6 ml) was added N-(trimethylsilyl)acetamide (656 mg), and the mixture was stirred at room temperature for 40 minutes. To the reaction mixture was added a solution of tert-butyl {3-[(2-{[1-methyl-5-(tritylamino)-1H-pyrazol-4-yl]amino}-3,4-dioxo-1-cyclobuten-1-yl)amino]propyl}carbamate (637 mg) in N,N-dimethylformamide (3.2 ml), and the whole mixture was stirred at 35–40° C. for 3.5 hours. To the resulting reaction mixture was added ethyl acetate (60 ml), and the precipitate was filtered off. The filtrate was washed successively with water (50 ml×2) and brine (50 ml), dried over anhydrous sodium sulfate and filtered. The filtrate was concentrated to about 8 ml in vacuo. The concentrate was poured into diisopropyl ether (80 ml), and the resulting precipitate was collected by filtration and dried in vacuo. To a solution of the resulting solid in methylene chloride (2.4 ml) were added anisole (0.80 ml) and trifluoroacetic acid (1.6 ml). The resulting solution was stirred at room temperature for 3 hours and poured into diisopropyl ether (80 ml). The resulting precipitate was collected by filtration and dried in vacuo to give a crude product (565 mg), which was purified by preparative HPLC utilizing ODS column eluting with a mixture of acetonitrile and phosphate buffer (pH 5.5). The eluate containing a desired product was concentrated to about 20 ml in vacuo. The concentrate was desalted by preparative HPLC utilizing ODS column, and the fraction eluted with 8% acetonitrile/0.01 M hydrochloric acid was concentrated to about 10 ml in vacuo and lyophilized to give 3-{[3-amino-4-({2-[(3-aminopropyl)amino]-3,4-dioxo-1-cyclobuten-1-yl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate trihydrochloride (34 mg) as an amorphous solid.

$^1$H-NMR(D$_2$O) δ 1.62 (6H, s), 2.02 (2H, quintet, J=7.3 Hz), 3.09 (2H, t, J=7.3 Hz), 3.32 (1H, d, J=17.5 Hz), 3.54–3.65 (1H, m), 3.67–3.78 (2H, m), 3.75 (3H, s), 4.93–5.23 (2H, m), 5.30 (1H, d, J=4.5 Hz), 5.86 (1H, d, J=4.5 Hz), 7.99 (1H, s)

Preparation 58

To a solution of 1,1'-(1,2-dioxo-1,2-ethanediyl)bis-1H-imidazole (761 mg) in N,N-dimethylformamide (8 ml) was added 1-methyl-N$^5$-trityl-1H-pyrazole-4,5-diamine (709 mg) under ice-cooling, and the mixture was stirred at room temperature for 30 minutes. To the reaction mixture was added a solution of tert-butyl 2-aminoethylcarbamate (1.28 g) in N,N-dimethylformamide (2 ml), and the mixture was stirred at room temperature for 27 hours. To the reaction mixture was added ethyl acetate (50 ml). After the precipitate was filtered off, the filtrate was washed successively with water, 5% aqueous citric acid solution and brine. The organic layer was dried over anhydrous sodium sulfate, filtered and concentrated in vacuo. The crystalline residue was washed with a mixed solvent of diethyl ether and ethyl acetate and dried in vacuo to give tert-butyl {2-[(2-{[1-methyl-5-(tritylamino)-1H-pyrazol-4-yl]amino}-2-oxoacetyl)amino]ethyl}carbamate (823 mg) as a solid.

$^1$H-NMR(CDCl$_3$) δ 1.43 (9H, s), 2.97 (3H, s), 3.31 (2H, q, J=5.5 Hz), 3.43 (2H, q, J=5.5 Hz), 4.53 (1H, s), 4.84 (1H, brs), 7.10–7.30 (15H, m), 7.47 (1H, s), 7.67 (1H, brs), 8.20 (1H, brs)

EXAMPLE 34

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (618 mg) in N,N-dimethylformamide (1.5 ml) was added N-(trimethylsilyl)acetamide (656 mg), and the mixture was stirred at room temperature for 40 minutes. To the solution was added potassium iodide (232 mg), and the mixture was stirred at room temperature for 35 minutes. To the reaction mixture was added a solution of tert-butyl {2-[(2-{[1-methyl-5-(tritylamino)-1H-pyrazol-4-yl]amino}-2-oxoacetyl)amino]ethyl}carbamate (626 mg) in N,N-dimethylformamide (3 ml), and the whole mixture was stirred at 35–40° C. for 24 hours. To the resulting reaction mixture was added ethyl acetate (50 ml), and the solution was washed successively with water (50 ml×2), 10% aqueous sodium trifluoroacetate solution (50 ml×2), and brine (50 ml), dried over anhydrous sodium sulfate and filtered. The filtrate was concentrated to about 10 ml in vacuo. The concentrate was poured into diisopropyl ether (60 ml), and the resulting precipitate was collected by filtration and dried in vacuo. To a solution of the solid in methylene chloride (2.9 ml) were added anisole (0.95 ml) and trifluoroacetic acid (2.9 ml). The resulting solution was stirred at room temperature for 4 hours and poured into diisopropyl ether (60 ml). The resulting precipitate was collected by filtration and dried in vacuo to give a crude product (770 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 10 ml in vacuo and lyophilized to give 3-{[3-amino-4-({2-[(2-aminoethyl)amino]-2-oxoacetyl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (31 mg) as an amorphous solid.

$^1$H-NMR(D$_2$O) δ 1.52 (3H, s), 1.53 (3H, s), 3.20 (1H, d, J=18.0 Hz), 3.24 (2H, t, J=6.0 Hz), 3.45 (1H, d, J=18.0 Hz), 3.66 (2H, t, J=6.0 Hz), 3.75 (3H, s), 5.02 (1H, d, J=15.5 Hz), 5.21 (1H, d, J=15.5 Hz), 5.25 (1H, d, J=5.0 Hz), 5.85 (1H, d, J=5.0 Hz), 8.14 (1H, s)

Preparation 59

To a suspension of phenyl [1-methyl-5-(tritylamino)-1H-pyrazol-4-yl]carbamate (711 mg) and tert-butyl 3-azetidinylcarbamate acetic acid salt (418 mg) in methylene chloride (8 ml) was added N-ethyldiisopropylamine (0.62 ml), and the mixture was stirred under reflux for 16 hours. To the reaction mixture was added methylene chloride, and the solution was washed successively with 10% aqueous citric acid solution, 10% aqueous sodium hydroxide solution and brine. The organic layer was dried over anhydrous magnesium sulfate, filtered and concentrated in vacuo. The residue was triturated with a mixed solvent of ethyl acetate and hexane to give tert-butyl [1-({[1-methyl-5-(tritylamino)-1H-pyrazol-4-yl]amino}carbonyl)-3-azetidinyl]carbamate (735 mg) as a solid;

$^1$H-NMR(CDCl$_3$) δ 1.47 (9H, s), 2.92 (3H, s), 3.56 (2H, dd, J=7.5, 5.0 Hz), 4.02 (2H, dd, J=7.5, 7.5 Hz), 4.42 (1H, brs), 4.71 (1H, s), 4.74 (1H, s), 4.94 (1H, brs), 7.18–7.21 (7H, m), 7.25–7.32 (9H, m)

EXAMPLE 35

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (819 mg) in N,N-dimethylformamide (2.4 ml) was added N-(trimethylsilyl)acetamide (655 mg), and the mixture was stirred at room temperature for 30 minutes. To the reaction mixture was added a solution of tert-butyl [1-({[1-methyl-5-(tritylamino)-1H-pyrazol-4-yl]amino}carbonyl)-3-azetidinyl]carbamate (553 mg) in N,N-dimethylformamide (3 ml), and the whole mixture was stirred at room temperature for 3 hours, and then stirred at 50° C. for 1 hour. To the resulting reaction mixture were added ethylacetate (50 ml) and water (50 ml). The aqueous layer was separated, and the organic layer was washed with water and brine, dried over anhydrous magnesium sulfate and filtered. The filtrate was concentrated to about 5 ml in vacuo. The concentrate was poured into diisopropyl ether (80 ml), and the resulting precipitate was collected by filtration and dried in vacuo. To a solution of the resulting solid in methylene chloride (2.1 ml) were added anisole (0.7 ml) and trifluoroacetic acid (2.1 ml). The resulting solution was stirred at room temperature for 4.5 hours and poured into diisopropyl ether (80 ml). The resulting precipitate was collected by filtration and dried in vacuo to give a crude product (521 mg), which was purified by preparative HPLC utilizing ODS column eluting with a mixture of acetonitrile and phosphate buffer (pH 5.5). The eluate containing a desired product was concentrated to about 20 ml in vacuo. The concentrate was desalted by preparative HPLC utilizing ODS column, and the fraction eluted with 7% acetonitrile/0.01 M hydrochloric acid was concentrated to about 10 ml in vacuo and lyophilized to give 3-[(3-amino-4-{[(3-amino-1-azetidinyl)carbonyl]amino}-2-methyl-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate trihydrochloride (22 mg) as an amorphous solid.

$^1$H-NMR(D$_2$O) δ 1.62 (3H, s), 1.63 (3H, s), 3.25 (1H, d, J=17.9 Hz), 3.50 (1H, d, J=17.9 Hz), 3.72 (3H, s), 4.14 (2H, dd, J=9.6, 4.4 Hz), 4.25 (1H, tt, J=7.8, 4.6 Hz), 4.46 (2H, dd, J=9.6, 7.8 Hz), 5.08 (1H, d, J=15.6 Hz), 5.24 (1H, d, J=15.6 Hz), 5.27 (1H, d, J=4.6 Hz), 5.88 (1H, d, J=4.6 Hz), 7.91 (1H, s)

Preparation 60

To a suspension of phenyl [1-methyl-5-(tritylamino)-1H-pyrazol-4-yl]carbamate (2.18 g) and tert-butyl 3-amino-1-azetidinecarboxylate (793 mg) in methylene chloride (20 ml) was added N-ethyldiisopropylamine (1.07 ml), and the mixture was stirred under reflux for 40 hours. To the reaction mixture was added methylene chloride, and the solution was washed successively with 10% aqueous citric acid solution, 10% aqueous sodium hydroxide solution and brine. The organic layer was dried over anhydrous magnesium sulfate, filtered and concentrated in vacuo. The residue was purified by column chromatography on silica gel eluting with 10% methanol/methylene chloride to give tert-butyl 3-[({[1-methyl-5-(tritylamino)-1H-pyrazol-4-yl]amino}carbonyl)amino]-1-azetidinecarboxylate (1.52 g) as a solid.

$^1$H-NMR(CDCl$_3$) δ 1.44 (9H, s), 3.03 (3H, s), 3.59 (2H, dd, J=9.2, 5.0 Hz), 4.17 (2H, dd, J=9.2, 7.8 Hz), 4.39–4.43 (3H, m), 4.64 (1H, brs), 7.18–7.21 (6H, m), 7.27 (1H, s), 7.29–7.32 (9H, m)

EXAMPLE 36

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.48 g) in N,N-dimethylformamide (3.0 ml) was added N-(trimethylsilyl)acetamide (1.42 g), and the mixture was stirred at room temperature for 30 minutes. To the solution was added potassium-iodide (504 mg) and the mixture was stirred at room temperature for 30 minutes. To the reaction mixture was added a solution of tert-butyl 3-[({[1-methyl-5-(tritylamino)-1H-pyrazol-4-yl]amino}carbonyl)amino]-1-azetidinecarboxylate (1.20 g) in N,N-dimethylformamide (2.2 ml), and the whole mixture was stirred at 50° C. for 16 hours. To the resulting reaction mixture was added ethyl acetate (200 ml), and the solution was washed successively with water (50 ml), 10% aqueous sodium trifluoroacetate solution (50 ml×2) and brine (50 ml), dried over anhydrous sodium sulfate and filtered. The filtrate was concentrated to about 10 ml in vacuo. The concentrate was poured into diisopropyl ether (160 ml), and the resulting precipitate was collected by filtration and dried in vacuo. To a solution of the solid in methylene chloride (8.64 ml) were added anisole (2.88 ml) and trifluoroacetic acid (8.64 ml). The resulting solution was stirred at room temperature for 3 hours and poured into diisopropyl ether (160 ml). The resulting precipitate was collected by filtration and dried in vacuo to give a crude product (2.22 g), which was purified by preparative HPLC utilizing ODS column eluting with a mixture of acetonitrile and phosphate buffer (pH 5.5). The eluate containing a desired product was concentrated to about 20 ml in vacuo. The concentrate was desalted by preparative HPLC utilizing ODS column, and the fraction eluted with 8% aqueous acetonitrile was concentrated to about 10 ml in vacuo and lyophilized to give 3-[(3-amino-4-{[(3-azetidinylamino)carbonyl]amino}-2-methyl-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate (220 mg) as an amorphous solid.

$^1$H-NMR(D$_2$O) δ 1.50 (3H, s), 1.51 (3H, s), 3.20 (1H, d, J=17.6 Hz), 3.47 (1H, d, J=17.6 Hz), 3.70 (3H, s), 4.18 (2H, dd, J=11.2, 7.6 Hz), 4.31 (2H, dd, J=11.2, 8.3 Hz), 4.68 (1H, tt, J=8.3, 7.6 Hz), 4.94 (1H, d, J=15.6 Hz), 5.15 (1H, d, J=15.6 Hz), 5.23 (1H, d, J=4.8 Hz), 5.83 (1H, d, J=4.8 Hz), 7.87 (1H, s)

Preparation 61

To a suspension of phenyl [1-methyl-5-(tritylamino)-1H-pyrazol-4-yl]carbamate (786 mg) and tert-butyl 3-pyrrolidinyl carbamate (373 mg) in methylene chloride (6 ml) was added N-ethyldiisopropylamine (0.43 ml), and the mixture was stirred under reflux for 10 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo to give tert-butyl [1-({[1-methyl-5-(tritylamino)-1H-pyrazol-4-yl]amino}carbonyl)-3-pyrrolidinyl]carbamate (730 mg) as a solid.

$^1$H-NMR(CDCl$_3$) δ 1.48 (9H, s), 1.82–1.88 (1H, m), 2.12–2.18 (1H, m), 2.89 (3H, s), 2.89–3.03 (1H, m), 3.20–3.30 (2H, m), 3.38–3.43 (1H, m), 4.22 (1H, br), 4.69 (1H, br), 4.88 (1H, brs), 4.96 (1H, brs), 7.18–7.27 (16H, m)

EXAMPLE 37

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (819 mg) in N,N-dimethylformamide (2.4 ml) was added N-(trimethylsilyl)acetamide (655 mg), and the mixture was stirred at room temperature for 30 minutes. To the reaction mixture was added a solution of tert-butyl [1-({[1-methyl-5-(tritylamino)-1H-pyrazol-4-yl]amino}carbonyl)-3-pyrrolidinyl]carbamate (567 mg) in N,N-dimethylformamide (3.0 ml). The whole mixture was stirred at room temperature for 3 hours. To the resulting reaction mixture were added ethyl acetate (100 ml) and water (50 ml). The aqueous layer was separated, and the organic layer was washed successively with 10% aqueous sodium trifluoroacetate solution, 10% aqueous sodium thiosulfate solution and brine, dried over sodium sulfate and filtered. The filtrate was concentrated to about 2.5 ml in vacuo. The concentrate was poured into diisopropyl ether (80 ml), and the resulting precipitate was collected by filtration and dried in vacuo. To a solution of the resulting solid in methylene chloride (2.55 ml) were added anisole (0.85 ml) and trifluoroacetic acid (2.55 ml), and the mixture was stirred at room temperature for 3 hours. The reaction mixture was poured into diisopropyl ether (80 ml), and the resulting precipitate was collected by filtration and dried in vacuo to give a crude product (608 mg), which was purified by preparative HPLC utilizing ODS column eluting with a mixture of acetonitrile and phosphate buffer (pH 5.5). The eluate containing a desired product was concentrated to about 20 ml in vacuo. The concentrate was desalted by preparative HPLC utilizing ODS column, and the fraction eluted with 7% acetonitrile/0.01 M hydrochloric acid was concentrated to about 10 ml in vacuo and lyophilized to give 3-[(3-amino-4-{[(3-amino-1-pyrrolidinyl)carbonyl]amino}-2-methyl-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate trihydrochloride (31 mg) as an amorphous solid.

$^1$H-NMR(D$_2$O) δ 1.61 (3H, s), 1.61 (3H, s), 2.13–2.27 (1H, m), 2.39–2.54 (1H, m), 3.29 (1H, d, J=18.1 Hz), 3.51 (1H, d, J=18.1 Hz), 3.55–3.68 (3H, m), 3.73 (3H, s), 3.80 (1H, dd, J=11.5, 6.0 Hz), 4.01–4.11 (1H, m), 5.20 (1H, d, J=16.0 Hz), 5.24 (1H, d, J=16.0 Hz), 5.28 (1H, d, J=4.8 Hz), 5.89 (1H, d, J=4.8 Hz), 7.91 (1H, s)

Preparation 62

To a suspension of phenyl [1-methyl-5-(tritylamino)-1H-pyrazol-4-yl]carbamate (711 mg) and tert-butyl 3-amino-1-pyrrolidinecarboxylate (372 mg) in methylenechloride (15 ml) was added N-ethyldiisopropylamine (0.51 ml), and the mixture was stirred under reflux for 17 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 10% methanol/methylenechloride to give tert-butyl 3-[({[1-methyl-5-(tritylamino)-1H-pyrazol-4-yl]amino}carbonyl)amino]-1-pyrrolidinecarboxylate (511 mg) as a solid.

$^1$H-NMR(CDCl$_3$) δ 1.46 (9H, s), 1.66–1.74 (1H, m), 2.04–2.11 (1H, m), 2.97 (3H, s), 3.05–3.11 (1H, m), 3.30–3.43 (2H, m), 3.53–3.58 (1H, m), 4.16–4.23 (2H, m), 4.45 (1H, brs), 4.74 (1H, br), 7.18–7.20 (6H, m), 7.28–7.30 (10H, m)

EXAMPLE 38

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (707 mg) in N,N-dimethylformamide (2.1 ml) was added N-(trimethylsilyl)acetamide (566 mg), and the mixture was stirred at room temperature for 30 minutes. To the reaction mixture was added a solution of tert-butyl 3-[({[1-methyl-5-(tritylamino)-1H-pyrazol-4-yl]amino}carbonyl)amino]-1-pyrrolidinecarboxylate (490 mg) in N,N-dimethylformamide (2.0 ml). The whole mixture was stirred at room temperature for 3 hours. To the resulting reaction mixture were added ethyl acetate (100 ml) and water (50 ml). The aqueous layer was separated, and the organic layer was washed successively with 10% aqueous sodium trifluoroacetate solution, 10% aqueous sodium thiosulfate solution and brine, dried over sodium sulfate and filtered. The filtrate was concentrated to about 3 ml in vacuo. The concentrate was poured into diisopropyl ether (80 ml), and the resulting precipitate was collected by filtration and dried in vacuo. To a solution of the resulting solid in methylene chloride (1.83 ml) were added anisole (0.61 ml), and trifluoroacetic acid (1.83 ml), and the mixture was stirred at room temperature for 5 hours. The reaction mixture was poured into diisopropyl ether (80 ml), and the resulting precipitate was collected by filtration and dried in vacuo to give a crude product (440 mg), which was purified by preparative HPLC utilizing ODS column. The eluate containing desired products was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 3-[(3-amino-2-methyl-4-{[(3-pyrrolidinylamino)carbonyl]amino}-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate (18 mg) as an amorphous solid.

$^1$H-NMR(D$_2$O) δ 1.54 (3H, s), 1.55 (3H, s), 2.00–2.10 (1H, m), 2.30–2.40 (1H, m), 3.23 (0.5H, d, J=17.9 Hz), 3.24 (0.5H, d, J=17.9 Hz), 3.27–3.34 (1H, m), 3.34–3.43 (1H, m), 3.45–3.57 (3H, m), 3.72 (3H, s), 4.36–4.46 (1H, m), 4.95 (0.5H, d, J=15.1 Hz), 4.96 (0.5H, d, J=15.6 Hz), 5.17 (1H, d, J=15.6 Hz), 5.26 (1H, d, J=5.0 Hz), 5.85 (1H, d, J=5.0 Hz), 7.88 (1H, s)

Preparation 63

To a suspension of tert-butyl {2-[({[1-methyl-5-(tritylamino)-1H-pyrazol-4-yl]amino}carbonyl)amino]

ethyl}carbamate (10.8 g) in methanol (50 ml) was added 4M hydrogen chloride solution in dioxane (50 ml). The mixture was stirred at room temperature for 3 hours. The solvent was concentrated in vacuo, and the residue was triturated with ethyl acetate and dried in vacuo to give N-(2-aminoethyl)-N'-(5-amino-1-methyl-1H-pyrazol-4-yl)urea trihydrochloride (5.6 g) as a solid.

$^1$H-NMR(DMSO-d$_6$) δ 2.84–2.87 (2H, m), 3.30 (2H, brs), 3.71 (3H, s), 6.57 (1H, br), 7.91 (1H, s), 8.05 (4H, br), 8.55 (1H, br)

Preparation 64

To a solution of N-(2-aminoethyl)-N'-(5-amino-1-methyl-1H-pyrazol-4-yl)urea trihydrochloride (3.1 g) and triethylamine (4.6 g) in chloroform (100 ml) was added di-tert-butyl ({[(trifluoromethyl)sulfonyl]imino}methylene)biscarbamate (5.9 g). The mixture was stirred at room temperature for 90 minutes. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was triturated with ethyl acetate to give di-tert-butyl ((Z)-{[2-({[(5-amino-1-methyl-1H-pyrazol-4-yl)amino]carbonyl}amino)ethyl]amino}methylidene)biscarbamate (4.3 g) as a solid.

$^1$H-NMR(DMSO-d$_6$) δ 1.39 (9H, s), 1.48 (9H, s), 3.18 (2H, q, J=6.0 Hz), 3.35 (2H, br), 3.49 (3H, s), 4.77 (1H, brs), 6.05 (1H, br), 6.97 (1H, s), 7.19 (1H, brs), 8.36 (1H, t, J=5.5 Hz), 11.49 (1H, brs)

Preparation 65

To a solution of di-tert-butyl ((Z)-{[2-({[(5-amino-1-methyl-1H-pyrazol-4-yl)amino]carbonyl}amino)ethyl]amino}methylidene)biscarbamate (2.2 g) and triethylamine (0.6 g) in chloroform (30 ml) was added trityl chloride (1.7 g), and the mixture was stirred at room temperature for 14 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was triturated with ethyl acetate to give di-tert-butyl [(Z)-({2-[({[1-methyl-5-(tritylamino)-1H-pyrazol-4-yl]amino}carbonyl)amino]ethyl}amino)methylidene]biscarbamate (1.9 g) as a solid.

$^1$H-NMR(DMSO-d$_6$) δ 1.39 (9H, s), 1.47 (9H, s), 2.72 (3H, s), 3.09–3.10 (2H, m), 3.31–3.34 (2H, m), 5.69 (1H, s), 6.10 (1H, br), 6.77 (1H, brs), 7.02 (1H, s), 7.14–7.16 (6H, m), 7.22–7.27 (9H, m), 8.36 (1H, t, J=5.5 Hz), 11.51 (1H, brs)

EXAMPLE 39

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (820 mg) in N,N-dimethylformamide (1.4 ml) was added N-(trimethylsilyl)acetamide (656 mg), and the mixture was stirred at room temperature for 30 minutes. To the reaction mixture were added di-tert-butyl [(Z)-({2-[({[1-methyl-5-(tritylamino)-1H-pyrazol-4-yl]amino}carbonyl)amino]ethyl}amino)methylidene]biscarbamate (820 mg) and N,N-dimethylformamide (2.0 ml). The whole mixture was stirred at room temperature for 3 hours. To the resulting reaction mixture were added ethyl acetate (100 ml) and water (50 ml). The aqueous layer was separated, and the organic layer was washed successively with 10% aqueous sodium trifluoroacetate solution, 10% aqueous sodium thiosulfate solution and brine, dried over sodium sulfate and filtered. The filtrate was concentrated to about 5 ml in vacuo. The concentrate was poured into diisopropyl ether (120 ml), and the resulting precipitate was collected by filtration and dried in vacuo. To a solution of the resulting solid in methylene chloride (3.0 ml) were added anisole (1.0 ml) and trifluoroacetic acid (2.0 ml), and the mixture was stirred at room temperature for 4 hours. The reaction mixture was poured into diisopropyl ether (100 ml), and the resulting precipitate was collected by filtration and dried in vacuo to give a crude product (740 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 3-{[3-amino-4-({[(2-guanidinoethyl)amino]carbonyl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (70 mg) as an amorphous solid.

$^1$H-NMR(D$_2$O) δ 1.55 (3H, s), 1.56 (3H, s), 3.24 (1H, d, J=17.6 Hz), 3.28–3.40 (4H, m), 3.52 (1H, d, J=17.6 Hz), 3.73 (3H, s), 4.97 (1H, d, J=15.4 Hz), 5.16 (1H, d, J=15.4 Hz), 5.27 (1H, d, J=4.8 Hz), 5.84 (1H, d, J=4.8 Hz), 7.87 (1H, s)

Preparation 66

To a suspension of phenyl [1-methyl-5-(tritylamino)-1H-pyrazol-4-yl]carbamate (950 mg) and tert-butyl (3S)-3-pyrrolidinylcarbamate (560 mg) in methylene chloride (20 ml) was added N-ethyldiisopropylamine (390 mg), and the mixture was stirred under reflux for 23 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 4% methanol/chloroform to give tert-butyl [(3S)-1-({[1-methyl-5-(tritylamino)-1H-pyrazol-4-yl]amino}carbonyl)-3-pyrrolidinyl]carbamate (680 mg) as a solid.

$^1$H-NMR(CDCl$_3$) δ 1.48 (9H, s), 1.82–1.88 (1H, m), 2.12–2.18 (1H, m), 2.89 (3H, s), 2.89–3.03 (1H, m), 3.20–3.30 (2H, m), 3.38–3.43 (1H, m), 4.22 (1H, br), 4.69 (1H, br), 4.88 (1H, brs), 4.96 (1H, brs), 7.18–7.27 (16H, m)

EXAMPLE 40

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (820 mg) in N,N-dimethylformamide (2.4 ml) was added N-(trimethylsilyl)acetamide (656 mg), and the mixture was stirred at room temperature for 30 minutes. To the reaction mixture was added tert-butyl [(3S)-1-({[1-methyl-5-(tritylamino)-1H-pyrazol-4-yl]amino}carbonyl)-3-pyrrolidinyl]carbamate (680 mg). The whole mixture was stirred at room temperature for 3 hours. To the resulting reaction mixture were added ethyl acetate (80 ml) and water (50 ml). The aqueous layer was separated, and the organic layer was washed successively with 10% aqueous sodium trifluoroacetate solution, 10% aqueous sodium thiosulfate solution and brine, dried over sodium-sulfate and filtered. The filtrate was concentrated to about 5 ml in vacuo. The concentrate was poured into diisopropyl ether (120 ml), and the resulting precipitate was collected by filtration and dried in vacuo. To a solution of the resulting solid in methylene chloride (3.0 ml) were added anisole (1.0 ml) and trifluoroacetic acid (2.0 ml), and the mixture was stirred at room temperature for 4 hours. The reaction mixture was poured into diisopropyl ether (100 ml), and the resulting precipitate was collected by filtration and dried in vacuo to give a crude product (690 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 3-{[3-amino-4-({[(3S)-3-amino-1-pyrrolidinyl]carbonyl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (60 mg) as an amorphous solid.

$^1$H-NMR(D$_2$O) δ 1.52 (6H, s), 2.13–2.27 (1H, m), 2.38–2.53 (1H, m), 3.20 (1H, d, J=17.4 Hz), 3.46 (1H, d, J=17.4 Hz), 3.54–3.67 (3H, m), 3.73 (3H, s), 3.79 (1H, dd, J=11.5, 6.0 Hz), 4.00–4.10 (1H, m), 4.97 (1H, d, J=15.4 Hz), 5.16 (1H, d, J=15.4 Hz), 5.25 (1H, d, J=4.8 Hz), 5.83 (1H, d, J=4.8 Hz), 7.85 (1H, s)

Preparation 67

To a suspension of phenyl [1-methyl-5-(tritylamino)-1H-pyrazol-4-yl]carbamate (950 mg) and tert-butyl (3R)-3-pyrrolidinylcarbamate (560 mg) in methylene chloride (20 ml) was added N-ethyldiisopropylamine (390 mg), and the mixture was stirred under reflux for 23 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 4% methanol/chloroform to give tert-butyl [(3R)-1-({[1-methyl-5-(tritylamino)-1H-pyrazol-4-yl]amino}carbonyl)-3-pyrrolidinyl]carbamate (700 mg) as a solid.

$^1$H-NMR(CDCl$_3$) δ 1.48 (9H, s), 1.82–1.88 (1H, m), 2.12–2.18 (1H, m), 2.89 (3H, s), 2.89–3.03 (1H, m), 3.20–3.30 (2H, m), 3.38–3.43 (1H, m), 4.22 (1H, br), 4.69 (1H, br), 4.88 (1H, brs), 4.96 (1H, brs), 7.18–7.27 (16H, m)

EXAMPLE 41

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (820 mg) in N,N-dimethylformamide (2.4 ml) was added N-(trimethylsilyl)acetamide (656 mg), and the mixture was stirred at room temperature for 30 minutes. To the reaction mixture was added tert-butyl [(3R)-1-({[1-methyl-5-(tritylamino)-1H-pyrazol-4-yl]amino}carbonyl)-3-pyrrolidinyl]carbamate (680 mg). The whole mixture was stirred at room temperature for 3 hours. To the resulting reaction mixture were added ethyl acetate (80 ml) and water (50 ml). The aqueous layer was separated, and the organic layer was washed successively with 10% aqueous sodium trifluoroacetate solution, 10% aqueous sodium thiosulfate solution and brine, dried over sodium sulfate and filtered. The filtrate was concentrated to about 5 ml in vacuo. The concentrate was poured into diisopropyl ether (120 ml), and the resulting precipitate was collected by filtration and dried in vacuo. To a solution of the resulting solid in methylene chloride (3.0 ml) were added anisole (1.0 ml) and trifluoroacetic acid (2.0 ml), and the mixture was stirred at room temperature for 4 hours. The reaction mixture was poured into diisopropyl ether (100 ml), and the resulting precipitate was collected by filtration and dried in vacuo to give a crude product (760 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 3-{[3-amino-4-({[(3R)-3-amino-1-pyrrolidinyl]carbonyl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (68 mg) as an amorphous solid.

$^1$H-NMR(D$_2$O) δ 1.52 (6H, s), 2.13–2.27 (1H, m), 2.38–2.53 (1H, m), 3.20 (1H, d, J=17.6 Hz), 3.47 (1H, d, J=17.6 Hz), 3.56–3.66 (3H, m), 3.73 (3H, s), 3.79 (1H, dd, J=11.0, 6.0 Hz), 4.00–4.10 (1H, m), 4.96 (1H, d, J=15.1 Hz), 5.15 (1H, d, J=15.1 Hz), 5.26 (1H, d, J=4.8 Hz), 5.83 (1H, d, J=4.8 Hz), 7.84 (1H, s)

Preparation 68

To a suspension of phenyl (5-amino-1-methyl-1H-pyrazol-4-yl)carbamate (1.86 g) and (3S)-1-benzyl-3-pyrrolidinamine (2.0 g) in chloroform (50 ml) was added N-ethyldiisopropylamine (3.1 g), and the mixture was stirred under reflux for 19 hours. The reaction mixture was concentrated in vacuo to give crude (S)-5-amino-4-[3-(1-benzyl-3-pyrrolidinyl)ureido]-1-methyl-1H-pyrazole as a solid. A solution of the crude product in acetic acid was treated with palladium black (3 ml) under a hydrogen atomosphere at room temperature for 24 hours. After the catalyst was filtered off, the filtrate was concentrated in vacuo, and the residue was dissolved in, saturated aqueous sodium hydrogen carbonate solution (100 ml). To the solution was added a solution of di-tert-butyl dicarbonate (5.0 g) in tetrahydrofuran (40 ml), and the mixture was stirred at room temperature for 5 hours. The reaction mixture was extracted with chloroform. The organic layer was dried over anhydrous magnesium sulfate, filtered and concentrated in vacuo. The residue was triturated with diethyl ether to give tert-butyl (3S)-3-({[(5-amino-1-methyl-1H-pyrazol-4-yl)amino]carbonyl}amino)-1-pyrrolidinecarboxylate (1.9 g) as a solid.

$^1$H-NMR(DMSO-d$_6$) δ 1.40 (9H, s), 1.70–1.76 (1H, m), 1.95–2.02 (1H, m), 3.01–3.05 (1H, m), 3.24–3.34 (2H, m), 3.38–3.45 (1H, m), 3.50 (3H, s), 4.06–4.11 (1H, m), 4.78 (2H, brs), 6.19 (1H, brs), 6.97 (1H, s), 7.09 (1H, brs)

Preparation 69

To a solution of tert-butyl (3S)-3-({[(5-amino-1-methyl-1H-pyrazol-4-yl)amino]carbonyl}amino)-1-pyrrolidinecarboxylate (1.8 g) and N-ethyldiisopropylamine (720 mg) in chloroform (50 ml) was added trityl chloride (1.6 g), and the mixture was stirred at room temperature for 28 hours. The reaction mixture was washed successively with 10% aqueous citric acid solution, brine and saturated aqueous sodium hydrogen carbonate solution. The organic layer was dried over anhydrous magnesium sulfate, filtered and concentrated in vacuo. The residue was purified by column chromatography on silica gel eluting with 3% methanol/chloroform to give tert-butyl (3S)-3-[({[1-methyl-5-(tritylamino)-1H-pyrazol-4-yl]amino}carbonyl)amino]-1-pyrrolidinecarboxylate (1.7 g) as a solid.

$^1$H-NMR(CDCl$_3$) δ 1.46 (9H, s), 1.66–1.74 (1H, m), 2.04–2.11 (1H, m), 2.97 (3H, s), 3.05–3.11 (1H, m), 3.30–3.43 (2H, m), 3.53–3.58 (1H, m), 4.16–4.23 (2H, m), 4.45 (1H, brs), 4.74 (1H, br), 7.18–7.20 (6H, m), 7.28–7.30 (10H, m)

EXAMPLE 42

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (820 mg) in N,N-dimethylformamide (2.4 ml) was added N-(trimethylsilyl)acetamide (656 mg), and the mixture was stirred at room temperature for 30 minutes. To the reaction mixture was added tert-butyl (3S)-3-[({[1-methyl-5-(tritylamino)-1H-pyrazol-4-yl]amino}carbonyl)amino]-1-pyrrolidinecarboxylate (680 mg). The whole mixture was stirred at room temperature for 3 hours. To the resulting reaction mixture were added ethyl acetate (80 ml) and water (50 ml). The aqueous layer was separated, and the organic layer was washed successively with 10% aqueous sodium trifluoroacetate solution, 10% aqueous sodium thiosulfate solution and brine, dried over sodium sulfate and filtered. The filtrate was concentrated to about 5 ml in vacuo. The concentrate was poured into diisopropyl ether (120 ml), and the resulting precipitate was collected by filtration and dried in vacuo. To a solution of the resulting solid in methylene chloride (3.0 ml) were added anisole (1.0 ml) and trifluoroacetic acid (2.0 ml), and the mixture was stirred at room temperature for 5 hours. The reaction mixture was poured into diisopropyl ether (100 ml), and the resulting precipitate was collected by filtration and dried in vacuo to give a crude product (870 mg), which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 3-{[3-amino-2-methyl-4-({[(3S)-3-pyrrolidinylamino]carbonyl}amino)-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate (68 mg) as an amorphous solid.

$^1$H-NMR(D$_2$O) δ 1.52 (3H, s), 1.53 (3H, s), 2.00–2.09 (1H, m), 2.28–2.38 (1H, m), 3.22 (1H, d, J=17.4 Hz), 3.29 (1H, dd, J=12.4, 4.6 Hz), 3.34–3.42 (1H, m), 3.44–3.54 (3H, m), 3.71 (3H, s), 4.36–4.43 (1H, m), 4.95 (1H, d, J=15.6 Hz), 5.15 (1H, d, J=15.6 Hz), 5.25 (1H, d, J=4.6 Hz), 5.84 (1H, d, J=4.6 Hz), 7.87 (1H, s)

Preparation 70

To a suspension of 4-[(tert-butoxycarbonyl)amino]butanoic acid (2.13 g) in dichloromethane (40 ml) was added 1-hydroxybenzotriazole (HOBT) (1.41 g) and N-(3-dimethylaminopropyl)-N'-ethylcarbodiimide hydrochloride (WSCD HCl) (3.65 g), and the mixture was stirred for 1 hour. To the solution were added 1-methyl-1H-pyrazole-4,5-diamine sulfate (2 g) and N,N-diisopropylethylamine (3.32 ml). The reaction mixture was stirred for 18 hours. To the resulting solution were added brine and saturated aqueous sodium hydrogen carbonate solution, and the mixture was extracted with ethyl acetate. The aqueous layer was extracted with tetrahydrofuran/ethyl acetate=1/1 twice. The extract was dried over anhydrous magnesium sulfate, filtered and concentrated in vacuo. To the residue was added pyridine (40 ml), and then added chlorotriphenylmethane (5.3 g). The mixture was stirred at 65° C. for 6 hours. The mixture was dissolved in ethyl acetate. The solution was washed successively with water, 10% aqueous citric acid solution, water and brine. The extract was dried over anhydrous magnesium sulfate, filtered and concentrated in vacuo. The residue was purified by column chromatography on silica gel eluting with 60% ethyl acetate/dichloromethane to give tert-butyl (4-{[1-methyl-5-(tritylamino)-1H-pyrazol-4-yl]amino}-4-oxobutyl)carbamate (2.01 g).

$^1$H-NMR(CDCl$_3$) δ 1.44 (9H, s), 1.67 (2H, tt, J=6.7, 6.7 Hz), 1.92 (2H, t, J=6.7 Hz), 2.90 (3H, s), 3.09 (2H, dt, J=6.7, 6.7 Hz), 4.50 (1H, s), 4.71 (1H, t, J=6.7 Hz), 6.53 (1H, s), 7.0–7.35 (16H, m), 7.56 (1H, s)

EXAMPLE 43

To a solution of benzhydryl 7β-[(Z)-2-(5-amino-1,2,4-thiadiazol-3-yl)-2-(1-tert-butoxycarbonyl-1-methylethoxyimino)acetamido]-3-iodomethyl-3-cephem-4-carboxylate (2 g) in N,N-dimethylformamide (6 ml) was added N-(trimethylsilyl)acetamide (1.77 g), and the mixture was stirred at room temperature for 30 minutes. To the reaction mixture was added tert-butyl (4-{[1-methyl-5-(tritylamino)-1H-pyrazol-4-yl]amino}-4-oxobutyl)carbamate (1.98 g), and the whole mixture was stirred at 35° C. for 30 hours. To the resulting reaction mixture was added ethyl acetate, and the solution was washed successively with water, 10% aqueous sodium trifluoroacetate solution and brine, dried over magnesium sulfate and filtered. The filtrate was concentrated to about 25 ml in vacuo. The concentrate was poured into diisopropyl ether (150 ml), and the resulting precipitate was collected by filtration and dried in vacuo. To a solution of the solid in methylene chloride (5 ml) were added anisole (1.5 ml) and trifluoroacetic acid (5 ml). The resulting solution was stirred at room temperature for 4 hours and poured into diisopropyl ether. The resulting precipitate was collected by filtration and dried in vacuo to give a crude product (1.2 g). The crude product was dissolved in a mixture of phosphate buffer (pH 6.86, 10 ml) and saturated aqueous sodium hydrogen carbonate solution and purified by preparative HPLC utilizing ODS column. The eluate containing a desired product was concentrated to about 20 ml in vacuo. The concentrate was adjusted to about pH 3 with concentrated hydrochloric acid and chromatographed on Diaion® HP-20 (Mitsubishi Chemical Corporation) eluting with 20% aqueous 2-propanol. The eluate was concentrated to about 30 ml in vacuo, and 2M aqueous sulfuric acid solution (72 ml) was added. The mixture was lyophilized to give 3-({3-amino-4-[(4-aminobutanoyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylic acid hydrogen sulfate (113 mg) as an amorphous solid.

$^1$H-NMR(D$_2$O) δ 1.61 (6H, s), 2.01 (2H, tt, J=7.6, 7.6 Hz), 2.58 (2H, t, J=7.6 Hz), 3.07 (2H, t, J=7.6 Hz), 3.23 (1H, d, J=18 Hz), 3.45 (1H, d, J=18 Hz), 3.72 (3H, s), 5.06 (1H, d, J=15.7 Hz), 5.25 (1H, d, J=4.8 Hz), 5.28 (1H, d, J=15.7 Hz), 5.87 (1H, d, J=4.8 Hz), 8.03 (1H, s)

Preparation 71 tert-Butyl (5-{[1-methyl-5-(tritylamino)-1H-pyrazol-4-yl]amino}-5-oxopentyl)carbamate The title compound was obtained from 5-[(tert-butoxycarbonyl)amino]pentanoic acid in the same manner as in Preparation 70.

$^1$H-NMR(CDCl$_3$) δ 1.43 (9H, s), 1.2–1.6 (4H, m), 1.90 (2H, t, J=7.0 Hz), 2.90 (3H, s), 3.09 (2H, dt, J=7.0, 7.0 Hz), 4.52 (1H, s), 4.61 (1H, t, J=7.0 Hz), 6.28 (1H, s), 7.0–7.35 (16H, m), 7.59 (1H, s)

EXAMPLE 44

3-({3-Amino-4-[(5-aminopentanoyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylic acid hydrogen sulfate The title compound was obtained from tert-butyl (5-{[1-methyl-5-(tritylamino)-1H-pyrazol-4-yl]amino}-5-oxopentyl)carbamate in the same manner as in Example 43.

$^1$H-NMR(D$_2$O) δ 1.61 (6H, s), 1.65–1.8 (4H, m), 2.50 (2H, m), 3.02 (2H, m), 3.23 (1H, d, J=18 Hz), 3.45 (1H, d, J=18 Hz), 3.72 (3H, s), 5.06 (1H, d, J=15.7 Hz), 5.25 (1H, d, J=4.8 Hz), 5.28 (1H, d, J=15.7 Hz), 5.87 (1H, d, J=4.8 Hz), 8.02 (1H, s)

Preparation 72

To a solution of 1-methyl-N$^5$-trityl-1H-pyrazole-4,5-diamine (4 g) in dichloromethane (100 ml) was added tert-butyl 4-{[(2,5-dioxo-1-pyrrolidinyl)oxy]carbonyl}-1-piperidinecarboxylate (4.05 g), and the mixture was refluxed for 72 hours. The reaction mixture was washed successively with water 10% aqueous citric acid solution, water and brine. The extract was dried over anhydrous magnesium sulfate, filtered and concentrated in vacuo to give tert-butyl 4-({[1-methyl-5-(tritylamino)-1H-pyrazol-4-yl]amino}carbonyl)-1-piperidinecarboxylate (1.806 g).

$^1$H-NMR(CDCl$_3$) δ 1.3–1.9 (14H, m), 1.5–1.8 (2H, m), 2.95 (3H, s), 4.10 (2H, m), 4.36 (1H, s), 6.53 (1H, s), 7.0–7.35 (16H, m), 7.68 (1H, s)

EXAMPLE 45

3-({3-Amino-2-methyl-4-[(4-piperidinylcarbonyl)amino]-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl 4-({[1-methyl-5-(tritylamino)-1H-pyrazol-4-yl]amino}carbonyl)-1-piperidinecarboxylate in the same manner as in Example 36.

$^1$H-NMR(D$_2$O) δ 1.57 (6H, s), 1.8–2.3 (4H, m), 2.7–3.6 (7H, m), 3.72 (3H, s), 5.06 (1H, d, J=15.7 Hz), 5.25 (1H, d, J=4.8 Hz), 5.28 (1H, d, J=15.7 Hz), 5.87 (1H, d, J=4.8 Hz), 8.01 (1H, s)

Preparation 73

To a suspension of 3-[N-(tert-butoxycarbonyl)-N-methylamino]propanoic acid (3.33 g) in dichloromethane (33 ml) and tetrahydrofuran (33 ml) were added HOBT (3.33 g) and WSC HCl (6.29 g), and the mixture was stirred for 1 hour. To the solution were added 1-methyl-1H-pyrazole-4,5-diamine sulfate (3.45 g) and N,N-diisopropylethylamine (11.4 ml). The reaction mixture was stirred at room temperature overnight. To the resulting solution was added brine and extracted with tetrahydrofuran/ethyl acetate=1/1. The extract was dried over anhydrous magnesium sulfate, filtered and concentrated in vacuo to give tert-butyl N-{3-[(5-amino-1-methyl-1H-pyrazol-4-yl)amino]-3-oxopropyl}-N-methylcarbamate as an oil (2.4 g). This product was used in the next step without further purification.

Preparation 74

To a solution of tert-butyl N-{3-[(5-amino-1-methyl-1H-pyrazol-4-yl)amino]-3-oxopropyl}-N-methylcarbamate (4.88 g) in N,N-dimethylformamide (50 ml) were added trityl chloride (6.86 g), triethylamine (6.86 ml) and 4-dimethylaminopyridine (80 mg) succesively. The mixture was stirred at room temperature overnight. To the resulting mixture was added ethyl acetate and washed with water (three times) and brine. The organic layer was dried over anhydrous magnesium sulfate, filtered and concentrated in vacuo. The residue was purified by column chromatography on silica gel to give tert-butyl N-methyl-N-(3-{[1-methyl-5-(tritylamino)-1H-pyrazol-4-yl]amino}-3-oxopropyl)carbamate (4.20 g) as an amorphous solid.

IR(KBr) 1659, 1587, 1491, 1446, 1173, 1151, 762, 739, 708 cm$^{-1}$ $^1$H-NMR(DMSO-d$_6$) δ 1.40 (9H, s), 2.12 (2H, t, J=7.4 Hz), 2.74 (3H, s), 2.74 (3H, s), 3.24 (2H, t, J=7.4 Hz), 5.58 (1H, s), 7.13–7.40 (16H, m), 8.30 (1H, s)

EXAMPLE 46

3-[(3-Amino-2-methyl-4-{[3-(methylamino)propanoyl]amino}-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl N-methyl-N-(3-{[1-methyl-5-(tritylamino)-1H-pyrazol-4-yl]amino}-3-oxopropyl)carbamate in the same manner as in Example 32 as an amorphous solid.

IR(KBr) 1770, 1664, 1599, 1531, 1400, 1360 cm$^{-1}$ $^1$H-NMR(D$_2$O) δ 1.53 (6H, s), 2.77 (3H, s), 2.92 (2H, t, J=6.5 Hz), 3.19 and 3.45 (2H, ABq, J=17.7 Hz), 3.74 (3H, s), 5.00 and 5.21 (2H, ABq, J=15.4 Hz), 5.25 (1H, d, J=4.8 Hz), 5.85 (1H, d, J=4.8 Hz), 8.02 (1H, s)

ESI-MS 666.3 (M+H$^+$)

Preparation 75 tert-Butyl 3-{[(5-amino-1-methyl-1H-pyrazol-4-yl)amino]carbonyl}-1-azetidinecarboxylate The title compound was obtained from 1-(tert-butoxycarbonyl)-3-azetidinecarboxylic acid in the same manner as in Preparation 73 as an oil. This product was used in the next step without further purification.

Preparation 76 tert-Butyl 3-({[1-methyl-5-(tritylamino)-1H-pyrazol-4-yl]amino}carbonyl)-1-azetidinecarboxylate The title compound was obtained from tert-butyl 3-{[(5-amino-1-methyl-1H-pyrazol-4-yl)amino]carbonyl}-1-azetidinecarboxylate in the same manner as in Preparation 74 as an amorphous solid.

IR(KBr) 3367, 3321, 1701, 1662, 1489, 1414, 1144, 766, 704 cm$^{-1}$ $^1$H-NMR(DMSO-d$_6$) δ 1.39 (9H, s), 2.75 (3H, s), 2.97–3.05 (1H, m), 3.63–3.70 (2H, m), 3.82–3.90 (2H, m), 5.57 (1H, s), 7.10–7.33 (16H, m), 8.41 (1H, s)

ESI-MS 560.3 (M+Na$^+$)

EXAMPLE 47

3-({3-Amino-4-[(3-azetidinylcarbonyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl 3-({[1-methyl-5-(tritylamino)-1H-pyrazol-4-yl]amino}carbonyl)-1-azetidinecarboxylate in the same manner as in Example 32 as an amorphous solid.

IR(KBr) 1768, 1663, 1624, 1605, 1406, 1362 cm$^{-1}$ $^1$H-NMR(D$_2$O) δ 1.53 (3H, s), 1.53 (3H, s), 3.19 and 3.50 (2H, ABq, J=17.7 Hz), 3.82–3.98 (1H, m), 4.31–4.35 (4H, m), 4.49 and 5.20 (2H, ABq, J=15.3 Hz), 5.25 (1H, d, J=4.8 Hz), 5.85 (1H, d, J=4.8 Hz), 8.04 (1H, s)

ESI-MS 664.2 (M+H$^+$)

Preparation 77 tert-Butyl N-{2-[(5-amino-1-methyl-1H-pyrazol-4-yl)amino]-2-oxoethyl}-N-methylcarbamate The title compound was obtained from [N-(tert-butoxycarbonyl)-N-(methyl)amino]acetic acid in the same manner as in Preparation 73 as an oil. This product was used in the next step without further purification.

Preparation 78 tert-Butyl N-methyl-N-(2-{[1-methyl-5-(tritylamino)-1H-pyrazol-4-yl]amino}-2-oxoethyl)carbamate The title compound was obtained from tert-butyl N-{2-[(5-amino-1-methyl-1H-pyrazol-4-yl)amino]-2-oxoethyl}-N-methylcarbamate in the same manner as in Preparation 74 as a white solid. The NMR spectrum of this compound indicates the existence of its rotamer.

$^1$H-NMR(DMSO-d$_6$) δ 1.32 and 1.39 (9H, s), 2.72 and 2.77 (3H, s), 3.52 and 3.61 (2H, brs), 5.61 (1H, s), 7.13–7.33 (16H, m), 8.20 and 8.30 (1H, brs)

ESI-MS 548.3 (M+Na$^+$)

EXAMPLE 48

3-[(3-Amino-2-methyl-4-{[(methylamino)acetyl]amino}-1-pyrazolio)methyl]-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl N-methyl-N-(2-{[1-methyl-5-(tritylamino)-1H-pyrazol-4-yl]amino}-2-oxoethyl)carbamate in the same manner as in Example 32 as an amorphous solid.

IR(KBr) 1770, 1657, 1601, 1400, 1362 cm$^{-1}$ $^1$H-NMR(D$_2$O) δ 1.53 (6H, s), 2.82 (3H, s), 3.18 and 3.45 (2H, ABq, J=17.7 Hz), 3.74 (3H, s), 4.08 (2H, s), 5.00 and 5.20 (2H, ABq, J=15.3 Hz), 5.25 (1H, d, J=4.8 Hz), 5.84 (1H, d, J=4.8 Hz), 8.05 (1H, s)

ESI-MS 652.2 (M+H$^+$)

Preparation 79

N-(5-Amino-1-methyl-1H-pyrazol-4-yl)-2-(1,3-dioxo-1,3-dihydro-2H-isoindol-2-yl)acetamide The title compound was obtained from (1,3-dioxo-1,3-dihydro-2H-isoindol-2-yl)acetic acid in the same manner as in Preparation 73 as a solid.

$^1$H-NMR(DMSO-d$_6$) δ 3.55 (3H, s), 4.36 (2H, s), 4.91 (2H, brs), 7.14 (1H, s), 7.85–8.02 (4H, m), 9.48 (1H, s)

ESI-MS 322.2 (M+Na$^+$)

Preparation 80

2-(1,3-Dioxo-1,3-dihydro-2H-isoindol-2-yl)-N-[1-methyl-5-(tritylamino)-1H-pyrazol-4-yl]acetamide The title compound was obtained from N-(5-amino-1-methyl-1H-pyrazol-4-yl)-2-(1,3-dioxo-1,3-dihydro-2H-isoindol-2-yl)acetamide in the same manner as in Preparation 74 as a solid.

$^1$H-NMR(DMSO-d$_6$) δ 2.70 (3H, s), 4.12 (2H, s), 5.41 (1H, s), 7.12–7.33 (16H, m), 7.85–7.95 (4H, m), 8.93 (1H, s)

ESI-MS 564.3 (M+Na$^+$)

Preparation 81

Hydrazine monohydrate (1.46 ml) was added to a solution of 2-(1,3-dioxo-1,3-dihydro-2H-isoindol-2-yl)-N-[1-methyl-5-(tritylamino)-1H-pyrazol-4-yl]acetamide (5.42 g) in ethanol (108 ml) and tetrahydrofuran (54 ml) at room temperature, and the mixture was stirred at 70° C. for 2 hours. The reaction mixture was cooled to 0° C., and the insoluble materials were removed by filtration. The filtrate was concentrated in vacuo. The residue was triturated with diisopropyl ether, collected by filtration and dried in vacuo to give 2-amino-N-[1-methyl-5-(tritylamino)-1H-pyrazol-4-yl]acetamide (3.37 g) as a solid. This product was used in the next step without further purification.

Preparation 82

To a solution of 2-amino-N-[1-methyl-5-(tritylamino)-1H-pyrazol-4-yl]acetamide (2.47 g) in tetrahydrofuran (50 ml) were added di-tert-butyl ({[(trifluoromethyl)sulfonyl]imino}methylene)biscarbamate (2.35 g) and triethylamine (2.5 ml), and the mixture was stirred at room temperature for 30 minutes. The reaction mixture was poured into a mixture of ethyl acetate and water. The aqueous layer was separated, and the organic layer was washed with brine, dried over anhydrous magnesium sulfate and filtered. The filtrate was concentrated in vacuo. The concentrate was purified by silica gel column chromatography to give di-tert-butyl {(E)-[(2-{[-methyl-5-(tritylamino)-1H-pyrazol-4-yl]amino}-2-oxoethyl)amino]methylidene}biscarbamate (3.25 g) as an amorphous solid.

$^1$H-NMR(DMSO-$d_6$) δ 1.38 (9H, s), 1.49 (9H, s), 2.75 (3H, s), 3.79 (2H, d, J=4.7 Hz), 5.47 (1H, s), 7.12–7.33 (16H, m), 8.55 (1H, t, J=4.7 Hz), 8.61 (1H, s), 11.43 (1H, s)

ESI-MS 676.3 (M+Na$^+$)

EXAMPLE 49

3-({3-Amino-4-[(guanidinoacetyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from di-tert-butyl {(E)-[(2-{[1-methyl-5-(tritylamino)-1H-pyrazol-4-yl]amino}-2-oxoethyl)amino]methylidene}biscarbamate in the same manner as in Example 32 as an amorphous solid.

IR(KBr) 1770, 1668, 1655, 1620, 1601, 1402, 1363 cm$^{-1}$ $^1$H-NMR(D$_2$O) δ 1.53 (6H, s), 3.20 and 3.48 (2H, ABq, J=17.6 Hz), 3.75 (3H, s), 4.21 (2H, s), 5.00 and 5.20 (2H, ABq, J=15.3 Hz), 5.26 (1H, d, J=4.8 Hz), 5.85 (1H, d, J=4.8 Hz), 8.02 (1H, s)

ESI-MS 678.2 (M–H$^+$) (negative)

EXAMPLE 50

To a solution of 3-({3-amino-4-[(3-aminopropanoyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate (652 mg) in water (30 ml) and acetonitrile (3 ml) were added ethyl formimidate hydrochloride (658 mg) and potassium carbonate (1.106 g) under ice cooling. After stirring at 5° C. for 3 hours, 1N HCl was added to neutralize the reaction mixture. The resulting solution was purified, by preparative HPLC eluting with a mixture of phosphate buffer (pH 5.5) and acetonitrile, and the eluate was subjected to column chromatography on Diaion® HP20 (Mitsubishi Chemical Corporation) and lyophilized to give 3-({3-amino-4-[(3-guanidinoptopanoyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate (23 mg) as an amorphous. The NMR spectrum of this compound indicates the existence of its rotamer. Only major isomer was described.

IR(KBr) 1770, 1714, 1668, 1653, 1456, 1400, 1360 cm$^{-1}$ $^1$H-NMR(D$_2$O) δ 1.53 (6H, s), 2.85 (2H, t, J=6.4 Hz), 3.19 and 3.46 (2H, ABq, J=17.7 Hz), 3.65 (2H, t, J=6.4 Hz), 5.00 and 5.21 (2H, ABq, J=15.2 Hz), 5.26 (1H, d, J=4.8 Hz), 5.85 (1H, d, J=4.8 Hz), 7.80 (1H, s), 8.01 (1H, s)

ESI-MS 677.2 (M–H$^+$) (negative)

Preparation 83

To a stirred solution of 1-methyl-1H-pyrazole-4,5-diamine sulfate (2.1 g) and 3-ethoxy-3-oxopropanoic acid (1.32 g) in dichloromethane (10 ml) and tetrahydrofuran (10 ml) was added WSCD HCl (3.83 g) and N,N-diisopropylethylamine (6.96 ml), and the mixture was stirred overnight. The solvent was removed under reduced pressure, and the crude residue which includes ethyl 3-[(5-amino-1-methyl-1H-pyrazol-4-yl)amino]-3-oxopropanoate was used for the next reaction without further purification.

Preparation 84

The crude residue containing ethyl 3-[(5-amino-1-methyl-1H-pyrazol-4-yl)amino]-3-oxopropanoate was dissolved in N,N-dimethylformamide (20 ml), and trityl chloride (5.52 g) and triethylamine (4.14 ml) were added with stirring. The mixture was stirred overnight and quenched with water (10 ml). The whole mixture was extracted with ethyl acetate, and the extract was washed with water and brine, dried over magnesium sulfate and concentrated under reduced pressure to give a residual oil, which was chromatographed on silica gel eluting with dichloromethane-ethyl acetate (2:3) to give ethyl 3-{[1-methyl-5-(tritylamino)-1H-pyrazol-4-yl]amino}-3-oxopropanoate (1.23 g).

ESI-MS 491.2 [M+Na]$^+$ (positive), 467.3 [M–H]$^-$ (negative)

$^1$H-NMR(DMSO-$d_6$) δ 1.18 (3H, t, J=7.1 Hz), 2.75 (3H, s), 3.04 (2H, s), 4.07 (2H, q, J=7.1 Hz), 5.55 (1H, s), 7.1–7.4 (16H, m), 8.54 (1H, s)

Preparation 85

To a stirred solution of ethyl 3-{[1-methyl-5-(tritylamino)-1H-pyrazol-4-yl]amino}-3-oxopropanoate (1.3 g) in tetrahydrofuran (30 ml) was added 1N aqueous sodium hydroxide solution (3.1 ml), and the mixture was stirred at room temperature for 3 hours. Tetrahydrofuran was removed in vacuo and the residue was made acidic with diluted citric acid. The resulting precipitate was collected by filtration and dried under reduced pressure to give 3-{[1-methyl-5-(tritylamino)-1H-pyrazol-4-yl]amino}-3-oxopropanoic acid (1.22 g).

ESI-MS 463.2 [M+Na]$^+$ (positive)

$^1$H-NMR(DMSO-$d_6$) δ 2.74 (3H, s), 2.95 (2H, s), 5.56 (1H, s), 7.0–7.4 (16H, m), 8.54 (1H, s), 12.0–13.0 (1H, brs)

Preparation 86

To a suspension of 3-{[1-methyl-5-(tritylamino)-1H-pyrazol-4-yl]amino}-3-oxopropanoic acid (600 mg) and tert-butyl (2-aminoethyl)carbamate (240 mg) in tetrahydrofuran (12 ml) and dichloromethane (6 ml) was added WSCD HCl (522 mg), and the whole mixture was stirred at room temperature overnight. To the reaction mixture was added water (3 ml), and the whole mixture was extracted with ethyl acetate. The extract was washed with water and brine and dried over magnesium sulfate. The evaporation of the solvent gave a crude residue, which was triturated with diisopropyl ether-ethyl acetate (2:1) to give tert-butyl {2-[(3-{[1-methyl-5-(tritylamino)-1H-pyrazol-4-yl]amino}-3-oxopropanoyl)amino]ethyl}carbamate (537 mg).

ESI-MS 604.9 [M+Na]$^+$ (positive)

$^1$H-NMR(DMSO-$d_6$) δ 1.38 (9H, s), 2.74 (3H, s), 2.85 (2H, s), 2.9–3.2 (4H, m), 5.61 (1H, s), 6.7–6.9 (1H, m), 7.0–7.4 (16H, m), 8.0–8.1 (1H, m), 8.63 (1H, s)

EXAMPLE 51

3-{[3-Amino-4-({3-[(2-aminoethyl)amino]-3-oxopropanoyl}amino)-2-methyl-1-pyrazolio]methyl}-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl {2-[(3-{[1-methyl-5-(tritylamino)-1H-pyrazol-4-yl]amino]-3-oxopropanoyl)amino]ethyl}carbamate in the same manner as in Example 34.

ESI-MS 731.2 [M+Na]+ (positive)

$^1$H-NMR (D$_2$O) δ 1.53 (6H, s), 3.1–3.3 (2H, m), 3.19 and 3.44 (2H, ABq, J=17.7 Hz), 3.54 (2H, s), 3.5–3.7 (2H, m), 3.74 (3H, s), 5.00 and 5.22 (2H, ABq, J=15.5 Hz), 5.25 (1H, d, J=4.7 Hz), 5.86 (1H, d, J=4.8 Hz), 8.05 (1H, s)

Preparation 87

To a stirred solution of 3-amino-2-hydroxypropanoic acid (2.1 g) in tetrahydrofuran (30 ml) and water (30 ml) was added 1N aqueous sodium hydroxide solution to make the solution basic (pH=9). To the mixture was added di-tert-butyl dicarbonate (4.36 g), and the mixture was stirred at room temperature for 4 hours keeping pH of the mixture between 8.5 and 9.0. The whole mixture was washed with diethyl ether. The aquous layer was made acidic (pH=2) with 10% aqueous potassium hydrogen sulfate, saturated with sodium chloride and extracted with ethyl acetate. The extract was dried over magnesium sulfate. The solvent was evaporated under reduced pressure to give 3-[(tert-butoxycarbonyl)amino]-2-hydroxypropanoic acid (3.96 g).

ESI-MS 228.2 [M+Na]+ (positive)

$^1$H-NMR(DMSO-d$_6$) δ 1.37 (9H, s), 3.0–3.8 (3H, m), 3.9–4.1 (1H, m), 6.5–6.8 (1H, m)

Preparation 88

To a solution of 3-[(tert-butoxycarbonyl)amino]-2-hydroxypropanoic acid (1.61 g) in dichloromethane (8 ml) and tetrahydrofuran (8 ml) were added HOBT (1.59 g) and WSCD HCl (3.01 g), and the mixture was stirred at room temperature for 1 hour. The solution was cooled to 0° C., and 1-methyl-1H-pyrazole-4,5-diamine sulfate and N,N-diisopropylethylamine (4.1 ml) were added. The mixture was stirred at room temperature for 8 hours. The solvent was removed under reduced pressure to give crude tert-butyl {3-[(5-amino-1-methyl-1H-pyrazol-4-yl)amino]-2-hydroxy-3-oxopropyl}carbamate, which was used in the next reaction without further purification.

Preparation 89 tert-Butyl (2-hydroxy-3-{[1-methyl-5-(tritylamino)-1H-pyrazol-4-yl]amino}-3-oxopropyl)carbamate The title compound was obtained from tert-butyl {3-[(5-amino-1-methyl-1H-pyrazol-4-yl)amino]-2-hydroxy-3-oxopropyl}carbamate in the same manner as in Preparation 84.

ESI-MS 564.3 [M+Na]+ (positive)

$^1$H-NMR(DMSO-d$_6$) δ 1.39 (9H, s), 2.7–2.9 (1H, m), 2.83 (3H, s), 3.1–3.4 (1H, m), 3.7–3.9 (1H, m), 5.79 (1H, d, J=5.3 Hz), 5.98 (1H, s), 6.5–6.7 (1H, m), 7.1–7.4 (16H, m), 8.36 (1H, s)

EXAMPLE 52

3-({3-Amino-4-[(3-amino-2-hydroxypropanoyl)amino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl (2-hydroxy-3-{[1-methyl-5-(tritylamino)-1H-pyrazol-4-yl]amino}-3-oxopropyl)carbamate in the same manner as in Example 32.

$^1$H-NMR(D$_2$O) δ 1.49 (6H, s), 3.1–3.6 (4H, m), 3.76 (3H, s), 4.6–4.7 (1H, m), 5.02 and 5.21 (2H, ABq, J=15.4 Hz), 5.26 (1H, d, J=4.8 Hz), 5.86 (1H, d, J=4.8 Hz), 8.05 (1H, s)

Preparation 90

To a suspension of 2-(4,5-diamino-1H-pyrazol-1-yl)ethanol sulfate (5 g) in dichloromethane (50 ml) was added triethylamine (6.38 ml) at 0° C., and the mixture was stirred at 0° C. for 10 minutes. A mixture of acetic anhydride (2.16 ml) and formic acid (1.74 ml) was stirred at 40° C. for 30 minutes, cooled to 0° C. and added dropwise to the above solution at 0° C. The whole mixture was stirred at 0° C. for 2 hours. To the mixture was added brine, and the whole mixture was extracted with tetrahydrofuran. The extract was dried over magnesium sulfate and evaporated under reduced pressure to give crude [5-amino-1-(2-hydroxyethyl)-1H-pyrazol-4-yl]formamide, which was used in the next reaction without further purification.

Preparation 91

[1-(2-Hydroxyethyl)-5-(tritylamino)-1H-pyrazol-4-yl]formamide

The title compound was obtained from [5-amino-1-(2-hydroxyethyl)-1H-pyrazol-4-yl]formamide in the same manner as in Preparation 84. The NMR spectrum of this compound indicates the existence of its rotamer.

$^1$H-NMR(DMSO-d$_6$) δ 3.10 (2H, t, J=6.2 Hz), 3.3–3.5 and 3.4–3.6 (2H, m), 4.89 and 5.06 (1H, t, J=5.1 Hz), 5.77 and 6.07 (1H, s), 7.1–7.4 (16H, m), 7.58 and 8.07 (1H, s), 7.58 (1H, s)

Preparation 92

To a stirred solution of [1-(2-hydroxyethyl)-5-(tritylamino)-1H-pyrazol-4-yl]formamide (2 g) in N,N-dimethylformamide (30 ml) was added sodium hydride (213 mg, 60% oil suspension) under a nitrogen stream at, 0° C., and the whole mixture was stirred at 0° C. for 20 minutes. A solution of tert-butyl (3-bromopropyl)carbamate (1.27 g) in N,N-dimethylformamide (10 ml) and sodium iodide (799 mg) were added to the above solution, and the mixture was stirred overnight. 10% Aqueous potassium hydrogen sulfate solution (5 ml) was added, and the whole mixture was extracted with ethyl acetate. The extract was washed with water and brine and dried over magnesium sulfate. Evaporation of the solvent under reduced pressure gave an oil, which was chromatographed on silica gel eluting with dichloromethane-ethyl acetate (2:1) to give tert-butyl (3-{N-formyl-N-[1-(2-hydroxyethyl)-5-(tritylamino)-1H-pyrazol-4-yl]amino}propyl)carbamate (1 g). The NMR spectrum of this compound indicates the existence of its rotamer.

ESI-MS 592.3 [M+Na]$^+$ (positive)

$^1$H-NMR(DMSO-d$_6$) δ 1.37 and 1.38 (9H, s), 2.7–3.5 (10H, m), 4.80 and 4.88 (1H, t, J=5.0 Hz), 5.52 & 6.06 (1H, s), 6.5–6.9 (1H, m), 7.0–7.4 (16H, m), 7.52 (1H, s)

EXAMPLE 53

3-({3-Amino-4-[N-(3-aminopropyl)-N-formylamino]-2-(2-hydroxyethyl)-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl (3-{N-formyl-N-[1-(2-hydroxyethyl)-5-(tritylamino)-1H-pyrazol-4-yl]amino}propyl)carbamate in the same manner as in Example 32.

ESI-MS 694.2 [M−H]$^−$ (negative)

$^1$H-NMR(D$_2$O) δ 1.53 (6H, s), 1.7–2.1 (2H, m), 2.9–3.1 (2H, m), 3.1–3.8 (4H, m), 3.8–4.0 (2H, m), 4.3–4.6 (2H, m), 4.8–5.2 (2H, m), 5.29 (1H, d, J=4.8 Hz), 5.85 (1H, d, J=4.7 Hz), 8.0–8.3 (2H, m)

EXAMPLE 54

To a stirred suspension of 3-({3-amino-4-[N-(3-aminopropyl)-N-formylamino]-2-(2-hydroxyethyl)-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate (100 mg) in methanol (1.4 ml) was added concentrated hydrochloric acid (0.125 ml) at room temperature, and the mixture was stirred for 6.5 hours. To the above solution was added sodium hydrogen carbonate (109 mg), and the mixture was purified by preparative HPLC (ODS column; acetonitrile:phosphate buffer (pH 7)=5:95). The eluate containing a desired product was evaporated to remove acetonitrile, made acidic with diluted hydrochloric acid and chromatographed on Diaion® HP20 (Mitsubishi Chemical Corporation) eluting with 20% aqueous 2-propanol. The eluate was concentrated under reduced pressure and lyophilized to give 3-({3-amino-4-[(3-aminopropyl)amino]-2-(2-hydroxyethyl)-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate (18 mg).

ESI-MS 666.2 [M−H]$^−$ (negative)

$^1$H-NMR(DMSO-d$_6$) δ 1.53 (6H, s), 1.96 (2H, tt, J=7.5 Hz), 3.0–3.2 (4H, m), 3.13 and 3.43 (2H ABq, J=17.6 Hz), 3.87 (2H, t, J=4.8 Hz), 4.2–4.4 (2H, m), 4.87 and 5.03 (2H, ABq, J=15.2 Hz), 5.24 (1H, d, J=4.8 Hz), 5.83 (1H, d, J=4.8 Hz), 7.64 (1H, s)

Preparation 93

To a stirred solution of N-[1-methyl-5-(tritylamino)-1H-pyrazol-4-yl]-2-(tritylamino)acetamide (2 g) in N,N-dimethylformamide (20 ml) was added sodium hydride (245 mg, 60% oil suspension) at 0° C., and the mixture was stirred for 30 minutes with warming to room temperature. The mixture was cooled to 0° C., and methyl iodide (1.3 g) was added. The whole mixture was stirred at room temperature overnight. Water (5 ml) was added, and the whole mixture was extracted with ethyl acetate. The organic layer was washed with water and brine and dried over magnesium sulfate. Evaporation of the solvent under reduced pressure gave N-methyl-N-[1-methyl-5-(tritylamino)-1H-pyrazol-4-yl]-2-(tritylamino)acetamide (2.05 g).

ESI-MS 690.3 [M+Na]$^+$ (positive)

$^1$H-NMR(DMSO-d$_6$) δ 1.99 (3H, s), 2.3–2.8 (3H, m), 2.52 (3H, s), 5.44 (1H, s), 6.85 (1H, s), 6.9–7.5 (30H, m)

Preparation 94

Lithium aluminum hydride (455 mg) was added slowly to tetrahydrofuran (40 ml) at 0° C. and the mixture was stirred for 20 minutes. N-Methyl-N-[1-methyl-5-(tritylamino)-1H-pyrazol-4-yl]-2-(tritylamino)acetamide (2 g) was added to the mixture at 0° C., and the whole mixture was stirred for 2 hours with warming to room temperature and refluxed for 2 hours. Sodium fluoride (2.51 g) and water (862 mg) were added to the mixture, and the whole mixture was stirred at room temperature for 30 minutes. The precipitate was filtered off, and the filtrate was concentrated under reduced pressure to give crude residue, which was chromatographed (silica gel; ethyl acetate:dichloromethane=1:10) to give N$^4$,1-dimethyl-N$^5$-trityl-N$^4$-[2-(tritylamino)ethyl]-1H-pyrazole-4,5-diamine (740 mg).

ESI-MS 676.2 [M+Na]$^+$ (positive)

$^1$H-NMR(DMSO-d$_6$) δ 1.7–2.0 (2H, m), 1.98 (3H, s), 2.2–2.4 (1H, m), 2.6–2.8 (2H, m), 2.81 (3H, s), 5.24 (1H, s), 7.00 (1H, s), 7.0–7.5 (30H, m)

EXAMPLE 55

3-({3-Amino-4-[N-(2-aminoethyl)-N-methylamino]-2-methyl-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from N$^4$,1-dimethyl-N$^5$-trityl-N$^4$-[2-(tritylamino)ethyl]-1H-pyrazole-4,5-diamine in the same manner as in Example 32.

ESI-MS 636.2 [M−H]$^−$ (negative)

$^1$H-NMR(D$_2$O) δ 1.60 (6H, s), 2.60 (3H, s), 3.0–3.2 (4H, m), 3.19 and 3.39 (2H, ABq, J=17.7 Hz), 3.67 (3H, s), 4.87 and 5.20 (2H, ABq, J=15.8 Hz), 5.22 (1H, d, J=4.9 Hz), 5.85 (1H, d, J=4.7 Hz), 7.90 (1H, s)

Preparation 95

To a solution of [1-(2-fluoroethyl)-1H-pyrazol-5-yl]formamide (15.7 g) in methanol (78 ml) was added concentrated hydrochloric acid (21 ml) at room temperature. The reaction mixture was stirred for 3.5 hours and evaporated in vacuo. The residue was dissolved in ethyl acetate and washed with aqueous sodium hydrogen carbonate solution. The organic layer was dried over magnesium sulfate and concentrated in vacuo to give 1-(2-fluoroethyl)-1H-pyrazol-5-amine (12 g).

$^1$H-NMR(DMSO-d$_6$) δ 4.15 (2H, dt, J=25.2, 5.1 Hz), 4.66 (2H, dt, J=47.2, 5.1 Hz), 5.1 (2H, brs), 5.27 (1H, d, J=1.7 Hz), 7.06 (1H, d, J=1.7 Hz)

Preparation 96

To a solution of 1-(2-fluoroethyl)-1H-pyrazol-5-amine (12 g) in ethanol (30 ml) were added concentrated hydrochloric acid (70 mg) and isoamyl nitrite (10.9 g). The reaction mixture was stirred at 25–38° C. for 2 hours. Diisopropyl ether and hexane were added to the reaction mixture, and the resulting oil was purified by column chromatography on silica gel (ethyl acetate:hexane=1:2→1:1→2:1→1:0) to give 1-(2-fluoroethyl)-4-nitroso-1H-pyrazol-5-amine (4.8 g).

$^1$H-NMR(DMSO-d$_6$) δ 4.10–4.90 (4H, m), 7.09 and 8.59 (1H, s), 8.20 and 8.26 (1H, brs)

Preparation 97

To a solution of 1-(2-fluoroethyl)-4-nitroso-1H-pyrazol-5-amine (4.8 g) in water (30 ml) and methanol (30 ml) were added sulfuric acid (2.98 g) and 10% palladium on carbon (2.5 g), and the mixture was hydrogenated under balloon pressure for 7.5 hours. The reaction mixture was filtered through a bed of Celite, and the filtrate was concentrated in vacuo. 2-Propanol was added to the residue, and the precipitate was collected by filtration to give 1-(2-fluoroethyl)-1H-pyrazole-4,5-diamine sulfate (7 g).

$^1$H-NMR(D$_2$O) δ 4.25–4.95 (4H, m), 7.66 (1H, s)

Preparation 98

To a suspension of 1-(2-fluoroethyl)-1H-pyrazole-4,5-diamine sulfate (3 g) in tetrahydrofuran (30 ml) were added tert-butyl {3-[(2,5-dioxo-1-pyrrolidinyl)oxy]-3-oxopropyl}carbamate (3.9 g) and N,N-diisoporpylethylamine (3.5 g) under ice-cooling. The reaction mixture was stirred at room temperature for 2 hours. An aqueous sodium hydrogen carbonate solution and sodium chloride were added, and the mixture was extracted with ethyl acetate-tetrahydrofuran (three times). The organic layer was dried over magnesium sulfate and concentrated in vacuo. The residue was purified by column chromatography on silica gel (ethyl acetate→ethyl acetate:ethanol=8:1) to give tert-butyl (3-{[5-amino-1-(2-fluoroethyl)-1H-pyrazol-4-yl]amino}-3-oxopropyl)carbamate (2.3 g).

$^1$H-NMR(DMSO-d$_6$) δ 1.38 (9H, s), 2.36 (2H, t, J=7.1 Hz), 3.10–3.27 (2H, m), 4.16 (2H, dt, J=25.5, 5.0 Hz), 4.67 (2H, dt, J=47.2, 5.0 Hz), 5.27 (2H, brs), 6.75–6.90 (1H, m), 7.23 (1H, s), 9.08 (1H, brs)

Preparation 99

To a solution of tert-butyl (3-{[5-amino-1-(2-fluoroethyl)-1H-pyrazol-4-yl]amino}-3-oxopropyl)carbamate (2.3 g) in N,N-dimethylformamide (12 ml) were added triethylamine (1.48 g), 4-dimethylaminopyridine (35.6 mg) and trityl chloride (2.2 g) at room temperature. The reaction mixture was stirred for 2 hours, and water was added. The mixture was extracted with ethyl acetate, and the organic layer was washed with water and aqueous sodium chloride solution. The organic layer was dried over magnesium sulfate and concentrated in vacuo. Acetonitrile was added, and the precipitate was collected by filtration to give tert-butyl (3-{[1-(2-fluoroethyl)-5-(tritylamino)-1H-pyrazol-4-yl]amino}-3-oxopropyl)carbamate (2 g).

$^1$H-NMR(DMSO-d$_6$) δ 1.39 (9H, s), 2.05 (2H, t, J=7.2 Hz), 3.00–3.08 (2H, m), 3.23 (2H, dt, J=25.3, 5.1 Hz), 4.41 (2H, dt, J=47.1, 5.1 Hz)

EXAMPLE 56

3-({3-Amino-4-[(3-aminopropionyl)amino]-2-(2-fluoroethyl)-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl (3-{[1-(2-fluoroethyl)-5-(tritylamino)-1H-pyrazol-4-yl]amino}-3-oxopropyl)carbamate in the same manner as in Example 38.

$^1$H-NMR(D$_2$O) δ 2.89 (2H, t, J=6.5 Hz), 3.22 (1H, d, J=9.2 Hz), 3.34 (1H, t, J=6.5 Hz), 3.50 (1H, d, J=9.2 Hz), 4.55–4.95 (4H, m), 5.08 (2H, brs), 5.26 (1H, d, J=4.9 Hz), 5.84 (1H, d, J=4.9 Hz), 8.09 (1H, s)

Preparation 100

1-Methyl-7-nitroso-1H-imidazo[1,2-b]pyrazole

The title compound was obtained from 1-methyl-1H-imidazo[1,2-b]pyrazole in the same manner as in Preparation 96.

$^1$H-NMR(DMSO-d$_6$) δ 3.93 (1H, s), 7.48 (1H, m), 7.92 (1H, m), 9.03 (1H, s)

Preparation 101

1-Methyl-1H-imidazo[1,2-b]pyrazol-7-amine sulfate

The title compound was obtained from 1-methyl-7-nitroso-1H-imidazo[1,2-b]pyrazole in the same manner as in Preparation 97.

$^1$H-NMR(DMSO-d$_6$) δ 3.73 (3H, s), 7.24 (1H, m), 7.62 (2H, m)

Preparation 102

Di-tert-butyl {(Z)-[(1-methyl-1H-imidazo[1,2-b]pyrazol-7-yl)amino]methylidene}biscarbamate The title compound was obtained from 1-methyl-1H-imidazo[1,2-b]pyrazol-7-amine sulfate in the same manner as in Preparation 64.

$^1$H-NMR(DMSO-d$_6$) δ 1.34 (9H, s), 1.52 (9H, s), 3.61 (3H, s), 7.14 (1H, m), 7.42 (1H, m), 7.52 (1H, m)

EXAMPLE 57

7β-[(Z)-2-(5-Amino-1,2,4-thiadiazol-3-yl)-2-(1-carboxy-1-methylethoxyimino)acetamido]-3-{[7-guanidino-1-methyl-5-(1H-imidazo[1,2-b]pyrazolio)]methyl}-3-cephem-4-carboxylate The title compound was obtained from di-tert-butyl {(Z)-[(1-methyl-1H-imidazo[1,2-b]pyrazol-7-yl)amino]methylidene}biscarbamate in the same manner as in Example 43.

$^1$H-NMR(D$_2$O) δ 1.51 (6H, s), 3.40 (2H, m), 3.85 (3H, s), 5.15–5.30 (3H, m), 5.83 (1H, d, J=4.8 Hz), 7.49 (1H, d, J=2.2 Hz), 8.02 (1H, d, J=2.2 Hz), 8.27 (1H, d, J=1.0 Hz)

IR(KBr) 3400, 3392, 1770, 1672, 1606, 1531 cm$^{-1}$

Preparation 103 tert-Butyl {3-[(1-methyl-1H-imidazo[1,2-b]pyrazol-7-yl)amino]-3-oxopropyl}carbamate The title compound was obtained from 1-methyl-1H-imidazo[1,2-b]pyrazol-7-amine sulfate and 3-[(tert-butoxycarbonyl)amino]propanoic acid in the same manner as in Preparation 70.

$^1$H-NMR(DMSO-d$_6$) δ 1.43 (9H, s), 2.61 (2H, m), 3.49 (2H, m), 3.65 (3H, s), 7.22 (1H, m), 7.26 (1H, m), 7.44 (1H, m)

EXAMPLE 58

3-({7-[(3-Aminopropanoyl)amino]-1-methyl-5-(1H-imidazo[1,2-b]pyrazolio)}methyl)-7β-[(Z)-2-(5-amino-1,2,4-thiadiazol-3-yl)-2-(1-carboxy-1-methylethoxyimino)acetamido]-3-cephem-4-carboxylate The title compound was obtained from tert-butyl {3-[(1-methyl-1H-imidazo[1,2-b]pyrazol-7-yl)amino]-3-oxopropyl}carbamate in the same manner as in Example 43.

$^1$H-NMR(D$_2$O) δ 1.50 (6H, s), 2.97 (2H, d, J=6.5 Hz), 3.36 (2H, d, J=6.5 Hz), 3.4 (2H, m), 3.81 (3H, s), 5.15–5.30 (3H, m), 5.82 (1H, d, J=4.8 Hz), 7.44 (1H, d, J=2.2 Hz), 7.98 (1H, d, J=2.2 Hz), 8.11 (1H, d, J=1.0 Hz)

IR(KBr) 3401, 1770, 1666, 1606, 1525 cm$^{-1}$

Preparation 104

To a suspension of phenyl [1-methyl-5-(tritylamino)-1H-pyrazol-4-yl]carbamate (4.6 g) in N,N-dimethylformamide (32 ml) were added triethylamine (1.08 g) and tertbutyl 1-piperazinecarboxylate (1.99 g). The reaction mixture was stirred for 3 hours and poured into water. The mixture was extracted with ethyl acetate, and the organic layer was concentrated in vacuo. The residue was purified by column chromatography on silica gel (ethyl acetate→ethyl acetate:ethanol=20:1) to give tert-butyl 4-({[1-methyl-5-(tritylamino)-1H-pyrazol-4-yl]amino}carbonyl)-1-piperazinecarboxylate (4.7 g)

$^1$H-NMR(CDCl$_3$) δ 1.46 (9H, s), 2.90 (3H, s), 3.05–3.25 (4H, m), 3.30–3.45 (4H, m), 4.76 (1H, brs), 5.34 (1H, brs), 7.10–7.30 (16H, m)

EXAMPLE 59

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (2 g) in N,N-dimethylformamide (6 ml) was added 1,3-bis(trimethylsilyl)urea (3 g), and the reaction mixture was stirred for 30 minutes. Potassium iodide (680 mg) was added to this solution, and the mixture was stirred for 30 minutes tert-Butyl 4-({[1-methyl-5-(tritylamino)-1H-pyrazol-4-yl]amino}carbonyl)-1-piperazinecarboxylate (2 g) was added to this solution. The reaction mixture was stirred at 25° C. for 23 hours and poured into a mixture of ethyl acetate-water-20% aqueous sodium chloride solution. The organic layer was washed with a mixture of 10% aqueous sodium thiosulfate solution and 20% aqueous sodium chloride solution. The organic layer was washed successively with 10% aqueous sodium trifluoroacetate solution twice and 20% aqueous sodium chloride solution. The organic layer was concentrated in vacuo to a volume of approximately 10 ml. The concentrate was added to diisopropyl ether, and the suspension was stirred for 1 hour. The resulting solid was collected by filtration and dried.

The solid was dissolved in dichloromethane (6 ml). To this solution was added anisole (2 ml) and trifluoroacetic acid (6 ml). The reaction mixture was stirred for 4 hours and poured into diisopropyl ether. The resulting solid was collected by filtration and dried. This solid was purified by preparative HPLC utilizing ODS column. The eluate containing a desired product was concentrated in vacuo. The concentrate was adjusted to about pH 1 with concentrated hydrochloric acid and chromatographed on Diaion® HP-20 (Mitsubishi Chemical Corporation) eluting with 20% aqueous 2-propanol. The eluate was concentrated in vacuo, and 2M sulfuric acid was added. The mixture was lyophilized to give 3-({3-amino-2-methyl-4-[(1-piperazinylcarbonyl)amino]-1-pyrazolio}methyl)-7β-[(Z)-2-(5-amino-1,2,4-thiadiazol-3-yl)-2-(1-carboxy-1-methylethoxyimino)acetamido]-3-cephem-4-carboxylic acid hydrogen sulfate (679 mg).

$^1$H-NMR(D$_2$O) δ 1.60 (6H, s), 3.20 (2H, d, J=17.7 Hz), 3.25–3.45 (4H, m), 3.45 (1H, d, J=17.7 Hz), 3.72 (3H, m), 3.75–3.85 (4H, m), 5.00 (1H, d, J=15.7 Hz), 5.24 (1H, d, J=15.7 Hz), 5.25 (1H, d, J=4.8 Hz), 5.86 (1H, d, J=4.8 Hz), 7.89 (1H, s)

This application is based on application No. 2002952355 filed in Australia on Oct. 30, 2002, and application No. 2003904813 filed in Australia on Sep. 4, 2003, the content of which is incorporated hereinto by reference.

The invention claimed is:

1. A compound of the formula [I]:

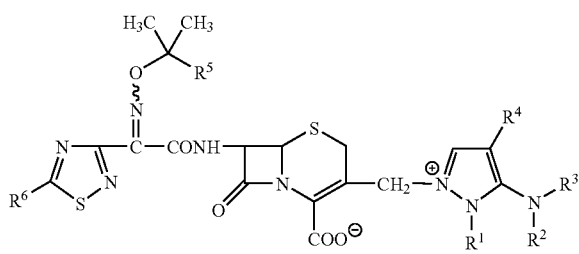

wherein
R$^1$ is lower alkyl, hydroxy(lower)alkyl or halo(lower)alkyl, and
R$^2$ is hydrogen, aryl(lower)alkyl or acyl, or
R$^1$ and R$^2$ are bonded together and form lower alkylene or lower alkenylene;
R$^3$ is hydrogen or lower alkyl;
R$^4$ is

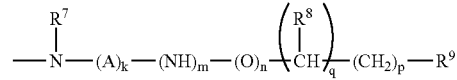

wherein
A is

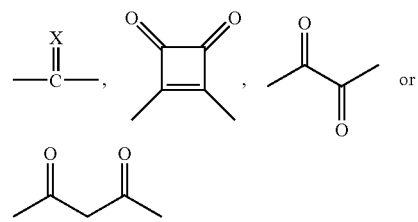

wherein X is O or NH,
R$^7$ is hydrogen, lower alkyl, aryl(lower)alkyl or acyl,
R$^8$ is hydrogen or hydroxy,
R$^9$ is amino, mono or di(lower)alkylamino, aryl(lower)alkylamino, acyl amino, guanidino, acyl guanidino or saturated 3- to 8-membered heterocyclic group containing 1 to 4 nitrogen atoms optionally substituted by amino, aryl(lower)alkylamino or acylaminio,
k, m, n and q are independently 0 or 1, and
p is 0, 1, 2 or 3;
$R^5$ is carboxy or an esterfied carboxy; and
$R^6$ is amino, aryl(lower)alkylamino or acylamino,
or a pharmaceutically acceptable salt thereof.
2. The compound of claim 1 wherein
$R^1$ is lower alkyl or hydroxy(lower)alkyl, and
$R^2$ is hydrogen, aryl(lower)alkyl or acyl, or
$R^1$ and $R^2$ are bonded together and form lower alkylene;
$R^3$ is hydrogen;
A is

wherein X is O or NH;
$R^7$ is hydrogen, aryl(lower)alkyl or acyl;
$R^9$ is amino, aryl(lower)alkylamino or acylamino; and
p is 0, 1 or 2,
or a pharmaceutically, acceptable salt thereof.
3. The compound of claim 2 wherein $R^8$ is hydrogen, or a pharmaceutically acceptable salt thereof.
4. The compound of claim 1 wherein
$R^1$ is lower alkyl, hydroxy(lower)alkyl or halo(lower)alkyl, and
$R^2$ is hydrogen, aryl(lower)alkyl or acyl, or
$R^1$ and $R^2$ are bonded together and form lower alkylene or lower alkenylene;
$R^5$ is carboxy or esterified carboxy;
$R^6$ is amino or acylamino;
$R^7$ is hydrogen, lower alkyl or acyl; and
$R^9$ is amino, mono or di(lower)alkylamino, acylamino, guanidino, acylguanidino or saturated 3- to 8-membered heterocyclic group containing 1 to 4 nitrogen atoms optionally substituted by amino or acylamino,
or a pharmaceutically acceptable salt thereof.
5. The compound of claim 4 wherein
$R^1$ is lower alkyl or hydroxy(lower)alkyl, and
$R^2$ is hydrogen, aryl(lower)alkyl or acyl, or
$R^1$ and $R^2$ are bonded together and form lower alkylene;
$R^5$ is carboxy or esterified carboxy;
$R^6$ is amino or acylamino;
$R^7$ is hydrogen or acyl; and
$R^9$ is amino or acylamino,
or a pharmaceutically acceptable salt thereof.
6. The compound of claim 5 wherein
$R^1$ is lower alkyl or hydroxy(lower)alkyl, and
$R^2$ is hydrogen, aryl(lower)alkyl, lower alkanoyl or lower alkoxycarbonyl, or
$R^1$ and $R^2$ are bonded together and form lower alkylene;
$R^5$ is carboxy or lower alkoxycarbonyl;
$R^6$ is amino, lower alkanoylamino or lower alkoxycarbonylamino;
$R^7$ is hydrogen, lower alkanoyl or lower alkoxycarbonyl; and
$R^9$ is amino, lower alkanoylamino or lower alkoxycarbonylamino,
or a pharmaceutically acceptable salt thereof.
7. The compound of claim 6 wherein
$R^1$ is lower alkyl or hydroxy(lower)alkyl, and
$R^2$ is hydrogen, or
$R^1$ and $R^2$ are bonded together and form lower alkylene;

$R^5$ is carboxy;
$R^6$ is amino;
$R^7$ is hydrogen or lower alkanoyl; and
$R^9$ is amino,
or a pharmaceutically acceptable salt thereof.
8. The compound of claim 1 wherein
$R^4$ is selected from the group consisting of

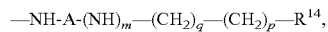

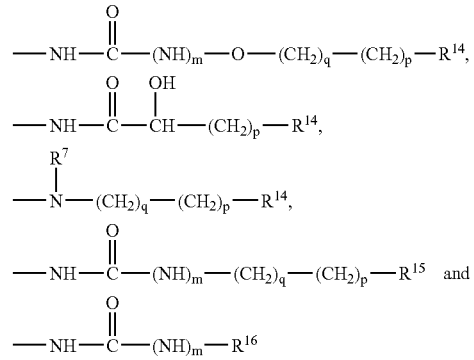

wherein $R^7$, A, m, p and q are each as defined in claim 1,
$R^{14}$ is amino, mono or di(lower)alkylamino, aryl(lower)alkylamino or acylamino,
$R^{15}$ is guanidino or acyl guanidino, and
$R^{16}$ is saturated 3- to 8-membered heterocyclic group containing 1 to 4 nitrogen atoms optionally substituted by amino, aryl(lower)alkylamino or acylamino,
or a pharmaceutically acceptable salt thereof.
9. The compound of claim 1 wherein
$R^4$ is selected from the groups consisting of

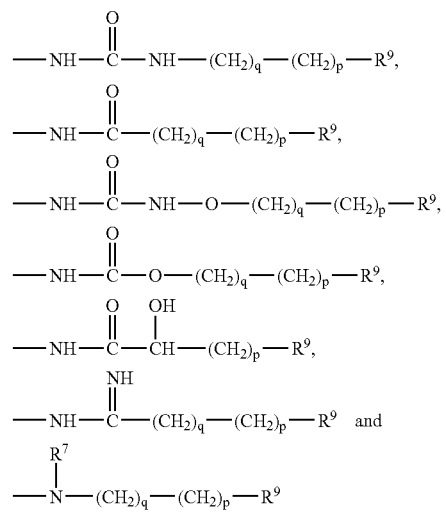

wherein
p is 0, 1 or 2,
q is 0 or 1,
$R^7$ is hydrogen, aryl(lower)alkyl or acyl, and
$R^9$ is amino, aryl(lower)alkylamino or acylamino,
or a pharmaceutically acceptable salt thereof.

10. The compound of claim 9 wherein

R$^7$ is hydrogen, lower alkanoyl or lower alkoxycarbonyl; and

R$^9$ is amino, lower alkanoylamino or lower alkoxycarbonylamino, or a pharmaceutically acceptable salt thereof.

11. The compound of claim 10 wherein

R$^7$ is hydrogen or lower alkanoyl; and

R$^9$ is amino, or a pharmaceutically acceptable salt thereof.

12. A process for preparing a compound of the formula [I]:

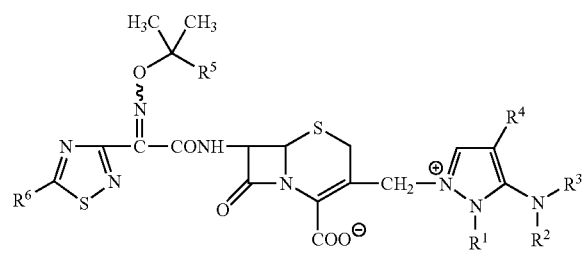

wherein

R$^1$ is lower alkyl, hydroxy(lower)alkyl or halo(lower)alkyl, and

R$^2$ is hydrogen, aryl(lower)alkyl or acyl, or

R$^1$ and R$^2$ are bonded together and form lower alkylene or lower alkenylene;

R$^3$ is hydrogen or lower alkyl;

R$^4$ is

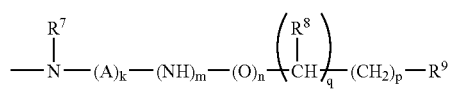

wherein

A is

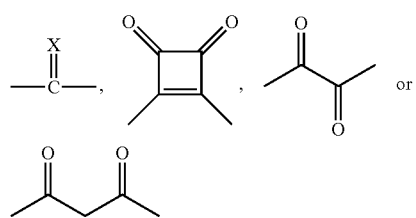

wherein X is O or NH,

R$^7$ is hydrogen, lower alkyl, aryl(lower)alkyl or acyl,

R$^8$ is hydrogen or hydroxy,

R$^9$ is amino, mono or di(lower)alkylamino, aryl(lower)alkylamino, acyl amino, guanidino, acyl guanidino or saturated 3- to 8-membered heterocyclic group containing 1 to 4 nitrogen atoms optionally substituted by amino, aryl(lower)alkylamino or acylamino, k, m, n and q are independently 0 or 1, and p is 0, 1, 2 or 3;

R$^5$ is carboxy or an esterfied carboxy; and

R$^6$ is amino, aryl(lower)alkylamino or acylamino, or a salt thereof, which comprises (1) reacting a compound of the formula [II]:

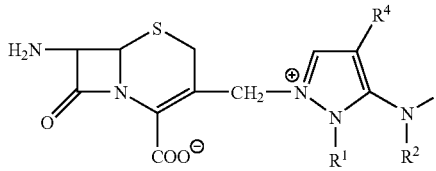

wherein R$^1$, R$^2$, R$^3$ and R$^4$ are each as defined above, or its reactive derivative at the amino group, or a salt thereof with a compound of the formula [III]:

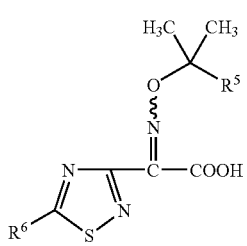

wherein R$^5$ and R$^6$ are each as defined above, or its reactive derivative at the carboxy group, or a salt thereof to give a compound of the formula [I]:

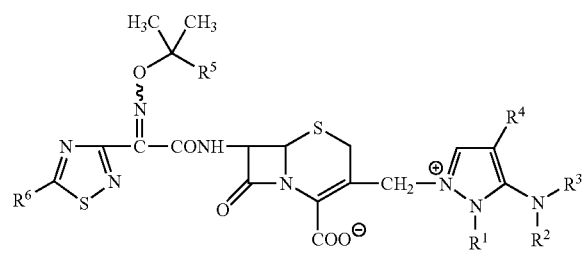

wherein R$^1$, R$^2$, R$^3$, R$^4$, R$^5$ and R$^6$ are each as defined above, or a salt thereof, or (2) subjecting a compound of the formula [Ia]:

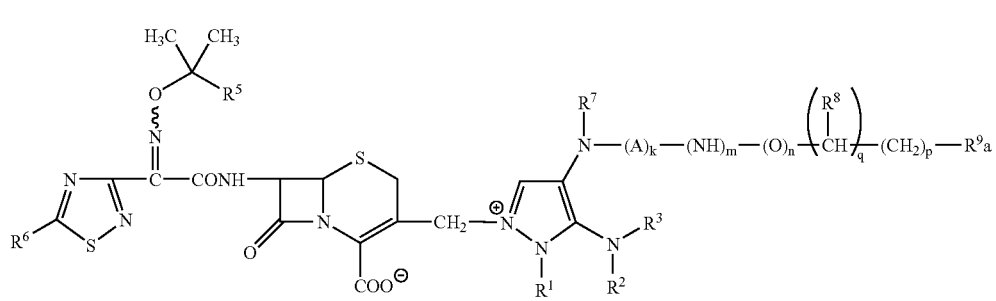

[Ia]

wherein $R^1$, $R^2$, $R^3$, $R^5$, $R^6$, $R^7$, $R^8$, A, k, m, n, p and q are each as defined above, and $R^9a$ is, aryl(lower)alkylamino or acylamino, acylguanidino or saturated 3- to 8-membered heterocyclic group containing 1 to 4 nitrogen atoms substituted by aryl(lower)alkylamino or acylamino, or a salt thereof to elimination reaction of a protecting group on the amino to give a compound of the formula [Ib]:

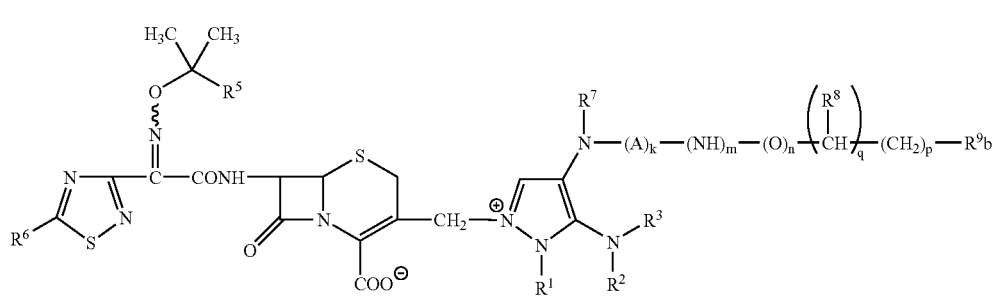

[Ib]

wherein $R^1$, $R^2$, $R^3$, $R^5$, $R^6$, $R^7$, $R^8$, A, k, m, n, p and q are each as defined above, and $R^9b$ is amino, guanidino or saturated 3- to 8-membered heterocyclic group containing 1 to 4 nitrogen atoms substituted by amino, or a salt thereof, or (3) reacting a compound of the formula [VI]:

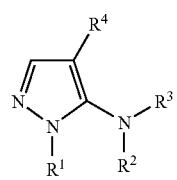

[VI]

wherein $R^5$ and $R^6$ are each as defined above, $R^{10}$ is an esterified carboxy, and Y is a leaving group, or a salt thereof with a compound of the formula [VII]:

[VII]

wherein $R^1$, $R^2$, $R^3$ and $R^4$ are each as defined above, or a salt thereof to give a compound of the formula [VIII]:

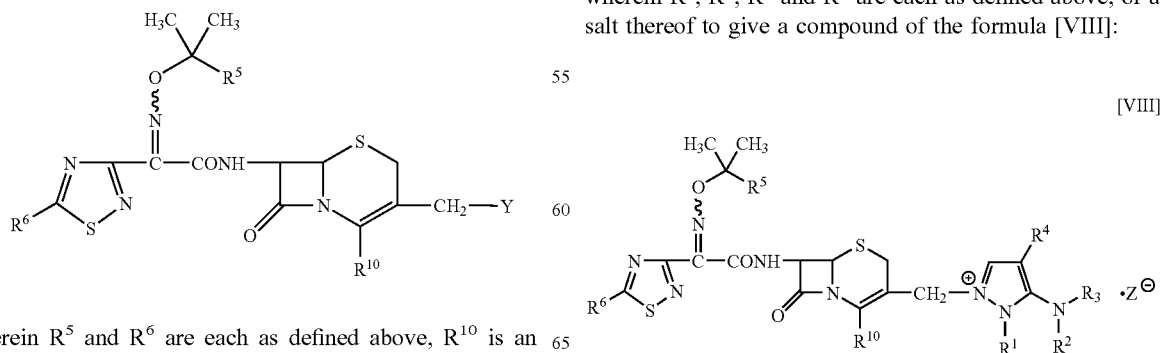

[VIII]

wherein $R^1$, $R^2$, $R^3$, $R^4$, $R^5$, $R^6$ and $R^{10}$ are each as defined above, and Z is an anion, or a salt thereof, and subjecting the compound of the formula [VIII] or a salt thereof to elimination reaction of the group protecting the esterfied carboxy, to give a compound of the formula [I]:

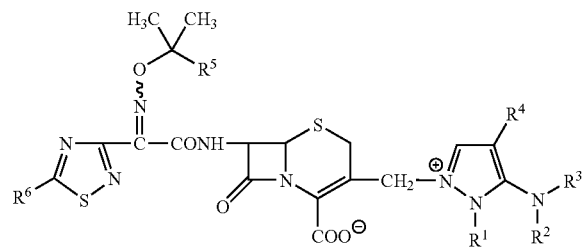

[I]

wherein $R^1$, $R^2$, $R^3$, $R^4$, $R^5$ and $R^6$ are each as defined above, or a salt thereof.

13. A pharmaceutical composition comprising a compound of claim 1 or a pharmaceutically acceptable salt thereof in admixture with a pharmaceutically acceptable carrier.

14. A method for treating a bacterial infection comprising administering a compound of claim 1 or a pharmaceutically acceptable salt thereof to human or animals.

15. The compound of claim 1, which is 7β-[(Z)-2-(5-amino-1,2,4-thiadiazol-3-yl)-2-(1-carboxy-1-methylethoxyimino)acetamido]-3-[7-(3-aminopropionamido)-2,3-dihydro-5-(1H-imidazo[1,2-b]pyrazolio)]methyl-3-cephem-4-carboxylate.

16. The compound of claim 1, which is 7β-[(Z)-2-(5-amino-1,2,4-thiadiazol-3-yl)-2-(1-carboxy-1-methylethoxyimino)acetamido]-3-[3-amino-4-(3-aminopropionamido)-2-methyl-1-pyrazolio]methyl-3-cephem-4-carboxylate.

17. The compound of claim 1, which is 7β-[(Z)-2-(5-amino-1,2,4-thiadiazol-3-yl)-2-(1-carboxy-1-methylethoxyimino)acetamido]-3-[3-amino-4-(aminoacetyl)amino-2-methyl-1-pyrazolio]methyl-3-cephem-4-carboxylic acid hydrogen sulfate.

18. The compound of claim 1, which is 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate.

19. The compound of claim 1, which is 7β-[(Z)-2-(5-amino-1,2,4-thiadiazol-3-yl)-2-(1-carboxy-1-methylethoxyimino)acetamido]-3-(3-amino-4-guanidino-2-methyl-1-pyrazolio)methyl-3-cephem-4-carboxylic acid hydrogen sulfate.

* * * * *